United States Patent
Frank et al.

(10) Patent No.: US 8,937,092 B2
(45) Date of Patent: Jan. 20, 2015

(54) ARYL OR N-HETEROARYL SUBSTITUTED METHANESULFONAMIDE DERIVATIVES AS VANILLOID RECEPTOR LIGANDS

(71) Applicant: Gruenenthal GmbH, Aachen (DE)

(72) Inventors: Robert Frank, Aachen (DE); Gregor Bahrenberg, Monschau-Konzen (DE); Thomas Christoph, Aachen (DE); Bernhard Lesch, Aachen (DE); Jeewoo Lee, Seoul (KR)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/626,315

(22) Filed: Sep. 25, 2012

(65) Prior Publication Data

US 2013/0079377 A1    Mar. 28, 2013

Related U.S. Application Data

(60) Provisional application No. 61/539,181, filed on Sep. 26, 2011.

(30) Foreign Application Priority Data

Sep. 26, 2011  (EP) .................................... 11007807

(51) Int. Cl.
*C07D 213/40* (2006.01)
*A61K 31/44* (2006.01)

(52) U.S. Cl.
CPC ................................... *C07D 213/40* (2013.01)
USPC ........................................... 514/357; 546/331

(58) Field of Classification Search
None
See application file for complete search history.

(56) References Cited

U.S. PATENT DOCUMENTS

| 7,799,782 B2 | 9/2010 | Munson et al. |
| 2007/0105861 A1 | 5/2007 | Lee et al. |

FOREIGN PATENT DOCUMENTS

| JP | 2005-314407 A | 11/2005 |
| WO | WO 2007/045462 A2 | 4/2007 |
| WO | WO 2007/045462 A3 | 6/2007 |
| WO | WO 2011/109441 A1 | 9/2011 |

OTHER PUBLICATIONS

WebMD, Pain Coach, Drug & Medications Search, pp. 1-5, Nov. 12, 2013.*
Extended European Search Report dated Dec. 22, 2011 (six (6) pages).
Bennett et al., "A Peripheral Mononeuropathy in Rat That Produces Disorders on Pain Sensation Like Those Seen in Man," 1988, Pain, vol. 33, pp. 87-107.
Kim et al., "An Experimental Model for Peripheral Neuropathy Produced by Segmental Spinal Nerve Ligation in the Rat," 1992, Pain, vol. 50, pp. 355-363.
D'Amour et al., "A Method for Determining Loss of Pain Sensation," The Biologic Research Laboratory, University of Denver, 1941, pp. 74-79.
DuBuisson et al., "The Formalin test: A Quantitative Study of the Analgesic Effects of Morphine, Meperidine, and Brain Stem Stimulation in Rats and Cats," 1977, Pain, vol. 4, pp. 161-174.
Smith et al., "March's Advanced Organic Chemistry: Reactions, Mechanisms, and Structure," $6^{th}$ Edition—Table of Content, 2007 (four (4) pages).
Carey et al. "Advanced Organic Chemistry—Part A:Structure and Mechanisms," $5^{th}$ Edition, 2007 (twenty-two (22) pages).
Carey et al., "Advanced Organic Chemistry—Part B: Reactions and Synthesis," $5^{th}$ Edition, 2007 (twenty-nine (29) pages).
Smith, "Compendium of Organic Synthetic Methods," A John Wiley & Sons Inc., 2009, Table of Content (fifteen (15) pages).
Cheng et al., "Relationship Between the Inhibition Constant ($K_1$) and the Concentration of Inhibitor Which Causes 50 Per Cent Inhibition ($I_{50}$) of and Enzymatic Reaction," Biochemical Pharmacology, 1973, vol. 22, pp. 3099-3108.
Remington's Pharmaceutical Sciences, A.R. Gennaro (Editor), $17^{th}$ edition, 1985, Chapters 77-86 (one hundred twenty-nine (129) pages).
Remington's Pharmaceutical Sciences, A.R. Gennaro (Editor), $17^{th}$ edition, 1985, Chapter 76 (fifteen (15) pages).
Remington's Pharmaceutical Sciences, A.R. Gennaro (Editor), $17^{th}$ edition, 1985, Chapters 87-93 (one hundred twenty-five (125) pages).
U.S. Appl. No. 13/626,329, filed Sep. 25, 2012.
U.S. Appl. No. 13/626,282, filed Sep. 25, 2012.
Extended European Search Report dated Dec. 13, 2011 (seven (7) pages).
G. Ahern, Activation of TRPV1 by the Satiety Factor Oleoylethanolamide, The Journal of Biological Chemistry, vol. 278, No. 33, Aug. 15, 2003, pp. 30429-30434.
L.A. Birder et al., Altered urinary bladder function in mice lacking the vanilloid receptor TRPV1, Nature Neuroscience, vol. 5, No. 9, Sep. 2002, pp. 856-860.
E. Bodo et al., A Hot New Twist to Hair Biology: Involvement of Vanilloid Receptor-1 (VR1/TRPV1) Signaling in Human Hair Growth Control, American Journal of Pathology, vol. 166, No. 4, Apr. 2005, pp. 985-998.
D. Dawbarn et al., Intranigral Injection of Capsaicin Enhances Motor Activity and Depletes Nigral 5-Hydroxytryptamine But Not Substance P, Neuropharmacology, vol. 20, pp. 341-346, 1981.
P. Geppetti et al., Activation and sensitisation of the vanilloid receptor: role in gastrointestinal inflammation and function, British Journal of Pharmacology, 2004, vol. I 141, No. 8, pp. 1313-1320.
J. Ghilardi et al., Selective Blockade of the Capasicin Receptor TRPV1 Attenuates Bone Cancer Pain, The Journal of Neuroscience, Mar. 23, 2005, vol. 25, No. 12, pp. 3126-3131.

(Continued)

*Primary Examiner* — Zinna Northington Davis
(74) *Attorney, Agent, or Firm* — Crowell & Moring LLP

(57) ABSTRACT

The invention relates to aryl or N-heteroaryl substituted methanesulfonamide derivatives as vanilloid receptor ligands, to pharmaceutical compositions containing these compounds and also to these compounds for use in the treatment and/or prophylaxis of pain and further diseases and/or disorders.

15 Claims, No Drawings

(56) References Cited

OTHER PUBLICATIONS

P. Holzer, TRPV1 and the gut: from a tasty receptor for a painful vanilloid to a key player in hyperalgesia, European Journal of Pharmacology 500, 2004, pp. 231-241.

H. Rami et al., The therapeutic potential of TRPV1 (VRI) antagonists: clinical answers await, Drug Discover Today: Therapeutic Strategies, vol. 1, No. 1, 2004, pp. 97-104.

C. Maggi, Therapeutic Potential of Capsaicin-like Molecules: Studies in Animals and Humans, Life Sciences, vol. 51, 1992, pp. 1777-1781.

S. Marinelli et al., Presynaptic Facilitation of Glutamatergic Synapses to Dopaminergic Neurons of the Rat Substantia Nigra by Endogenous Stimulation of Vanilloid Receptors, The Journal of Neuroscience, Apr. 15, 2003, vol. 23, No. 8, pp. 3136-3144.

H. Pan et al., Sensing Tissue Ischemia: Another New Function for Capsaicin Receptors?, Circulation Journal of the American Heart Association, Circulation 2004, vol. 110, Issue 13, pp. 1826-1831.

H. Schultz, The spice of life is at the root of cardiac pain, Journal of Physiology (2003), 551.2, p. 400.

Y. Yiangou et al., Vanilloid receptor 1 immunoreactivity in inflamed human bowel, The Lancet, vol. 357, p. 1338-1339, Apr. 28, 2001.

M. Zahner et al., Cardiac vanilloid receptor 1-expressing afferent nerves and their role in the cardiogenic sympathetic reflex in rats, Journal of Physiology (2003) 551.2, pp. 515-523.

T. Sprenger et al., Migraine pathogenesis and state of pharmacological treatment options, BMC Medicine 2009, 7:71.

G.A. Lambert et al., The effects of the TRPV1 receptor antagonist SB-705498 on trigeminovascular sensitisation and neurotransmission, Nauyn-Schmied Arch Pharmacol (2009) vol. 380, pp. 311-325.

R. Planells-Cases et al., Functional aspects and mechanisms of TRPV1 involvement in neurogenic inflammation that leads to thermal hyperalgesia, Pflugers Arch—Eur J. Physiol (2005) vol. 451, pp. 151-159.

V. Micale et al., Altered responses of dopamine D3 receptor null mice to excitotoxic or anxiogenic stimuli: Possible involvement of the endocannabinoid and endovanilloid systems, Neurobiology of Disease 36 (2009), pp. 70-80.

M. Fu et al., TRPV1: A potential target for antiepileptogenesis, Medical Hypotheses 73 (2009), pp. 100-102.

F. Leung, Capsaicin-sensitive intestinal mucosal afferent mechanism and body fat distribution, Life Sciences 83 (2008), pp. 1-5.

A. Suri et al., The emerging role of TRPV1 in diabetes and obesity, Trends in Pharmacological Sciences, vol. 29, No. 1, pp. 29-36 (2007).

J. Li et al., Increased GFR and renal excretory function by activation of TRPV in the isolated prefused kidney, Pharmacological Research vol. 57, Issue 3 (2008), pp. 239-246.

M. Ghasemi et al., Effect of anandamide on nonadrenergic noncholinergic-mediated relaxation of rat corpus cavernosum, European Journal of Pharmacology vol. 544, Issues 1-3 (2006), pp. 138-145.

S. Mandadi et al., Locomotor Networks Are Targets of Modulation by Sensory Transient Receptor Potential Vanilloid 1 and Transient Receptor Potential Melastatin 8 Channels, Neuroscience 162 (2009) pp. 1377-1397.

R. Marsch et al., Reduced Anxiety, Conditioned Fear, and Hippocampal Long-Term Potentiation in Transient Receptor Potential Vanilloid Type 1 Receptor-Deficient Mice, The Journal of Neuroscience, Jan. 24, 2007, vol. 27, No. 4, pp. 832-839.

H. Eilers, Anesthetic Activation of Nociceptors: Adding Insult to Injury?, Molecular Interventions, Oct. 2008, vol. 8, Issue 5, pp. 226-229.

Won-Sik Shim et al., TRPV1 Mediates Histamine-Induced Itching via the Activation of Phospolipase $A_2$ and 12-Lipoxygenase, The Journal of Neuroscience, Feb. 28, 2007, vol. 27, No. 9, pp. 2331-2337.

W. Huang, Enhanced postmyocardial infarction fibrosis via stimulation of the transforming growth factor-B-Smad2 signaling pathway: role of transient receptor potential vanilloid type 1 channels, Journal of Hypertension vol. 27 (2009).

I. J. You et al., Society for Neuroscience, Abstract, Vo. 912.22 (2007).

J. Donnerer et al., Pharmacology, Feb. 2005; vol. 73, Issue 2, pp. 97-101 (2005) E. pub Oct. 18, 2004.

John J. Adcock, TRPV1 receptors in sensitization of cough and pain reflexes, Pulmonary Pharmacology & Therapeutics 22 (2009) 65-70.

Teshamae S. Monteith et al., Acute Migraine Therapy: New Drugs and New Approaches, Current Treatment in Neurology (2011) 13: 1-14.

Magdalene M. Moran et al., Transient receptor potential channels as therapeutic targets, Nature Review, Drug Discovery, vol. 10, Aug. 2011, pp. 601-620.

Celia D. Cruz et al., Intrathecal delivery of resiniferatoxin (RTX) reduces detrusor overactivity and spinal expression of TRPV1 in spinal cord injured animals, Experimental Neurology 214 (2008) 301-308.

Naoki Yoshimura et al., Therapeutic receptor targets for lower urinary tract dysfunction, Nauyn-Schmiedeberg's Arch Pharmacol (2008) 377:437-448.

Carols Silva et al., Bladder sensory densitization decreases urinary urgency, BMC Urology 2007, 7-9.

Klaus Urbahns et al., Naphthol derivatives as TRPV1 inhibitors for the treatment of urinary incontinence, Bioorganic & Medicinal Chemistry Letters 21 (2011) 3354-3357.

\* cited by examiner

ARYL OR N-HETEROARYL SUBSTITUTED METHANESULFONAMIDE DERIVATIVES AS VANILLOID RECEPTOR LIGANDS

CONTINUING DATA

This application claims priority from U.S. provisional patent application No. 61/539,181, filed Sep. 26, 2011, the entire disclosure of which is incorporated herein by reference. Priority is also claimed based on European patent application no. EP 11 007 807.8, filed Sep. 26, 2011, the entire disclosure of which is likewise incorporated herein by reference.

The invention relates to aryl or N-heteroaryl substituted methanesulfonamide derivatives as vanilloid receptor ligands, to pharmaceutical compositions containing these compounds and also to these compounds for use in the treatment and/or prophylaxis of pain and further diseases and/or disorders.

The treatment of pain, in particular of neuropathic pain, is very important in medicine. There is a worldwide demand for effective pain therapies. The urgent need for action for a patient-focused and target-oriented treatment of chronic and non-chronic states of pain, this being understood to mean the successful and satisfactory treatment of pain for the patient, is also documented in the large number of scientific studies which have recently appeared in the field of applied analgesics or basic research on nociception.

The subtype 1 vanilloid receptor (VR1/TRPV1), which is often also referred to as the capsaicin receptor, is a suitable starting point for the treatment of pain, in particular of pain selected from the group consisting of acute pain, chronic pain, neuropathic pain and visceral pain. This receptor is stimulated inter alia by vanilloids such as capsaicin, heat and protons and plays a central role in the formation of pain. In addition, it is important for a large number of further physiological and pathophysiological processes and is a suitable target for the therapy of a large number of further disorders such as, for example, migraine, depression, neurodegenerative diseases, cognitive disorders, states of anxiety, epilepsy, coughs, diarrhoea, pruritus, inflammations, disorders of the cardiovascular system, eating disorders, medication dependency, misuse of medication and urinary incontinence.

There is a demand for further compounds having comparable or better properties, not only with regard to affinity to vanilloid receptors 1 (VR1/TRPV1 receptors) per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example.

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by vanilloid receptors 1 (VR1/TRPV1 receptors).

This object is achieved by the subject matter described herein.

It has surprisingly been found that the substituted compounds of general formula (I), as given below, display outstanding affinity to the subtype 1 vanilloid receptor (VR1/TRPV1 receptor) and are therefore particularly suitable for the prophylaxis and/or treatment of disorders or diseases which are at least partially mediated by vanilloid receptors 1 (VR1/TRPV1).

The present invention therefore relates to a substituted compound of general formula (I)

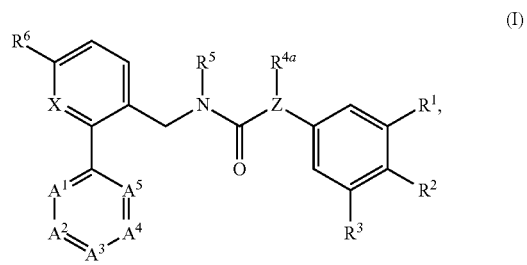

wherein
one of residues $R^1$ and $R^2$ denotes $CH_2$—$N(R^7)$—$S(=O)_2$—$R^8$,
   wherein $R^7$ represents H, $CH_3$ or $C_2H_5$, and
   wherein $R^8$ represents $NH_2$, $CH_3$ or $C_2H_5$,
and the respective remaining residue of $R^1$ and $R^2$ is selected from the group consisting of H, F, Cl, Br, I, $CH_3$, $CH_2$—OH, $CH_2$—$CH_2$—OH, $CH_2$—O—$CH_3$, $CH_2$—$CH_2$—O—$CH_3$, $CF_3$, OH, O—$CH_3$, O—$CH_2$—OH, O—$CH_2$—O—$CH_3$, O—$C_2H_5$, O—$C_2H_4$—OH, O—$C_2H_4$—O—$CH_3$ and $NH_2$;
$R^3$ is selected from the group consisting of H, F, Cl, Br, I, $CH_3$, $CF_3$, OH, O—$CH_3$, O—$CF_3$, and $NH_2$;
Z represents N or C—$R^{4b}$,
   wherein $R^{4b}$ represents H or $CH_3$;
$R^{4a}$ represents H or $CH_3$;
$R^5$ represents H or $CH_3$;
X represents N or CH;
$R^6$ represents $CF_3$, an unsubstituted, saturated $C_{1-4}$ aliphatic residue or an unsubstituted, saturated $C_{3-6}$ cycloaliphatic residue;
$A^1$ represents N or $CR^9$;
$A^2$ represents N or $CR^{10}$;
$A^3$ represents N or $CR^{11}$;
$A^4$ represents N or $CR^{12}$;
$A^5$ represents N or $CR^{13}$;
   with the proviso that 0, 1, 2 or 3 of variables $A^1, A^2, A^3, A^4$ and $A^5$ represent(s) a nitrogen atom, and
$R^9, R^{10}, R^{11}, R^{12}$, and $R^{13}$ each independently of one another represent H, F, Cl, Br, I, CN, $NO_2$, $CF_3$, $CF_2H$, $CFH_2$, OH, $OCF_3$, $NH_2$; a $C_{1-4}$ aliphatic residue, an O—$C_{1-4}$ aliphatic residue, a NH—$C_{1-4}$ aliphatic residue, and a $N(C_{1-4}$ aliphatic residue$)_2$, wherein the $C_{1-4}$ aliphatic residue can be in each case be unsubstituted or mono-, di- or trisubstituted with 1, 2 or 3 substituents selected independently of one another from the group consisting of OH, O—$CH_3$, O—$CH_2$—OH, O—$CH_2$—O—$CH_3$, O—$C_2H_5$, O—$C_2H_4$—OH, O—$C_2H_4$—O—$CH_3$, O—$CF_3$, $NH_2$, $NH(CH_3)$, and $N(CH_3)_2$; in which an "aliphatic residue" can be branched or unbranched, saturated or unsaturated, if not indicated otherwise;
optionally in the form of a single stereoisomer or a mixture of stereoisomers, in the form of the free compound and/or a physiologically acceptable salt thereof or in the form of a solvate, in particular a hydrate.

The term "single stereoisomer" comprises in the sense of this invention an individual enantiomer or diastereomer. The term "mixture of stereoisomers" comprises in the sense of this invention the racemate and mixtures of enantiomers and/or diastereomers in any mixing ratio.

The term "physiologically acceptable salt" comprises in the sense of this invention a salt of at least one compound according to the present invention and at least one physiologically acceptable acid or base.

The term "$C_{1-4}$ aliphatic residue" comprises in the sense of this invention acyclic saturated or unsaturated aliphatic hydrocarbon residues, which can be branched or unbranched and also unsubstituted or mono- or polysubstituted if not indicated otherwise, which contain 1 to 4 carbon atoms (i.e. 1, 2, 3 or 4 carbon atoms) respectively, i.e. $C_{1-4}$ alkanyls ($C_{1-4}$ alkyls), $C_{2-4}$ alkenyls and $C_{2-4}$ alkynyls, respectively. Alkenyls comprise at least one C—C double bond (a C=C-bond) and alkynyls comprise at least one C—C triple bond (a C≡C-bond). Preferably, aliphatic residues are selected from the group consisting of alkanyl (alkyl) and alkenyl residues, more preferably are alkanyl (alkyl) residues. Preferred $C_{1-4}$ alkanyl residues are selected from the group consisting of methyl, ethyl, n-propyl, 2-propyl, n-butyl, isobutyl, sec.-butyl, and tert.-butyl. Preferred $C_{2-4}$ alkenyl residues are selected from the group consisting of ethenyl (vinyl), propenyl (—$CH_2CH=CH_2$, —$CH=CH—CH_3$, —$C(=CH_2)$—$CH_3$) and butenyl. Preferred $C_{2-4}$ alkynyl residues are selected from the group consisting of ethynyl, propynyl (—$CH_2$—C≡CH, —C≡C—$CH_3$) and butynyl.

The term "$C_{3-6}$ cycloaliphatic residue" means for the purposes of this invention cyclic aliphatic hydrocarbons containing 3, 4, 5 or 6 carbon atoms, wherein the hydrocarbons in each case are saturated and unsubstituted. The cycloaliphatic residues can be bound to the respective superordinate general structure via any desired and possible ring member of the cycloaliphatic residue. Preferred $C_{3-6}$ cycloaliphatic residues are selected from the group consisting of cyclopropyl, cyclobutyl, cyclopentyl, and cyclohexyl. Particularly preferred $C_{3-6}$ cycloaliphatic residues are cyclopropyl and cyclobutyl, most preferred is cyclopropyl.

In relation to the term "aliphatic residue" the term "substituted" refers in the sense of this invention, with respect to said residue, to the single substitution (monosubstitution) or multiple substitution (polysubstitution), e.g. disubstitution or trisubstitution, of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of $CF_3$, $CH_2CF_3$, or at various points, as in the case of CH(OH)—CH=CH—$CHCl_2$. The multiple substitution can be carried out using the same or using different substituents.

Within the scope of the present invention, the symbol

used in the formulae denotes a link of a corresponding residue to the respective superordinate general structure.

If a residue occurs multiply within a molecule, then this residue can have respectively different meanings for various substituents: if, for example, both $R^9$ and $R^{10}$ denote a $C_{1-4}$ aliphatic residue, then the $C_{1-4}$ aliphatic residue can e.g. represent methyl for $R^9$ and can represent ethyl for $R^{10}$.

The terms "salt formed with a physiologically compatible acid" or "salt of physiologically acceptable acids" refers in the sense of this invention to salts of the respective active ingredient with inorganic or organic acids which are physiologically compatible—in particular when used in human beings and/or other mammals. Examples of physiologically acceptable acids are: hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred.

The terms "salt formed with a physiologically compatible base" or "salt of physiologically acceptable bases" refers in the sense of this invention to salts of the respective compound according to the invention—as an anion, e.g. upon deprotonation of a suitable functional group—with at least one cation or base—preferably with at least one inorganic cation—which are physiologically acceptable—in particular when used in human beings and/or other mammals. Particularly preferred are the salts of the alkali and alkaline earth metals, in particular (mono-) or (di)sodium, (mono-) or (di)potassium, magnesium or calcium salts, but also ammonium salts $[NH_xR_{4-x}]^+$, in which x=0, 1, 2, 3 or 4 and R represents a branched or unbranched $C_{1-4}$ aliphatic residue.

Further preferred embodiments of the compound according to the invention of general formula (I) have general formulae (I-a) and/or (I-b)

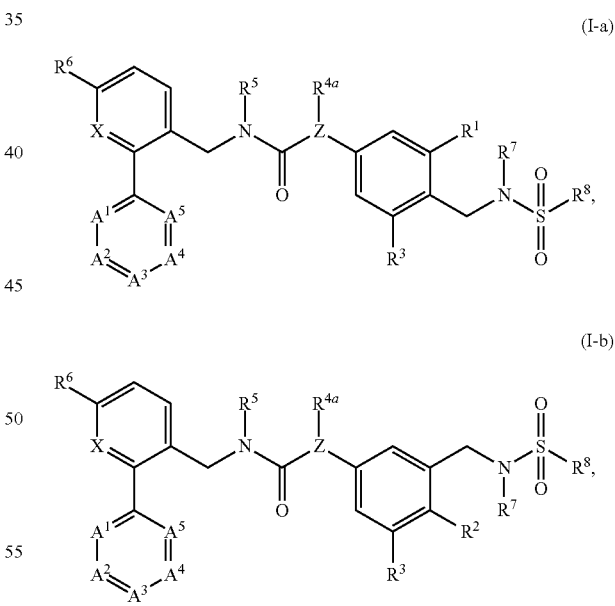

wherein the particular radicals and variables have the meanings described herein in connection with the compounds according to the invention and preferred embodiments thereof. More preferred is an inventive compound according to formula (I-a).

Particularly preferred embodiments of the compound of general formulae (I-a) and (I-b), respectively, have general formulae (I-a-1) and/or (I-b-1), respectively

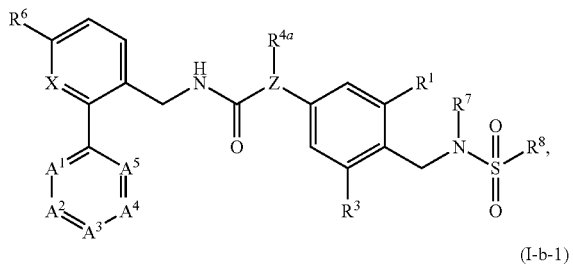
(I-a-1)

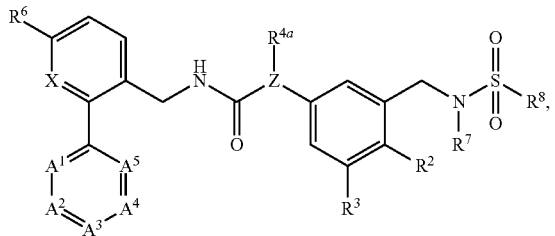
(I-b-1)

wherein the particular radicals and variables have the meanings described herein in connection with the compounds according to the invention and preferred embodiments thereof. Even more preferred is an inventive compound according to formula (I-a-1).

Particularly preferred embodiments of the compound of general formulae (I-a-1) and (I-b-1), respectively, have general formulae (I-a-1-a), (I-a-1-b), (I-b-1-a) and/or (I-b-1-b), respectively (I-a-1-a)

(I-b-1-a)

(I-a-1-b)

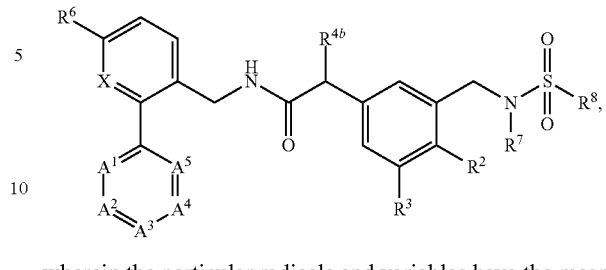
(I-b-1-b)

wherein the particular radicals and variables have the meanings described herein in connection with the compounds according to the invention and preferred embodiments thereof. Particularly preferred is an inventive compound according to formula (I-a-1-a) and/or (I-a-1-b), most preferred an inventive compound according to formula (I-a-1-b).

Another particularly preferred embodiment of the compound of general formulae (I-a-1-a) and (I-a-1-b), respectively, has general formulae (I-a-2-a), and/or (I-a-2-b), respectively

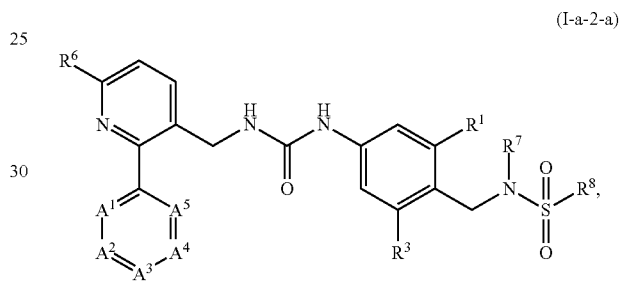
(I-a-2-a)

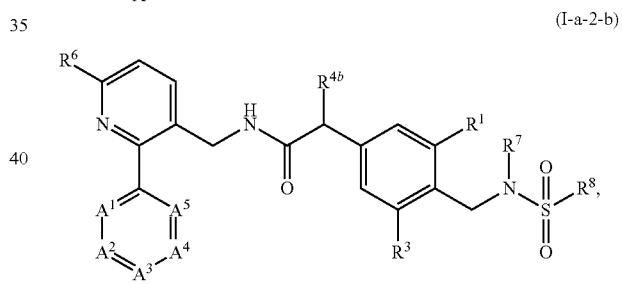
(I-a-2-b)

wherein the particular radicals and variables have the meanings described herein in connection with the compounds according to the invention and preferred embodiments thereof.

Yet another preferred embodiment of the compound according to the invention of general formula (I) has general formulae (I-c), (I-d), (I-c-1), (I-d-1), (I-c-2) and/or (I-c-3)

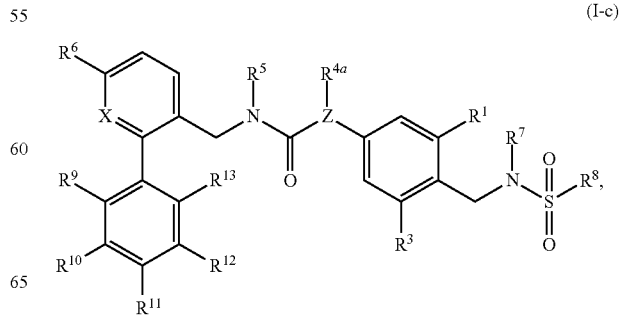
(I-c)

-continued (I-d)

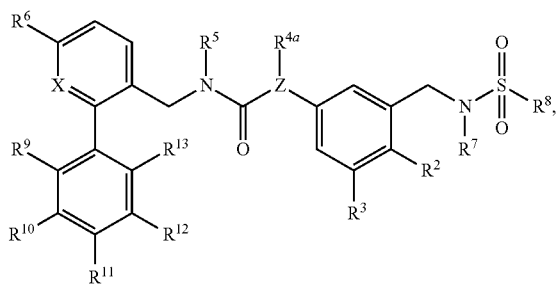

(I-c-1)

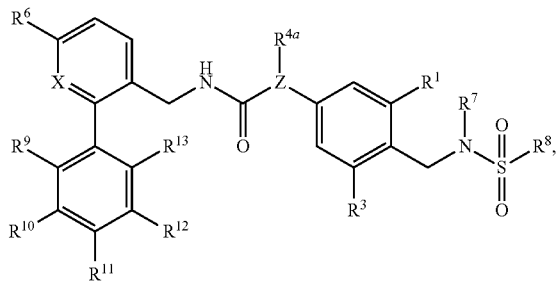

(I-d-1)

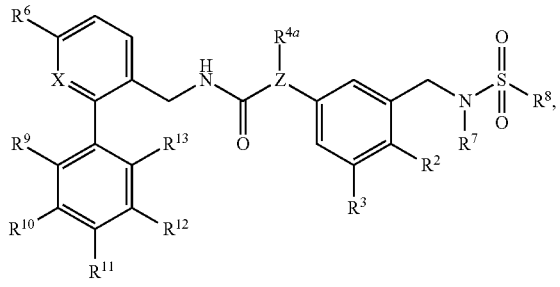

(I-c-2)

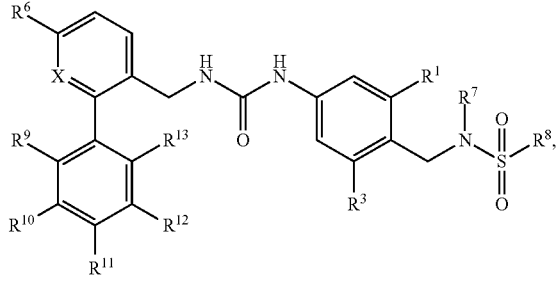

(I-c-3)

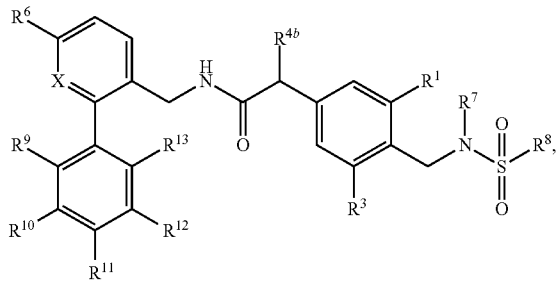

wherein the particular radicals and variables have the meanings described herein in connection with the compounds according to the invention and preferred embodiments thereof. Preferred is an inventive compound according to formula (I-c), (I-c-1), (I-c-2) and/or (I-c-3), particularly preferred according to formula (I-c-2) and/or (I-c-3), most preferred according to formula (I-c-3).

Still another preferred embodiment of the compound according to the invention of general formula (I) has one of the following general formulae:

(I-e)

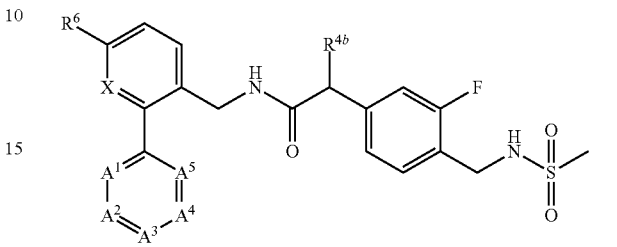

(I-f)

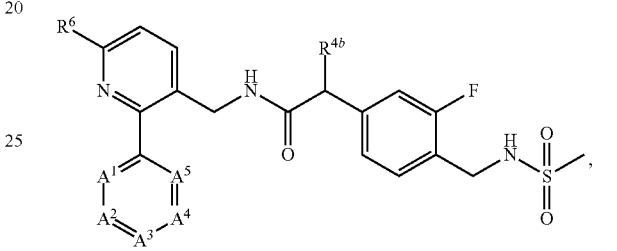

(I-e-1)

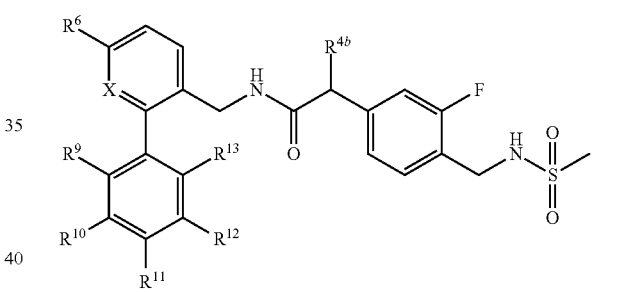

(I-f-1)

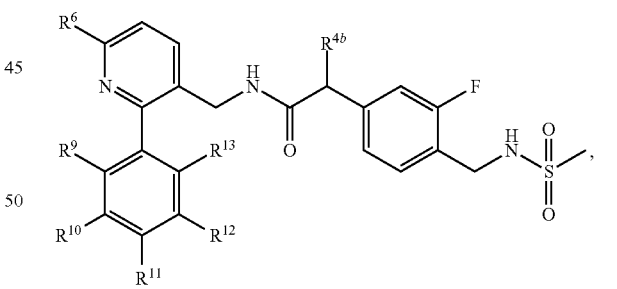

wherein the particular radicals and variables have the meanings described herein in connection with the compounds according to the invention and preferred embodiments thereof.

In a further preferred embodiment of the compound of general formula (I) according to the present invention
one of residues $R^1$ and $R^2$ denotes $CH_2$—$N(R^7)$—$S(=O)_2$—$R^8$,
wherein $R^7$ represents H, $CH_3$, or $C_2H_5$,
wherein $R^8$ represents $NH_2$, $CH_3$, or $C_2H_5$,
and the respective remaining residue of $R^1$ and $R^2$ is selected from the group consisting of H, F, Cl, Br, I, $CH_3$, $CH_2$—OH, $CH_2$—O—$CH_3$, $CF_3$, OH, and O—$CH_3$.

Preferably,
one of residues $R^1$ and $R^2$ denotes $CH_2—N(R^7)—S(=O)_2—R^8$,
  wherein $R^7$ represents H, $CH_3$, or $C_2H_5$,
  wherein $R^8$ represents $NH_2$, $CH_3$, or $C_2H_5$,
and the respective remaining residue of $R^1$ and $R^2$ is selected from the group consisting of H, F, Cl, Br, I, $CH_3$, $CF_3$, OH, and $O—CH_3$.

More preferably,
one of residues $R^1$ and $R^2$ denotes $CH_2—N(R^7)—S(=O)_2—R^8$,
  wherein $R^7$ represents H, $CH_3$, or $C_2H_5$,
  wherein $R^8$ represents $NH_2$, $CH_3$, or $C_2H_5$,
and the respective remaining residue of $R^1$ and $R^2$ is selected from the group consisting of H, F, Cl, $CH_3$, OH, and $O—CH_3$.

In another preferred embodiment of the compound of general formula (I) according to the present invention
$R^2$ denotes $CH_2—N(R^7)—S(=O)_2—R^8$,
  wherein $R^7$ represents H, $CH_3$, or $C_2H_5$,
  wherein $R^8$ represents $NH_2$, $CH_3$, or $C_2H_5$,
and $R^1$ is selected from the group consisting of H, F, Cl, Br, I, $CH_3$, $CH_2—OH$, $CH_2—O—CH_3$, $CF_3$, OH, and $O—CH_3$.

Preferably,
$R^2$ denotes $CH_2—N(R^7)—S(=O)_2—R^8$,
  wherein $R^7$ represents H, $CH_3$, or $C_2H_5$,
  wherein $R^8$ represents $NH_2$, $CH_3$, or $C_2H_5$,
and $R^1$ is selected from the group consisting of H, F, Cl, Br, I, $CH_3$, $CF_3$, OH, and $O—CH_3$.

More preferably,
$R^2$ denotes $CH_2—N(R^7)—S(=O)_2—R^8$,
  wherein $R^7$ represents H, $CH_3$, or $C_2H_5$,
  wherein $R^8$ represents $NH_2$, $CH_3$, or $C_2H_5$,
and $R^1$ is selected from the group consisting of H, F, Cl, $CH_3$, OH, and $O—CH_3$.

In yet another preferred embodiment of the compound of general formula (I) according to the present invention
$R^1$ denotes $CH_2—N(R^7)—S(=O)_2—R^8$,
  wherein $R^7$ represents H, $CH_3$, or $C_2H_5$,
  wherein $R^8$ represents $NH_2$, $CH_3$, or $C_2H_5$,
and $R^2$ is selected from the group consisting of H, F, Cl, Br, I, $CH_3$, $CH_2—OH$, $CH_2—O—CH_3$, $CF_3$, OH, and $O—CH_3$.

Preferably,
$R^1$ denotes $CH_2—N(R^7)—S(=O)_2—R^8$,
  wherein $R^7$ represents H, $CH_3$, or $C_2H_5$,
  wherein $R^8$ represents $NH_2$, $CH_3$, or $C_2H_5$,
and $R^2$ is selected from the group consisting of H, F, Cl, Br, I, $CH_3$, $CF_3$, OH, and $O—CH_3$.

More preferably,
$R^1$ denotes $CH_2—N(R^7)—S(=O)_2—R^8$,
  wherein $R^7$ represents H, $CH_3$, or $C_2H_5$,
  wherein $R^8$ represents $NH_2$, $CH_3$, or $C_2H_5$,
and $R^2$ is selected from the group consisting of H, F, Cl, $CH_3$, OH, and $O—CH_3$.

In a further preferred embodiment of the compound of general formula (I) according to the present invention
$R^3$ is selected from the group consisting of H, F, Cl, $CH_3$, $CF_3$, OH and $O—CH_3$.

Preferably,
$R^3$ is selected from the group consisting of H, F, Cl, $CH_3$, and $O—CH_3$.

More preferably,
$R^3$ is selected from the group consisting of H, F, and Cl, even more preferably denotes H or F, in particular H.

In another preferred embodiment of the compound of general formula (I) according to the present invention Z represents N and
$R^{4a}$ represents H, or
Z represents $C—R^{4b}$,
  wherein $R^{4b}$ represents H or $CH_3$, and
$R^{4a}$ represents H.

In yet another preferred embodiment of the compound of general formula (I) according to the present invention
Z represents N and
$R^{4a}$ represents H, or
Z represents $C—R^{4b}$,
  wherein $R^{4b}$ represents H, and
$R^{4a}$ represents H or $CH_3$.

In a further preferred embodiment of the compound of general formula (I) according to the present invention,
Z represents N and $R^{4a}$ represents H; or
Z represents $CR^{4b}$ and $R^{4a}$ and $R^{4b}$ each represent H; or
Z represents $CR^{4b}$ and $R^{4a}$ represents methyl and $R^{4b}$ represents H; or
Z represents $CR^{4b}$ and $R^{4a}$ represents H and $R^{4b}$ represents methyl.

In another preferred embodiment of the compound of general formula (I) according to the present invention
$R^5$ represents H.

In a further preferred embodiment of the compound of general formula (I) according to the present invention
X represents N.

In another preferred embodiment of the compound of general formula (I) according to the present invention
X represents CH.

In a further preferred embodiment of the compound of general formula (I) according to the present invention
$R^6$ represents $CF_3$, methyl, ethyl, 2-propyl, isobutyl, sec.-butyl, tert.-butyl, cyclopropyl, cyclobutyl or cyclopentyl.

Preferably,
$R^6$ represents $CF_3$, methyl, ethyl, 2-propyl, tert.-butyl, cyclopropyl, or cyclobutyl.

More preferably,
$R^6$ represents $CF_3$, tert.-Butyl or cyclopropyl.

In another preferred embodiment of the compound according to the invention of general formula (I) 0, 1 or 2 of variables $A^1, A^2, A^3, A^4$ and $A^5$ represent(s) a nitrogen atom, preferably 0 or 1 of variables $A^1, A^2, A^3, A^4$ and $A^5$ represent(s) a nitrogen atom, even more preferably none of variables $A^1, A^2, A^3, A^4$ and $A^5$ represents a nitrogen atom, i.e. $A^1$ denotes $C—R^9$, $A^2$ denotes $C—R^{10}$, $A^3$ denotes $C—R^{11}$, $A^4$ denotes $C—R^{12}$ and $A^5$ denotes $C—R^{13}$.

In another preferred embodiment of the compound according to the invention of general formula (I), the substructure (T1) of general formula (I)

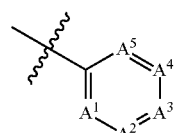

(T1)

represents one or more of the substructures (T1-a), (T1-b), (T1-c), (T1-d), (T1-e), (T1-f), (T1-g), (T1-h), (T1-i), (T1-j), (T1-k), (T1-m), (T1-n), (T1-o), (T1-p) and/or (T1-q), (T1-a) 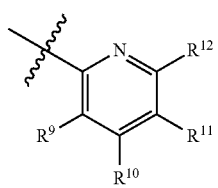

(T1-b) 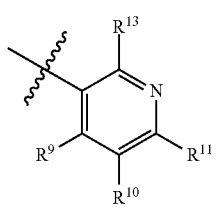

(T1-c) 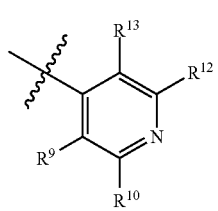

(T1-d) 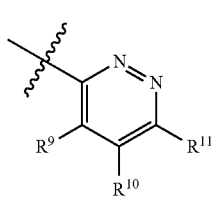

(T1-e) 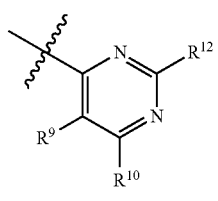

(T1-f) 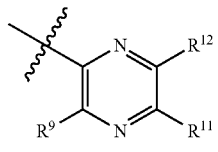

(T1-g) 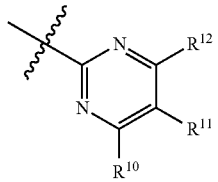

(T1-h) 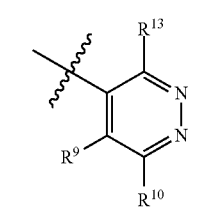

(T1-i) 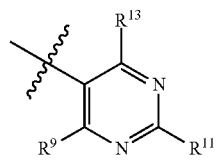

(T1-j) 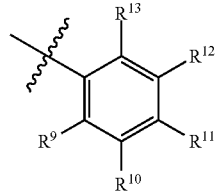

(T1-k) 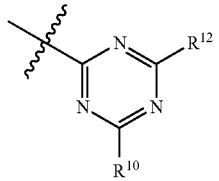

(T1-m) 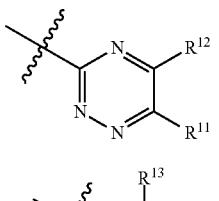

(T1-n) 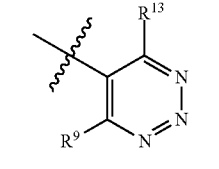

(T1-o) 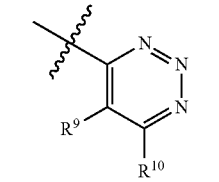

(T1-p) 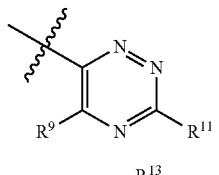

(T1-q) 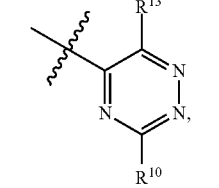

wherein the particular radicals $R^9$, $R^{10}$, $R^{11}$, $R^{12}$ and $R^{13}$ have the meanings described herein in connection with the compounds according to the invention and preferred embodiments thereof. Particularly preferred is a compound according to the invention of general formula (I), wherein the substructure (T1) represents (T1-a), (T1-b), (T1-c), (T1-d), (T1-e), (T1-f), (T1-g), (T1-h), (T1-i) and/or (T1-j), even more particularly preferred is a compound according to the invention of general formula (I), wherein the substructure (T1) represents (T1-a), (T1-b), (T1-c) and/or (T1-j). Most preferred is a compound, wherein (T1) represents (T1-j).

In another preferred embodiment of the compound according to the invention of general formula (I), at least one of radicals $R^9$, $R^{10}$, $R^{11}$, $R^{12}$ and $R^{13}$ is ≠H, preferably at least one of the two radicals $R^{10}$ and $R^{12}$ is ≠H, more preferably exactly one of the two radicals $R^{10}$ and $R^{12}$ is ≠H.

In another preferred embodiment of the compound according to the invention of general formula (I), at least one, preferably at least two, of the two radicals $R^9$, $R^{10}$, $R^{11}$, $R^{12}$ and $R^{13}$ is/are =H.

Preferably, at least one, preferably exactly one, of the two radicals $R^9$, $R^{11}$ and $R^{13}$ is/are =H.

In yet another preferred embodiment of the compound according to the invention of general formula (I), $R^9$, $R^{10}$, $R^{11}$, $R^{12}$, and $R^{13}$ each independently of one another represent H, F, Cl, Br, I, CN, $NO_2$, $CF_3$, $CF_2H$, $CFH_2$, OH, $OCF_3$, $NH_2$; a $C_{1-4}$ aliphatic residue, an O—$C_{1-4}$ aliphatic residue, a NH—$C_{1-4}$ aliphatic residue, and a N($C_{1-4}$ aliphatic residue)$_2$, wherein the $C_{1-4}$ aliphatic residue can be in each case be unsubstituted or mono-, di- or trisubstituted with 1, 2 or 3 substituents selected independently of one another from the group consisting of OH, O—$CH_3$, O—$CH_2$—OH, O—$CH_2$—O—$CH_3$, O—$C_2H_5$, O—$C_2H_4$—OH and O—$C_2H_4$—O—$CH_3$.

Preferably, $R^9$, $R^{10}$, $R^{11}$, $R^{12}$, and $R^{13}$ each independently of one another represent H, F, Cl, Br, I, CN, $NO_2$, $CF_3$, $CF_2H$, $CFH_2$, OH, $OCF_3$, $NH_2$, or a $C_{1-4}$ aliphatic residue, an O—$C_{1-4}$ aliphatic residue, a NH—$C_{1-4}$ aliphatic residue, or a N($C_{1-4}$ aliphatic residue)$_2$, wherein the $C_{1-4}$ aliphatic residue can be in each case be unsubstituted or mono-, di- or trisubstituted with 1, 2 or 3 substituents selected independently of one another from the group consisting of OH, O—$CH_3$, and O—$C_2H_5$.

More preferably, $R^9$, $R^{10}$, $R^{11}$, $R^{12}$, and $R^{13}$ each independently of one another represent H, F, Cl, Br, I, CN, $NO_2$, $CF_3$, $CF_2H$, $CFH_2$, OH, $OCF_3$, $NH_2$, or a $C_{1-4}$ aliphatic residue, an O—$C_{1-4}$ aliphatic residue, a NH—$C_{1-4}$ aliphatic residue, or a N($C_{1-4}$ aliphatic residue)$_2$, wherein the $C_{1-4}$ aliphatic residue can be in each case be unsubstituted or mono-, di- or trisubstituted with 1, 2 or 3 substituents selected independently of one another from the group consisting of OH and O—$CH_3$.

Even more preferably, $R^9$, $R^{10}$, $R^{11}$, $R^{12}$, and $R^{13}$ each independently of one another represent H, F, Cl, Br, I, CN, $NO_2$, $CF_3$, $CF_2H$, $CFH_2$, OH, $OCF_3$, $NH_2$, or methyl, ethyl, n-propyl, 2-propyl, n-butyl, isobutyl, sec.-butyl, tert.-butyl, $CH_2$—OH, $C_2H_4$—OH, $CH_2$—$OCH_3$, $C_2H_4$—$OCH_3$, $OCH_3$, O—$C_2H_5$, $NH(CH_3)$ or $N(CH_3)_2$.

Still more preferably, $R^9$, $R^{10}$, $R^{11}$, $R^{12}$, and $R^{13}$ each independently of one another are selected from the group consisting of H, F, Cl, Br, I, CN, $NO_2$, $CF_3$, $CF_2H$, $CFH_2$, OH, $OCF_3$, $NH_2$, or methyl, ethyl, 2-propyl, tert.-butyl, $CH_2$—OH, $CH_2$—$OCH_3$, $C_2H_4$—$OCH_3$, $OCH_3$, O—$C_2H_5$, $NH(CH_3)$ or $N(CH_3)_2$.

In another preferred embodiment of the compound according to the invention of general formula (I), at least one, preferably at least two, of $R^9$, $R^{10}$, $R^{11}$, $R^{12}$ and $R^{13}$ represent(s) H and the remaining respective residues of $R^9$, $R^{10}$, $R^{11}$, $R^{12}$, and $R^{13}$ each independently of one another represent H, F, Cl, Br, I, CN, $NO_2$, $CF_3$, $CF_2H$, $CFH_2$, OH, $OCF_3$, $NH_2$, methyl, ethyl, n-propyl, 2-propyl, n-butyl, isobutyl, sec.-butyl, tert.-butyl, $CH_2$—OH, $C_2H_4$—OH, $CH_2$—$OCH_3$, $C_2H_4$—$OCH_3$, $OCH_3$, O—$C_2H_5$, $NH(CH_3)$ or $N(CH_3)_2$, preferably each independently of one another represent H, F, Cl, Br, I, CN, $NO_2$, $CF_3$, $CF_2H$, $CFH_2$, OH, $OCF_3$, $NH_2$, methyl, ethyl, 2-propyl, tert.-butyl, $CH_2$—OH, $CH_2$—$OCH_3$, $C_2H_4$—$OCH_3$, $OCH_3$, O—$C_2H_5$, $NH(CH_3)$ or $N(CH_3)_2$.

In yet another preferred embodiment of the compound according to the invention of general formula (I), at least one of $R^9$, $R^{11}$ and $R^{13}$ represent(s) H, and the remaining respective residues of $R^9$, $R^{11}$ and $R^{13}$ each independently of one another represent H, F, Cl, Br, I, CN, $NO_2$, $CF_3$, $CF_2H$, $CFH_2$, OH, $OCF_3$, $NH_2$, methyl, ethyl, n-propyl, 2-propyl, n-butyl, isobutyl, sec.-butyl, tert.-butyl, $CH_2$—OH, $C_2H_4$—OH, $CH_2$—$OCH_3$, $C_2H_4$—$OCH_3$, $OCH_3$, O—$C_2H_5$, $NH(CH_3)$ or $N(CH_3)_2$, preferably each independently of one another represent H, F, Cl, Br, I, CN, $NO_2$, $CF_3$, $CF_2H$, $CFH_2$, OH, $OCF_3$, $NH_2$, methyl, ethyl, 2-propyl, tert.-butyl, $CH_2$—OH, $CH_2$—$OCH_3$, $C_2H_4$—$OCH_3$, $OCH_3$, O—$C_2H_5$, $NH(CH_3)$ or $N(CH_3)_2$, and at least one of radicals $R^{10}$ and $R^{12}$ represents F, Cl, Br, I, CN, $NO_2$, $CF_3$, $CF_2H$, $CFH_2$, OH, $OCF_3$, $NH_2$, methyl, ethyl, n-propyl, 2-propyl, n-butyl, isobutyl, sec.-butyl, tert.-butyl, $CH_2$—OH, $C_2H_4$—OH, $CH_2$—$OCH_3$, $C_2H_4$—$OCH_3$, $OCH_3$, O—$C_2H_5$, $NH(CH_3)$ or $N(CH_3)_2$, preferably each independently of one another represent H, F, Cl, Br, I, CN, $NO_2$, $CF_3$, $CF_2H$, $CFH_2$, OH, $OCF_3$, $NH_2$, methyl, ethyl, 2-propyl, tert.-butyl, $CH_2$—OH, $CH_2$—$OCH_3$, $C_2H_4$—$OCH_3$, $OCH_3$, O—$C_2H_5$, $NH(CH_3)$ or $N(CH_3)_2$, and the remaining respective residue of $R^{10}$ and $R^{12}$ represents H, F, Cl, Br, I, CN, $NO_2$, $CF_3$, $CF_2H$, $CFH_2$, OH, $OCF_3$, $NH_2$, methyl, ethyl, n-propyl, 2-propyl, n-butyl, isobutyl, sec.-butyl, tert.-butyl, $CH_2$—OH, $C_2H_4$—OH, $CH_2$—$OCH_3$, $C_2H_4$—$OCH_3$, $OCH_3$, O—$C_2H_5$, $NH(CH_3)$ or $N(CH_3)_2$, preferably each independently of one another represent H, F, Cl, Br, I, CN, $NO_2$, $CF_3$, $CF_2H$, $CFH_2$, OH, $OCF_3$, $NH_2$, methyl, ethyl, 2-propyl, tert.-butyl, $CH_2$—OH, $CH_2$—$OCH_3$, $C_2H_4$—$OCH_3$, $OCH_3$, O—$C_2H_5$, $NH(CH_3)$ or $N(CH_3)_2$.

In a further preferred embodiment of the compound according to the invention of general formula (I), $R^9$ represents H, F or Cl, $R^{10}$ represents H, F, Cl, CN or $CH_3$, $R^{11}$ represents H, F, Cl, CN, $CH_3$, O—$CH_3$ or O—$C_2H_5$, $R^{12}$ represents H, F, Cl, CN, $CF_3$, $CF_2H$, $CFH_2$, OH, $OCF_3$, $NH_2$, methyl, ethyl, 2-propyl, tert.-butyl, $CH_2$—OH, $CH_2$—$OCH_3$, $OCH_3$, O—$C_2H_5$, $NH(CH_3)$ or $N(CH_3)_2$, $R^{13}$ represents H, F, Cl, CN, $CH_3$, O—$CH_3$ or O—$C_2H_5$, preferably with the proviso that at least one of $R^9$, $R^{10}$, $R^{11}$, $R^{12}$ and $R^{13}$ is ≠H.

Particularly preferred is a compound according to general formula (I), wherein one of residues $R^1$ and $R^2$ denotes $CH_2$—$N(R^7)$—$S(=O)_2$—$R^8$, wherein $R^7$ represents H, $CH_3$, or $C_2H_5$, wherein $R^8$ represents $NH_2$, $CH_3$, or $C_2H_5$, and the respective remaining residue of $R^1$ and $R^2$ is selected from the group consisting of H, F, Cl, Br, I, $CH_3$, $CH_2$—OH, $CH_2$—O—$CH_3$, $CF_3$, OH, and O—$CH_3$, $R^3$ is selected from the group consisting of H, F, Cl, $CH_3$, and O—$CH_3$,
Z represents N and
$R^{4a}$ represents H, or
Z represents C—$R^{4b}$,
  wherein $R^{4b}$ represents H or $CH_3$, and
$R^{4a}$ represents H,
$R^5$ represents H,
X represents N or CH,
$R^6$ represents $CF_3$, tert.-Butyl or cyclopropyl,
$A^1$ represents N or $CR^9$;
$A^2$ represents N or $CR^{10}$;
$A^3$ represents N or $CR^{11}$;
$A^4$ represents N or $CR^{12}$;
$A^5$ represents N or $CR^{13}$;
  with the proviso that 0, 1 or 2 of variables $A^1, A^2, A^3, A^4$ and $A^5$ represent(s) a nitrogen atom, and
$R^9, R^{10}, R^{11}, R^{12}$, and $R^{13}$ each independently of one another represent
H, F, Cl, Br, I, CN, $NO_2$, $CF_3$, $CF_2H$, $CFH_2$, OH, $OCF_3$, $NH_2$, methyl, ethyl, n-propyl, 2-propyl, n-butyl, isobutyl, sec.-butyl, tert.-butyl, $CH_2$—OH, $C_2H_4$—OH, $CH_2$—$OCH_3$, $C_2H_4$—$OCH_3$, $OCH_3$, O—$C_2H_5$, $NH(CH_3)$ or $N(CH_3)_2$.

Even more particularly preferred is a compound according to general formula (I), wherein
one of residues $R^1$ and $R^2$ denotes $CH_2$—$N(R^7)$—$S(=O)_2$—$R^8$,
  wherein $R^7$ represents H, $CH_3$, or $C_2H_5$,
  wherein $R^8$ represents $NH_2$, $CH_3$, or $C_2H_5$,
and the respective remaining residue of $R^1$ and $R^2$ is selected from the group consisting of H, F, Cl, Br, I, $CH_3$, $CH_2$—OH, $CH_2$—O—$CH_3$, $CF_3$, OH, and O—$CH_3$,
$R^3$ is selected from the group consisting of H, F, Cl, $CH_3$, and O—$CH_3$,
Z represents N and
$R^{4a}$ represents H, or
Z represents C—$R^{4b}$,
  wherein $R^{4b}$ represents H or $CH_3$, and
$R^{4a}$ represents H,
$R^5$ represents H,
X represents N or CH,
$R^6$ represents $CF_3$, tert.-Butyl or cyclopropyl,
$A^1$ represents N or $CR^9$;
$A^2$ represents N or $CR^{10}$;
$A^3$ represents N or $CR^{11}$;
$A^4$ represents N or $CR^{12}$;
$A^5$ represents N or $CR^{13}$;
  with the proviso that 0, 1 or 2 of variables $A^1, A^2, A^3, A^4$ and $A^5$ represent(s) a nitrogen atom, and
$R^9$ represents H, F or Cl,
$R^{10}$ represents H, F, Cl, CN or $CH_3$,
$R^{11}$ represents H, F, Cl, CN, $CH_3$, O—$CH_3$ or O—$C_2H_5$,
$R^{12}$ represents H, F, Cl, CN, $CF_3$, $CF_2H$, $CFH_2$, OH, $OCF_3$, $NH_2$, methyl, ethyl, 2-propyl, tert.-butyl, $CH_2$—OH, $CH_2$—$OCH_3$, $OCH_3$, O—$C_2H_5$, $NH(CH_3)$ or $N(CH_3)_2$,
$R^{13}$ represents H, F, Cl, CN, $CH_3$, O—$CH_3$ or O—$C_2H_5$,
preferably with the proviso that at least one of $R^9, R^{10}, R^{11}, R^{12}$, and $R^{13}$ is ≠H.

Particularly preferred are compounds according to the invention from the group 1  2-(3-(methylsulfonamidomethyl)phenyl)-N-((2-m-tolyl-6-(trifluoromethyl)pyridin-3-yl)methyl)propanamide;
2  N-(4-(3-((2-m-tolyl-6-(trifluoromethyl)pyridin-3-yl)methyl)ureido)benzyl)methanesulfonamide;
3  2-(4-(methylsulfonamidomethyl)phenyl)-N-((2-m-tolyl-6-(trifluoromethyl)pyridin-3-yl)methyl)acetamide;
4  2-(4-(methylsulfonamidomethyl)phenyl)-N-((2-m-tolyl-6-(trifluoromethyl)pyridin-3-yl)methyl)propanamide;
5  2-(3-fluoro-4-(methylsulfonamidomethyl)phenyl)-N-((2-phenyl-6-(trifluoromethyl)pyridin-3-yl)methyl)propanamide;
6  2-(3-fluoro-4-(methylsulfonamidomethyl)phenyl)-N-((2-(2-fluorophenyl)-6-(trifluoromethyl)pyridin-3-yl)methyl)propanamide;
7  2-(3-fluoro-4-(methylsulfonamidomethyl)phenyl)-N-((2-(3-fluorophenyl)-6-(trifluoromethyl)pyridin-3-yl)methyl)propanamide;
8  2-(3-fluoro-4-(methylsulfonamidomethyl)phenyl)-N-((2-(4-fluorophenyl)-6-(trifluoromethyl)pyridin-3-yl)methyl)propanamide;
9  N-((2-(2,3-difluorophenyl)-6-(trifluoromethyl)pyridin-3-yl)methyl)-2-(3-fluoro-4-(methylsulfonamidomethyl)phenyl)propanamide;
10  N-((2-(3,4-difluorophenyl)-6-(trifluoromethyl)pyridin-3-yl)methyl)-2-(3-fluoro-4-(methylsulfonamidomethyl)phenyl)propanamide;
11  N-((2-(3,5-difluorophenyl)-6-(trifluoromethyl)pyridin-3-yl)methyl)-2-(3-fluoro-4-(methylsulfonamidomethyl)phenyl)propanamide;
12  N-((2-(2,5-difluorophenyl)-6-(trifluoromethyl)pyridin-3-yl)methyl)-2-(3-fluoro-4-(methylsulfonamidomethyl)phenyl)propanamide;
13  2-(3-fluoro-4-(methylsulfonamidomethyl)phenyl)-N-((2-(3-fluoro-4-methylphenyl)-6-(trifluoromethyl)pyridin-3-yl)methyl)propanamide;
14  2-(3-fluoro-4-(methylsulfonamidomethyl)phenyl)-N-((2-(3-fluoro-4-methoxyphenyl)-6-(trifluoromethyl)pyridin-3-yl)methyl)propanamide;
15  N-((2-(3-chlorophenyl)-6-(trifluoromethyl)pyridin-3-yl)methyl)-2-(3-fluoro-4-(methylsulfonamidomethyl)phenyl)propanamide;
16  N-((2-(3-chloro-4-fluorophenyl)-6-(trifluoromethyl)pyridin-3-yl)methyl)-2-(3-fluoro-4-(methylsulfonamidomethyl)phenyl)propanamide;
17  (S)—N-((2-(3-chloro-4-fluorophenyl)-6-(trifluoromethyl)pyridin-3-yl)methyl)-2-(3-fluoro-4-(methylsulfonamidomethyl)phenyl)propanamide;
18  (R)—N-((2-(3-chloro-4-fluorophenyl)-6-(trifluoromethyl)pyridin-3-yl)methyl)-2-(3-fluoro-4-(methylsulfonamidomethyl)phenyl)propanamide;
19  2-(3-fluoro-4-(methylsulfonamidomethyl)phenyl)-N-((2-o-tolyl-6-(trifluoromethyl)pyridin-3-yl)methyl)propanamide;
20  N-((6-cyclopropyl-2-m-tolylpyridin-3-yl)methyl)-2-(3-fluoro-4-(methylsulfonamidomethyl)phenyl)propanamide;
21  N-((5-tert-butyl-3'-methylbiphenyl-2-yl)methyl)-2-(3-fluoro-4-(methylsulfonamidomethyl)phenyl)propanamide;
22  2-(3-fluoro-4-(methylsulfonamidomethyl)phenyl)-N-((3'-methyl-5-(trifluoromethyl)biphenyl-2-yl)methyl)propanamide;
23  N-((6-tert-butyl-2-m-tolylpyridin-3-yl)methyl)-2-(3-fluoro-4-(methylsulfonamidomethyl)phenyl)propanamide;
24  2-(3-fluoro-4-(methylsulfonamidomethyl)phenyl)-N-((2-m-tolyl-6-(trifluoromethyl)pyridin-3-yl)methyl)propanamide;
25  (S)-2-(3-fluoro-4-(methylsulfonamidomethyl)phenyl)-N-((2-m-tolyl-6-(trifluoromethyl)pyridin-3-yl)methyl)propanamide;

26  (R)-2-(3-fluoro-4-(methylsulfonamidomethyl)phenyl)-N-((2-m-tolyl-6-(trifluoromethyl)pyridin-3-yl)methyl)propanamide;

27  N-(2-fluoro-4-(3-((2-m-tolyl-6-(trifluoromethyl)pyridin-3-yl)methyl)ureido)benzyl)methanesulfonamide;

28  2-(3-fluoro-4-(methylsulfonamidomethyl)phenyl)-N-((2-m-tolyl-6-(trifluoromethyl)pyridin-3-yl)methyl)acetamide;

29  2-(3-fluoro-4-(methylsulfonamidomethyl)phenyl)-N-((2-p-tolyl-6-(trifluoromethyl)pyridin-3-yl)methyl)propanamide;

30  N-((2-(2,3-dimethylphenyl)-6-(trifluoromethyl)pyridin-3-yl)methyl)-2-(3-fluoro-4-(methylsulfonamidomethyl)phenyl)propanamide;

31  N-((2-(3,4-dimethylphenyl)-6-(trifluoromethyl)pyridin-3-yl)methyl)-2-(3-fluoro-4-(methylsulfonamidomethyl)phenyl)propanamide;

32  N-((2-(3,5-dimethylphenyl)-6-(trifluoromethyl)pyridin-3-yl)methyl)-2-(3-fluoro-4-(methylsulfonamidomethyl)phenyl)propanamide;

33  N-((2-(2,5-dimethylphenyl)-6-(trifluoromethyl)pyridin-3-yl)methyl)-2-(3-fluoro-4-(methylsulfonamidomethyl)phenyl)propanamide;

34  N-((2-(2-fluoro-3-methylphenyl)-6-(trifluoromethyl)pyridin-3-yl)methyl)-2-(3-fluoro-4-(methylsulfonamidomethyl)phenyl)propanamide;

35  N-((2-(4-fluoro-3-methylphenyl)-6-(trifluoromethyl)pyridin-3-yl)methyl)-2-(3-fluoro-4-(methylsulfonamidomethyl)phenyl)propanamide;

36  2-(3-fluoro-4-(methylsulfonamidomethyl)phenyl)-N-((2-(3-fluoro-5-methylphenyl)-6-(trifluoromethyl)pyridin-3-yl)methyl)propanamide;

37  2-(3-fluoro-4-(methylsulfonamidomethyl)phenyl)-N-((2-(2-fluoro-5-methylphenyl)-6-(trifluoromethyl)pyridin-3-yl)methyl)propanamide;

38  N-((2-(2-cyano-3-methylphenyl)-6-(trifluoromethyl)pyridin-3-yl)methyl)-2-(3-fluoro-4-(methylsulfonamidomethyl)phenyl)propanamide;

39  N-((2-(4-cyano-3-methylphenyl)-6-(trifluoromethyl)pyridin-3-yl)methyl)-2-(3-fluoro-4-(methylsulfonamidomethyl)phenyl)propanamide;

40  N-((2-(3-cyano-5-methylphenyl)-6-(trifluoromethyl)pyridin-3-yl)methyl)-2-(3-fluoro-4-(methylsulfonamidomethyl)phenyl)propanamide;

41  N-((2-(2-cyano-5-methylphenyl)-6-(trifluoromethyl)pyridin-3-yl)methyl)-2-(3-fluoro-4-(methylsulfonamidomethyl)phenyl)propanamide;

42  2-(3-fluoro-4-(methylsulfonamidomethyl)phenyl)-N-((2-(2-methoxy-3-methylphenyl)-6-(trifluoromethyl)pyridin-3-yl)methyl)propanamide;

43  2-(3-fluoro-4-(methylsulfonamidomethyl)phenyl)-N-((2-(4-methoxy-3-methylphenyl)-6-(trifluoromethyl)pyridin-3-yl)methyl)propanamide;

44  2-(3-fluoro-4-(methylsulfonamidomethyl)phenyl)-N-((2-(3-methoxy-5-methylphenyl)-6-(trifluoromethyl)pyridin-3-yl)methyl)propanamide;

45  2-(3-fluoro-4-(methylsulfonamidomethyl)phenyl)-N-((2-(2-methoxy-5-methylphenyl)-6-(trifluoromethyl)pyridin-3-yl)methyl)propanamide;

46  N-((2-(4-ethoxy-3-methylphenyl)-6-(trifluoromethyl)pyridin-3-yl)methyl)-2-(3-fluoro-4-(methylsulfonamidomethyl)phenyl)propanamide;

47  N-((2-(3-ethoxy-5-methylphenyl)-6-(trifluoromethyl)pyridin-3-yl)methyl)-2-(3-fluoro-4-(methylsulfonamidomethyl)phenyl)propanamide;

48  N-((2-(2-ethoxy-5-methylphenyl)-6-(trifluoromethyl)pyridin-3-yl)methyl)-2-(3-fluoro-4-(methylsulfonamidomethyl)phenyl)propanamide;

49  2-(3-fluoro-4-(methylsulfonamidomethyl)phenyl)-N-((2-(3-(methoxymethyl)phenyl)-6-(trifluoromethyl)pyridin-3-yl)methyl)propanamide;

50  2-(3-fluoro-4-(methylsulfonamidomethyl)phenyl)-N-((2-(3-isopropylphenyl)-6-(trifluoromethyl)pyridin-3-yl)methyl)propanamide;

51  N-((2-(3-tert-butylphenyl)-6-(trifluoromethyl)pyridin-3-yl)methyl)-2-(3-fluoro-4-(methylsulfonamidomethyl)phenyl)propanamide;

52  N-((2-(3-(difluoromethyl)phenyl)-6-(trifluoromethyl)pyridin-3-yl)methyl)-2-(3-fluoro-4-(methylsulfonamidomethyl)phenyl)propanamide;

53  2-(3-fluoro-4-(methylsulfonamidomethyl)phenyl)-N-((6-(trifluoromethyl)-2-(3-(trifluoromethyl)phenyl)pyridin-3-yl)methyl)propanamide;

54  2-(3-fluoro-4-(methylsulfonamidomethyl)phenyl)-N-((2-(3-(trifluoromethoxy)phenyl)-6-(trifluoromethyl)pyridin-3-yl)methyl)propanamide;

55  N-((2-(3-(dimethylamino)phenyl)-6-(trifluoromethyl)pyridin-3-yl)methyl)-2-(3-fluoro-4-(methylsulfonamidomethyl)phenyl)propanamide;

56  N-((2-(2-cyanophenyl)-6-(trifluoromethyl)pyridin-3-yl)methyl)-2-(3-fluoro-4-(methylsulfonamidomethyl)phenyl)propanamide;

57  N-((2-(3-cyanophenyl)-6-(trifluoromethyl)pyridin-3-yl)methyl)-2-(3-fluoro-4-(methylsulfonamidomethyl)phenyl)propanamide;

58  N-((2-(4-cyanophenyl)-6-(trifluoromethyl)pyridin-3-yl)methyl)-2-(3-fluoro-4-(methylsulfonamidomethyl)phenyl)propanamide;

59  2-(3-fluoro-4-(methylsulfonamidomethyl)phenyl)-N-((2-(3-hydroxyphenyl)-6-(trifluoromethyl)pyridin-3-yl)methyl)propanamide;

60  2-(3-fluoro-4-(methylsulfonamidomethyl)phenyl)-N-((2-(2-methoxyphenyl)-6-(trifluoromethyl)pyridin-3-yl)methyl)propanamide;

61  2-(3-fluoro-4-(methylsulfonamidomethyl)phenyl)-N-((2-(3-methoxyphenyl)-6-(trifluoromethyl)pyridin-3-yl)methyl)propanamide;

62  2-(3-fluoro-4-(methylsulfonamidomethyl)phenyl)-N-((2-(4-methoxyphenyl)-6-(trifluoromethyl)pyridin-3-yl)methyl)propanamide;

63  N-((2-(2-ethoxyphenyl)-6-(trifluoromethyl)pyridin-3-yl)methyl)-2-(3-fluoro-4-(methylsulfonamidomethyl)phenyl)propanamide;

64  N-((2-(3-ethoxyphenyl)-6-(trifluoromethyl)pyridin-3-yl)methyl)-2-(3-fluoro-4-(methylsulfonamidomethyl)phenyl)propanamide;

65  N-((2-(4-ethoxyphenyl)-6-(trifluoromethyl)pyridin-3-yl)methyl)-2-(3-fluoro-4-(methylsulfonamidomethyl)phenyl)propanamide;

66  2-(3-fluoro-4-(methylsulfonamidomethyl)phenyl)-N-((6-(trifluoromethyl)-2,2'-bipyridin-3-yl)methyl)propanamide;

67  2-(3-fluoro-4-(methylsulfonamidomethyl)phenyl)-N-((6-(trifluoromethyl)-2,3'-bipyridin-3-yl)methyl)propanamide;

68  2-(3-fluoro-4-(methylsulfonamidomethyl)phenyl)-N-((6'-methoxy-6-(trifluoromethyl)-2,3'-bipyridin-3-yl)methyl)propanamide;

69  2-(3-fluoro-4-(methylsulfonamidomethyl)phenyl)-N-((5'-methoxy-6-(trifluoromethyl)-2,3'-bipyridin-3-yl)methyl)propanamide;

70  2-(3-fluoro-4-(methylsulfonamidomethyl)phenyl)-N-((4'-methoxy-6-(trifluoromethyl)-2,3'-bipyridin-3-yl)methyl)propanamide;
71  2-(3-fluoro-4-(methylsulfonamidomethyl)phenyl)-N-((2'-methyl-6-(trifluoromethyl)-2,3'-bipyridin-3-yl)methyl)propanamide;
72  2-(3-fluoro-4-(methylsulfonamidomethyl)phenyl)-N-((6'-methyl-6-(trifluoromethyl)-2,3'-bipyridin-3-yl)methyl)propanamide;
73  N-((5'-chloro-6-(trifluoromethyl)-2,3'-bipyridin-3-yl)methyl)-2-(3-fluoro-4-(methylsulfonamidomethyl)phenyl)propanamide;
74  N-((4'-chloro-6-(trifluoromethyl)-2,3'-bipyridin-3-yl)methyl)-2-(3-fluoro-4-(methylsulfonamidomethyl)phenyl)propanamide;
75  2-(3-fluoro-4-(methylsulfonamidomethyl)phenyl)-N-((2-(5-methylpyrazin-2-yl)-6-(trifluoromethyl)pyridin-3-yl)methyl)propanamide;
76  N-(2,6-difluoro-4-(3-((2-m-tolyl-6-(trifluoromethyl)pyridin-3-yl)methyl)ureido)benzyl)methanesulfonamide;
77  2-(3-chloro-4-(methylsulfonamidomethyl)phenyl)-N-((2-m-tolyl-6-(trifluoromethyl)pyridin-3-yl)methyl)propanamide;
78  2-(3-methoxy-4-(methylsulfonamidomethyl)phenyl)-N-((2-m-tolyl-6-(trifluoromethyl)pyridin-3-yl)methyl)propanamide;
79  N-(2-hydroxy-4-(3-((2-m-tolyl-6-(trifluoromethyl)pyridin-3-yl)methyl)ureido)benzyl)methanesulfonamide;
80  N-(2-methoxy-4-(3-((2-m-tolyl-6-(trifluoromethyl)pyridin-3-yl)methyl)ureido)benzyl)methanesulfonamide;
81  N-(2-methyl-4-(3-((2-m-tolyl-6-(trifluoromethyl)pyridin-3-yl)methyl)ureido)benzyl)methanesulfonamide;
82  N-(4-(3-((2-m-tolyl-6-(trifluoromethyl)pyridin-3-yl)methyl)ureido)benzyl)ethanesulfonamide;
83  2-(4-(ethylsulfonamidomethyl)-3-fluorophenyl)-N-((2-m-tolyl-6-(trifluoromethyl)pyridin-3-yl)methyl)propanamide;
84  1-{[2-m-tolyll-6-(trifluoromethyl)pyridin-3-yl]methyl}-3-{4-[(sulfamoylamino)methyl]phenyl}urea;
85  2-(3-fluoro-4-((sulfamoylamino)methyl)phenyl)-N-((2-m-tolyl-6-(trifluoromethyl)pyridin-3-yl)methyl)propanamide;
86  1-{3-fluoro-4-[(sulfamoylamino)methyl]phenyl}-3-{[2-m-tolyl-6-(trifluoromethyl)pyridin-3-yl]methyl}urea;
87  2-(3-fluoro-4-((N-methylmethylsulfonamido)methyl)phenyl)-N-((2-m-tolyl-6-(trifluoromethyl)pyridin-3-yl)methyl)propanamide;
88  2-(4-((sulfamoylamino)methyl)phenyl)-N-((2-m-tolyl-6-(trifluoromethyl)pyridin-3-yl)methyl)propanamide;
89  (S)-2-(4-((sulfamoylamino)methyl)phenyl)-N-((2-m-tolyl-6-(trifluoromethyl)pyridin-3-yl)methyl)propanamide;
90  (R)-2-(4-((sulfamoylamino)methyl)phenyl)-N-((2-m-tolyl-6-(trifluoromethyl)pyridin-3-yl)methyl)propanamide;
91  (S)-2-(3-fluoro-4-((sulfamoylamino)methyl)phenyl)-N-((2-m-tolyl-6-(trifluoromethyl)pyridin-3-yl)methyl)propanamide;
92  (R)-2-(3-fluoro-4-((sulfamoylamino)methyl)phenyl)-N-((2-m-tolyl-6-(trifluoromethyl)pyridin-3-yl)methyl)propanamide;
93  (S)—N-((2-(3-chlorophenyl)-6-(trifluoromethyl)pyridin-3-yl)methyl)-2-(3-fluoro-4-(methylsulfonamidomethyl)phenyl)propanamide;
94  (R)—N-((2-(3-chlorophenyl)-6-(trifluoromethyl)pyridin-3-yl)methyl)-2-(3-fluoro-4-(methylsulfonamidomethyl)phenyl)propanamide;
95  (S)-2-(3-fluoro-4-(methylsulfonamidomethyl)phenyl)-N-((2-(3-fluoro-4-methylphenyl)-6-(trifluoromethyl)pyridin-3-yl)methyl)propanamide;
96  (R)-2-(3-fluoro-4-(methylsulfonamidomethyl)phenyl)-N-((2-(3-fluoro-4-methylphenyl)-6-(trifluoromethyl)pyridin-3-yl)methyl)propanamide;
97  2-(3-methyl-4-(methylsulfonamidomethyl)phenyl)-N-((2-m-tolyl-6-(trifluoromethyl)pyridin-3-yl)methyl)propanamide;
98  N-((2-(3-chlorophenyl)-6-(trifluoromethyl)pyridin-3-yl)methyl)-2-(4-((sulfamoylamino)methyl)phenyl)propanamide;
99  N-((2-(3-methoxyphenyl)-6-(trifluoromethyl)pyridin-3-yl)methyl)-2-(4-((sulfamoylamino)methyl)phenyl)propanamide;
100 N-((2-(3-fluorophenyl)-6-(trifluoromethyl)pyridin-3-yl)methyl)-2-(4-((sulfamoylamino)methyl)phenyl)propanamide;
101 N-((2-(3-fluoro-4-methylphenyl)-6-(trifluoromethyl)pyridin-3-yl)methyl)-2-(4-((sulfamoylamino)methyl)phenyl)propanamide;
102 N-((2-(3-chlorophenyl)-6-(trifluoromethyl)pyridin-3-yl)methyl)-2-(3-fluoro-4-((sulfamoylamino)methyl)phenyl)propanamide;
103 2-(3-fluoro-4-((sulfamoylamino)methyl)phenyl)-N-((2-(3-methoxyphenyl)-6-(trifluoromethyl)pyridin-3-yl)methyl)propanamide;
104 2-(3-fluoro-4-((sulfamoylamino)methyl)phenyl)-N-((2-(3-fluorophenyl)-6-(trifluoromethyl)pyridin-3-yl)methyl)propanamide; and
105 2-(3-fluoro-4-((sulfamoylamino)methyl)phenyl)-N-((2-(3-fluoro-4-methylphenyl)-6-(trifluoromethyl)pyridin-3-yl)methyl)propanamide;

optionally in the form of a single stereoisomer or a mixture of stereoisomers, in the form of the free compound and/or a physiologically acceptable salt thereof.

Furthermore, preference may be given to compounds according to the invention that cause a 50 percent displacement of capsaicin, which is present at a concentration of 100 nM, in a FLIPR assay with CHO K1 cells which were transfected with the human VR1 gene at a concentration of less than 2,000 nM, preferably less than 1,000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA), as described hereinafter.

The substituted compounds according to the invention of the aforementioned general formula (I) and corresponding stereoisomers and also the respective corresponding acids, bases, salts and solvates are toxicologically safe and are therefore suitable as pharmaceutical active ingredients in pharmaceutical compositions.

The present invention therefore further relates to a pharmaceutical composition containing at least one compound according to the invention of the above-indicated formula (I), in each case if appropriate in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a corresponding salt, or respectively in the form of a corresponding solvate, and also if appropriate optionally one or more pharmaceutically compatible auxiliaries.

These pharmaceutical compositions according to the invention are suitable in particular for vanilloid receptor 1-(VR1/TRPV1) regulation, preferably for vanilloid receptor 1-(VR1/TRPV1) inhibition and/or for vanilloid receptor 1-(VR1/TRPV1) stimulation, i.e. they exert an agonistic or antagonistic effect.

Likewise, the pharmaceutical compositions according to the invention are preferably suitable for the prophylaxis and/or treatment of disorders or diseases which are mediated, at least in part, by vanilloid receptors 1.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of the above-indicated formula (I), if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragees, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention are prepared with the aid of conventional means, devices, methods and process known in the art, such as are described for example in "Remington's Pharmaceutical Sciences", A. R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

The pharmaceutical composition according to the invention is preferably suitable for the treatment and/or prophylaxis of one or more disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Particularly preferably, the pharmaceutical composition according to the invention is suitable for the treatment and/or prophylaxis of one or more disorders and/or diseases selected from the group consisting of pain, preferably of pain selected from the group consisting of acute pain, chronic pain, neuropathic pain, visceral pain and joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Most particularly preferably, the pharmaceutical composition according to the invention is suitable for the treatment and/or prophylaxis of pain, preferably of pain selected from the group consisting of acute pain, chronic pain, neuropathic pain and visceral pain.

The present invention further relates to a substituted compound according to general formula (I) and also if appropriate to a substituted compound according to general formula (I) and one or more pharmaceutically acceptable auxiliaries for use in vanilloid receptor 1-(VR1/TRPV1) regulation, preferably for use in vanilloid receptor 1-(VR1/TRPV1) inhibition and/or vanilloid receptor 1-(VR1/TRPV1) stimulation.

The present invention therefore further relates to a substituted compound according to general formula (I) and also if appropriate to a substituted compound according to general formula (I) and one or more pharmaceutically acceptable auxiliaries for use in the prophylaxis and/or treatment of disorders and/or diseases which are mediated, at least in part, by vanilloid receptors 1.

In particular, the present invention therefore further relates to a substituted compound according to general formula (I) and also if appropriate to a substituted compound according to general formula (I) and one or more pharmaceutically acceptable auxiliaries for use in the prophylaxis and/or treatment of disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particularly preferred is a substituted compound according to general formula (I) and also if appropriate to a substituted compound according to general formula (I) and one or more pharmaceutically acceptable auxiliaries for use in the prophylaxis and/or treatment of pain, preferably of pain selected from the group consisting of acute pain, chronic pain, neuropathic pain and visceral pain.

The present invention further relates to the use of at least one compound according to general formula (I) and also if appropriate of one or more pharmaceutically acceptable auxiliaries for the preparation of a pharmaceutical composition for vanilloid receptor 1-(VR1/TRPV1) regulation, preferably for vanilloid receptor 1-(VR1/TRPV1) inhibition and/or for vanilloid receptor 1-(VR1/TRPV1) stimulation, and, further for the prophylaxis and/or treatment of disorders and/or diseases which are mediated, at least in part, by vanilloid receptors 1, such as e.g. disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Another aspect of the present invention is a method for vanilloid receptor 1-(VR1/TRPV1) regulation, preferably for vanilloid receptor 1-(VR1/TRPV1) inhibition and/or for vanilloid receptor 1-(VR1/TRPV1) stimulation, and, further, a method of treatment and/or prophylaxis of disorders and/or diseases, which are mediated, at least in part, by vanilloid receptors 1, in a mammal, preferably of disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil, which comprises administering an effective amount of at least one compound of general formula (I) to the mammal.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74 79 (1941)) or by the formalin test (e.g. according to D. Dubuisson et al., Pain 1977, 4, 161-174).

The present invention further relates to processes for preparing inventive compounds of the above-indicated general formula (I).

All reactions which can be applied for synthesizing the compounds according to the present invention can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps of the reaction sequences which can be applied for synthesizing the compounds according to the present invention as well as the respective purification and/or isolation of intermediate or end products, can be carried out partly or completely under an inert gas atmosphere, preferably under a nitrogen atmosphere.

The substituted compounds according to the invention can be isolated both in the form of their free bases, their free acids and also in the form of corresponding salts, in particular physiologically compatible salts, i.e. physiologically acceptable salts.

The free bases of the respective substituted compounds according to the invention can be converted into the corresponding salts, preferably physiologically compatible salts, for example by reaction with an inorganic or organic acid, preferably with hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective substituted compounds of the aforementioned general formula (I) and of corresponding stereoisomers can likewise be converted into the corresponding physiologically compatible salts using the free acid or a salt of a sugar additive, such as for example saccharin, cyclamate or acesulphame.

Accordingly, the free acids of the substituted compounds according to the invention can be converted into the corresponding physiologically compatible salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ aliphatic residue.

The substituted compounds according to the invention and of corresponding stereoisomers can if appropriate, like the corresponding acids, the corresponding bases or salts of these compounds, also be obtained in the form of their solvates, preferably in the form of their hydrates, using conventional methods known to the person skilled in the art.

If the substituted compounds according to the invention are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulphonic acid, to be separated from one another.

The chemicals and reaction components used in the reactions and schemes described below are available commercially or in each case can be prepared by conventional methods known to the person skilled in the art.

The methods with which the person skilled in the art is familiar for carrying out the reaction steps for preparing the compounds according to the invention may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

The invention will be described hereinafter with the aid of a number of examples. This description is intended merely by way of example and does not limit the general idea of the invention

EXAMPLES

The indication "equivalents" ("eq." or "eq") means molar equivalents, "RT" or "rt" means room temperature (23±7° C.), "M" are indications of concentration in mol/l, "aq." means aqueous, "sat." means saturated, "sol." means solution, "conc." means concentrated.

Further abbreviations:
ACN acetonitrile
$BH_3.SMe_2$ borane-methyl sulfide complex
bipy 2,2'-bipyridine/2,2'-bipyridyl
Boc tert-butyloxycarbonyl
$Boc_2O$ di-tert-butyl dicarbonate
brine saturated aqueous sodium chloride solution
n-BuLi n-butyllithium
t-BuOH t-butanol
CC column chromatography on silica gel
d days
DCM dichloromethane
DETA diethylentriamine
DMAP 4-dimethylaminopyridine
DMF N,N-dimethylformamide
EDC N-(3-dimethylaminopropyl)-N'-ethylcarbodiimide
ether diethyl ether
EtOAc ethyl acetate
EtOH ethanol
h hour(s)
GC gas chromatography
$H_2O$ water
$H_2SO_4$ sulfuric acid
HOBt 1-hydroxybenzotriazole
m/z mass-to-charge ratio
MeOH methanol
min minutes
MS mass spectrometry
NaH sodium hydride
NBS N-bromosuccinimide
TEA triethylamine
$NiBr_2$ bipy complex of nickel(II) bromide and 2,2'-bipyridine
$NiCl_2.6H_2O$ nickel(II) chloride hexahydride
Pd/C palladium on charcoal
$Pd(PPh_3)_4$ tetrakis(triphenylphosphine)palladium(0)
TBTU O-(1H-benzotriazol-1-yl)-N,N,N',N'-tetramethyluronium tetrafluoroborate
TEA triethylamine
TFA trifluoroacetic acid
$Tf_2O$ triflic anhydride
TLC thin layer chromatography
THF tetrahydrofuran
v/v volume to volume
w/w weight in weight The yields of the compounds prepared were not optimized.
All temperatures are uncorrected.
All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCl, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The stationary phase used for the column chromatography was silica gel 60 (0.04-0.063 mm) from E. Merck, Darmstadt.

The mixing ratios of solvents or eluents for chromatography are specified in v/v.

All the intermediate products and exemplary compounds were analytically characterized by means of $^1$H-NMR spectroscopy. In addition, mass spectrometry tests (MS, m/z for $[M+H]^+$) were carried out for all the exemplary compounds and selected intermediate products.

Synthesis of the Exemplary Compounds:

The exemplary compounds 1-2, 4-27, 29-37, 39, 42-52, 55, 57-62, 64, 67-69, 71-73, 77-78, 80-86, 88, and 97 were obtained by one of the methods disclosed before and thereafter. The exemplary compounds 3, 28, 38, 40-41, 53-54, 56, 63, 65-66, 70, 74-76, 79, 87, 89-96 and 98-105 can be obtained by one of the methods disclosed before and thereafter. The person skilled in the art is aware which method has to be employed to obtain a particular exemplary compound.

Detailed Synthesis of Selected Exemplary Compounds

Synthesis of Example 1

2-(3-(methylsulfonamidomethyl)phenyl)-N-((2-m-tolyl-6-(trifluoromethyl)pyridin-3-yl)methyl)propanamide

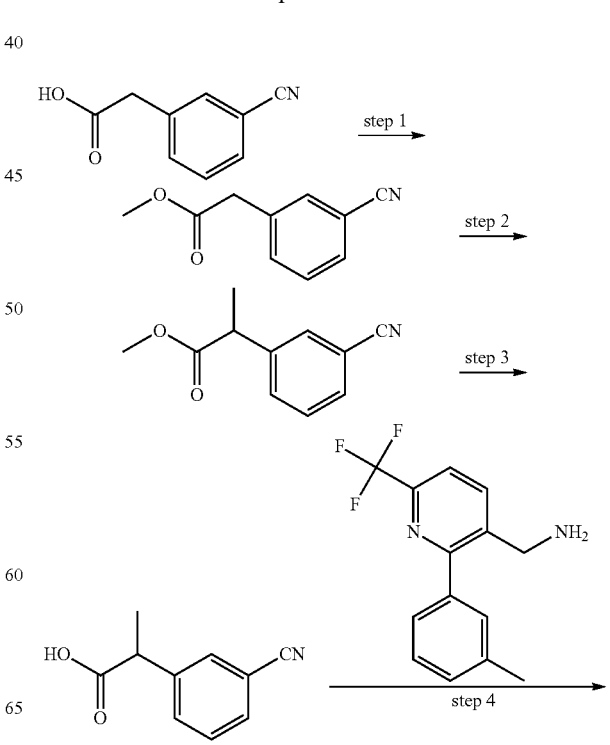

-continued

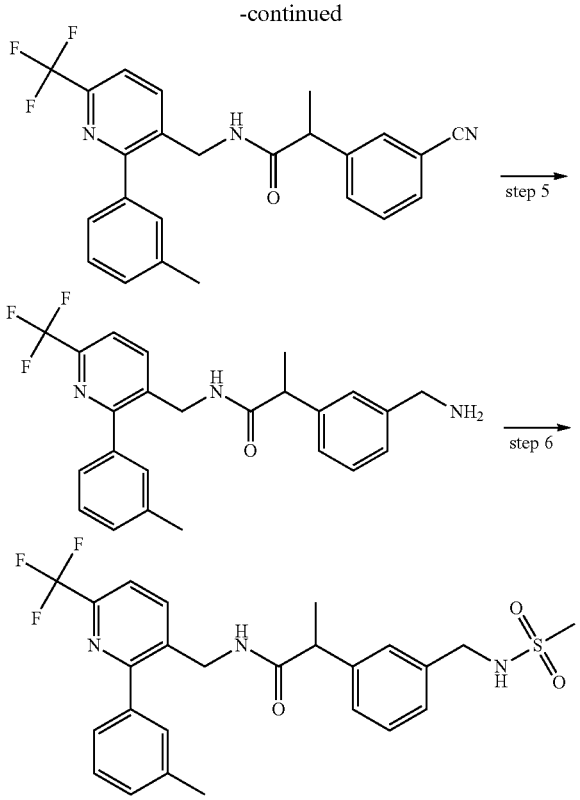

Step 1:

To the solution 2-(3-cyanophenyl)acetic acid (700 mg, 43.4 mmol) in methanol was slowly added sulfuric acid (0.42 mL, 4.34 mmol) at room temperature. The reaction mixture was refluxed for 3 h at 70° C. under nitrogen atmosphere. TLC showed complete consumption of starting material. The reaction mixture was cooled to room temperature. Solvent was removed in vacuo and extracted with ethyl acetate. The organic part was washed with brine and dried over anhydrous magnesium sulfate and concentrated under reduced pressure to afford crude product which was purified by column chromatography to afford methyl 2-(3-cyanophenyl)acetate (660 mg, 84%).

Step 2:

To the cooled solution of sodium hydride (91 mg, 2.285 mmol, 60% suspension in oil) in anhydrous tetrahydrofuran was added a solution of methyl 2-(3-cyanophenyl)acetate (400 mg, 2.285 mmol) dropwise at 0° C. Reaction mixture was stirred at room temperature for 1 h. TLC showed complete consumption of starting material. The reaction mixture was quenched with brine and extracted with ethyl acetate. The organic part was washed with brine and dried over anhydrous magnesium sulfate and concentrated under reduced pressure to afford crude product which was purified by column chromatography to afford methyl 2-(3-cyanophenyl)propanoate (180 mg, 48%).

Step 3:

A solution of methyl 2-(3-cyanophenyl)propanoate (180 mg, 9 mmol) in water/tetrahydrofuran (1:2, 30 mL) was treated with lithium hydroxide (27 mmol) at 0° C. and stirred for 2 h at room temperature. The mixture was diluted with water and dichloromethane, acidified with 1 N HCl solution and extracted with dichloromethane for several times. The combined organic layers were washed with water and brine, dried over magnesium sulfate and concentrated in vacuo which offered 2-(3-cyanophenyl)propanoic acid (147 mg, 88%).

Step 4:

A solution of 2-(3-cyanophenyl)propanoic acid (85 mg, 48.8 mmol) in 1,4-dioxane was cooled in an ice bath and 1-ethyl-3-(3-dimethylaminopropyl)carbodiimide (139 mg, 73.2 mmol), N-hydroxybenzotriazole (98 mg, 73.2 mmol), triethylamine (172 µl, 170 mmol) and (2-m-tolyl-6-(trifluoromethyl)pyridin-3-yl)methanamine (130 mg, 48.8 mmol), were added consecutively. The reaction mixture was stirred overnight at room temperature. Water was added to the reaction mixture and extracted with dichloromethane. The combined organic extracts were washed successively with saturated NaHCO₃ solution, 0.5 N HCl and then water and dried over magnesium sulfate. Evaporation of the solvent followed by column chromatographic purification afforded the 2-(3-cyanophenyl)-N-((2-m-tolyl-6-(trifluoromethyl)pyridin-3-yl)methyl)propanamide (110 mg, 53%).

Step 5:

To a stirred solution of 2-(3-cyanophenyl)-N-((2-m-tolyl-6-(trifluoromethyl)pyridin-3-yl)methyl)propanamide (217 mg, 5.13 mmol) in dry ethanol (15 mL), cooled to 0° C., were added nickel(II) chloride hexahydride (121 mg, 5.13 mmol). Sodium borohydride (136 mg, 35.9 mmol) was added in small portions over 10 min. The reaction mixture was allowed to warm to room temperature and left to stir for a further 1 h. The purple residue was dissolved in ethyl acetate (50 mL) and extracted with saturated NaHCO₃. The organic layer was dried over magnesium sulfate and the solvent removed in vacuo to yield 2-(3-(aminomethyl)phenyl)-N-((2-m-tolyl-6-(trifluoromethyl)pyridin-3-yl)methyl)propanamide (130 mg, 60%).

Step 6:

A cooled solution of 2-(3-(aminomethyl)phenyl)-N-((2-m-tolyl-6-(trifluoromethyl)pyridin-3-yl)methyl)propanamide (90 mg, 21 mmol) in dichloromethane was added triethylamine (45 µL, 42 mmol) at 0° C. The resulting solution was treated dropwise with methanesulfonyl chloride (24.4 µL, 31.6 mmol) over 10 min and stirred for 1 h at room temperature. After aqueous workup, the residue was purified by flash column chromatography to obtain 2-(3-(methylsulfonamidomethyl)phenyl)-N-((2-m-tolyl-6-(trifluoromethyl)pyridin-3-yl)methyl)propanamide (example 1) (67 mg, 60%).

¹H NMR (300 MHz, CD₃OD) δ 7.83 (d, 1H, J=8.1 Hz, Ar—H), 7.69 (d, 1H, J=8.1 Hz, Ar—H), 7.35-7.23 (m, 8H, Ar—H), 4.44 (q, 2H, Ar—CH₂), 4.23 (s, 2H, CH₂NHMs) 3.71 (q, 1H, CH—CH₃), 2.82 (s, 3H, NHSO₂CH₃), 2.39 (s, 3H, Ar—CH₃), 1.44 (d, 3H, —CH—CH₃).

Synthesis of Example 2

N-(4-(3-((2-m-tolyl-6-(trifluoromethyl)pyridin-3-yl)methyl)ureido)benzyl)methanesulfonamide

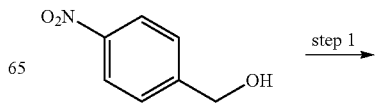

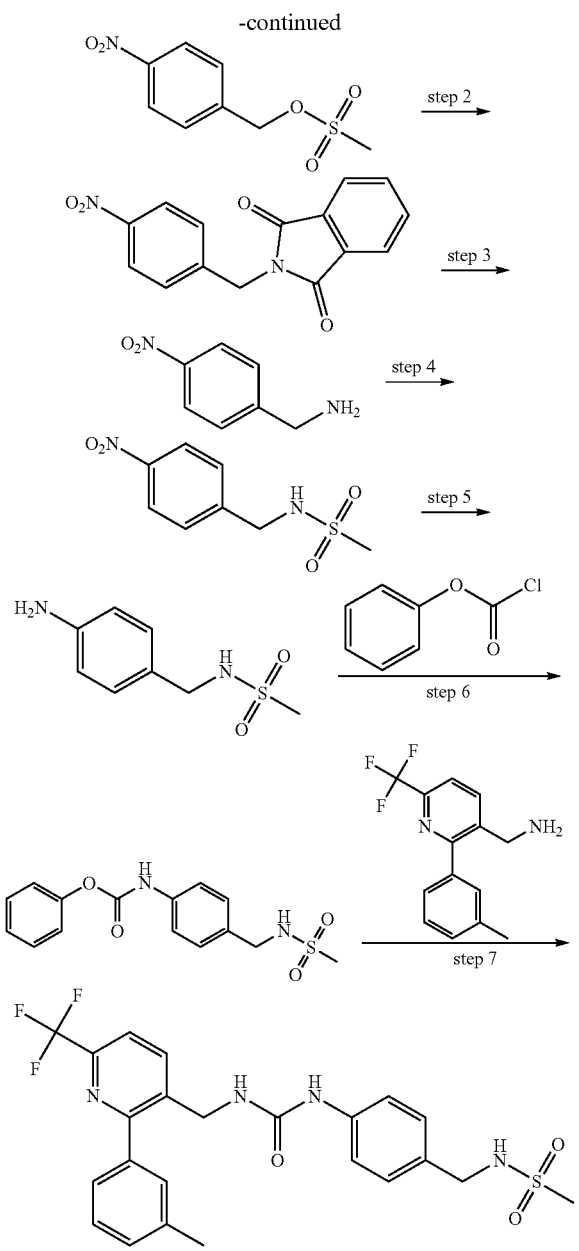

Step 1:

To a solution of (4-nitrophenyl)methanol (2 g, 13.06 mmol) in toluene (10 mL) was slowly added methane sulfonylchloride (1.21 mL, 15.67 mmol) at room temperature. The reaction mixture was heated to 80° C. for 4 h. TLC showed complete consumption of starting material. The reaction mixture was cooled to room temperature. The mixture was extracted with ethyl acetate and washed with water and brine. The extract was dried over magnesium sulfate and concentrated under reduced pressure. The crude was purified by column chromatography to give 4-nitrobenzyl methanesulfonate (2.2 g, 72%).

Step 2:

A solution of 4-nitrobenzyl methanesulfonate (2.2 g, 9.51 mmol) in dimethylformamide (10 mL) was added potassium phthalimide (1.9 g, 10.5 mmol) and stirred at room temperature for overnight. TLC showed complete consumption of starting material. The mixture was extracted with ethyl acetate and washed with water and brine. The extract was dried over magnesium sulfate and concentrated under reduced pressure. The crude was purified by crystallization to give 2-(4-nitrobenzyl)isoindoline-1,3-dione (1.6 g, 60%).

Step 3:

2-(4-Nitrobenzyl)isoindoline-1,3-dione (1.4 g, 4.96 mmol) was dissolved in tetrahydrofuran (8 mL). To the solution hydrazine monohydrate (1.48 mL, 19.84 mmol) and p-toluenesulfonic acid monohydrate (94 mg, 0.5 mmol) was added. It was refluxed for 6 h. TLC showed complete consumption of starting material. The mixture was extracted with ethyl acetate and washed with water and brine. The extract was dried over magnesium sulfate and concentrated under reduced pressure. The crude was purified by column chromatography to give (4-nitrophenyl)methanamine (651 mg, 86%).

Step 4:

(4-Nitrophenyl)methanamine (651 mg, 4.28 mmol) was dissolved in pyridine (4 mL).

The reaction mixture was added methane sulfonyl chloride (0.43 mL, 5.56 mmol) and stirred for 1 h at room temperature. TLC showed complete consumption of starting material. The mixture was diluted with 1N HCl and extracted with ethyl acetate. The extract was dried over magnesium sulfate and concentrated under reduced pressure. The crude was purified by column chromatography to give N-(4-nitrobenzyl)methanesulfonamide (881 mg, 89%).

Step 5:

N-(4-Nitrobenzyl)methanesulfonamide (881 mg, 3.83 mmol) was dissolved in methanol/tetrahydrofuran (1:1, 35 mL). 10% Pd/C (264 mg, 3 eq) was added to it. The resulting mixture was stirred at room temperature for overnight under $H_2$. TLC showed complete consumption of starting material. The mixture was filtered through celite bed and the filtrate was concentrated under reduced pressure. The crude was purified by column chromatography to give N-(4-aminobenzyl)methanesulfonamide (352 mg, 46%).

Step 6:

N-(4-Aminobenzyl)methanesulfonamide (352 mg, 1.76 mmol) was dissolved in acetonitrile (3 mL) and tetrahydrofuran (4 mL). The reaction mixture was added pyridine (0.17 mL, 2.11 mmol) and phenyl chloroformate (0.23 mL, 1.85 mmol) and stirred at room temperature for 3 h under nitrogen atmosphere. TLC showed complete consumption of starting material. The reaction mixture was diluted with water and extracted with ethyl acetate. The organic part was washed with water and brine. The organic layer was dried over magnesium sulfate and concentrated under reduced pressure. The crude was purified by column chromatography to give phenyl 4-(methylsulfonamidomethyl)phenylcarbamate (438 mg, 78%).

Step 7:

To a solution of phenyl 4-(methylsulfonamidomethyl)phenylcarbamate (59 mg, 0.18 mmol) acetonitrile (3 mL) was added 4-dimethylaminopyridine (23 mg, 0.18 mmol) and (2-m-tolyl-6-(trifluoromethyl)pyridin-3-yl)methanamine (49 mg, 0.18 mmol) at room temperature. The reaction mixture was heated to 50° C. for 16 h. TLC showed complete consumption of starting material. The reaction mixture was diluted with water and extracted with ethyl acetate. The organic part was washed with water and brine. The organic layer was dried over magnesium sulfate and concentrated under reduced pressure. The crude was purified by column chromatography to N-(4-(3-((2-m-tolyl-6-(trifluoromethyl)pyridin-3-yl)methyl)ureido)benzyl)methanesulfonamide (example 2) (57 mg, 63%).

$^1$H NMR (300 MHz, CD$_3$OD) δ 8.10 (d, 1H, J=7.50 Hz, Ar—H), 7.77 (d, 1H, J=8.07 Hz, Ar—H), 7.25-7.43 (m, 8H, Ar—H), 4.45 (s, 2H, Ar—CH$_2$), 4.17 (s, 2H, Ar—CH$_3$), 2.81 (s, 3H, Ms-CH$_3$), 2.43 (s, 4H, Ar—CH$_3$.

Exemplary compounds 76, 79 and 80 were prepared in a similar manner or may be prepared analogously according to example 2.

Synthesis of Example 4

2-(4-(methylsulfonamidomethyl)phenyl)-N-((2-m-tolyl-6-(trifluoromethyl)pyridin-3-yl)methyl)propanamide

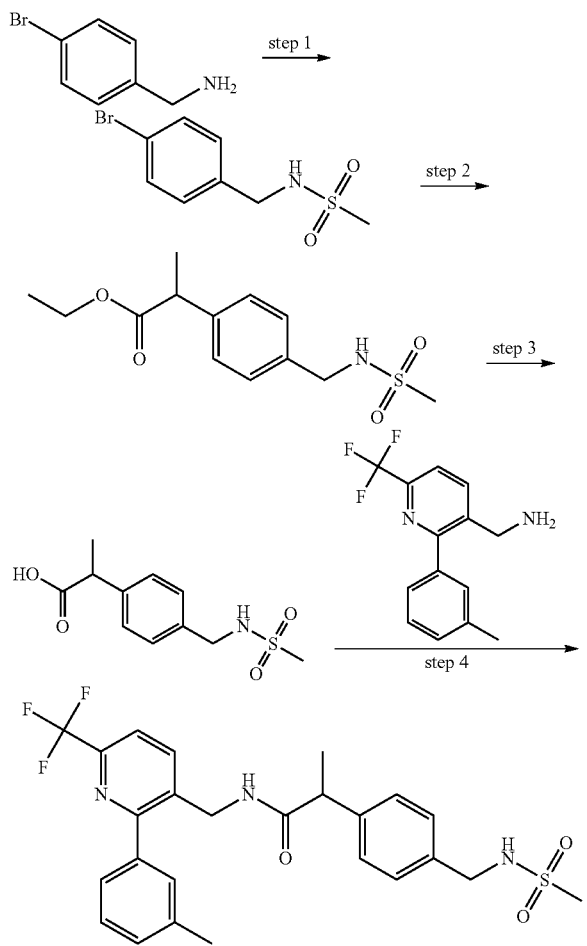

Step 1:
To a stirred solution of (4-bromophenyl)methanamine (500 mg, 2.687 mmol) in pyridine were added methanesulfonyl chloride (0.4 mL, 5.106 mmol) at 0° C. The reaction mixture was stirred for 1 h, then diluted with dichloromethane. The mixture was washed with water. The organic layer was dried over magnesium sulfate and filtered. The filtrate removed in vacuo. The crude was purified by column chromatography. N-(4-bromobenzyl)methane-sulfonamide (675 mg) was obtained in 95% yield.

Step 2:
To a stirred solution of N-(4-bromobenzyl)methane-sulfonamide (675 mg, 2.555 mmol) in dimethylformamide were added ethyl 2-chloropropionate (0.42 mL), manganese (280 mg) and (2,2'-bipyridine)nickel(II)-dibromide (67 mg, 0.17885 mmol). Trifluoroacetic acid (2 drops) was added. The reaction mixture was stirred for 36 h at 60° C. After cooling down to room temperature, the mixture was hydrolysed by 1N HCl and extracted with diethyl ether. The organic layer was dried over magnesium sulfate and filtered. The filtrate removed in vacuo. The crude was purified by column chromatography to obtain ethyl 2-(4-(methylsulfonamidomethyl)phenyl)propanoate (325 mg).

Step 3:
To a stirred solution of ethyl 2-(4-(methylsulfonamidomethyl)phenyl)propanoate (325 mg, 1.139 mmol) in co-solvent with tetrahydrofuran and water (1:1) were added sodium hydroxide (114 mg, 2.8475 mmol). The reaction mixture was refluxed for 16 h, then cooled to room temperature, acidified to pH 3-4 with acetic acid. The residue dissolved in ethyl acetate and washed with water and brine. The organic layer was dried over magnesium sulfate and filtered. The filtrate removed in vacuo. The crude was purified by column chromatography to give 2-(4-(methylsulfonamidomethyl)phenyl)propanoic acid (74 mg, 25%).

Step 4:
To a stirred solution of 2-(4-(methylsulfonamidomethyl)phenyl)propanoic acid (60 mg, 0.233 mmol) and (2-m-tolyl-6-(trifluoromethyl)pyridin-3-yl)methanamine (62 mg, 0.233 mmol) in acetonitrile were added N-(3-dimethylaminopropyl)-N'-ethylcarbodiimide (67 mg, 0.349 mmol), 1-hydroxybenzotriazole (47 mg, 0.349 mmol) and triethylamine (0.08 mL, 0.582 mmol). The reaction mixture was stirred for 15 h at room temperature. The residue dissolved in ethyl acetate and washed with water and brine. The organic layer was dried over magnesium sulfate and filtered. The filtrate removed in vacuo. The crude was purified by column chromatography to obtain 2-(4-(methylsulfonamidomethyl)phenyl)-N-((2-m-tolyl-6-(trifluoromethyl)pyridin-3-yl)methyl)propanamide (example 4) (81 mg, 69%).

$^1$H NMR (300 MHz, CDCl$_3$) 7.75 (d, 1H, J=8.07 Hz, Ar), 7.57 (d, 1H, J=8.07 Hz, Ar), 7.26 (m, 8H, Ar), 5.54 (t, 1H, NH), 4.63 (t, 1H, NH), 4.45 (d, 2H, CH$_2$), 4.30 (d, 2H, CH$_2$), 3.50 (q, 1H, CH), 2.91 (s, 3H, mesyl), 2.38 (s, 3H, methyl), 1.47 (d, 3H, methyl).

Synthesis of Example 5

2-(3-fluoro-4-(methylsulfonamidomethyl)phenyl)-N-((2-phenyl-6-(trifluoromethyl)pyridin-3-yl)methyl)propanamide

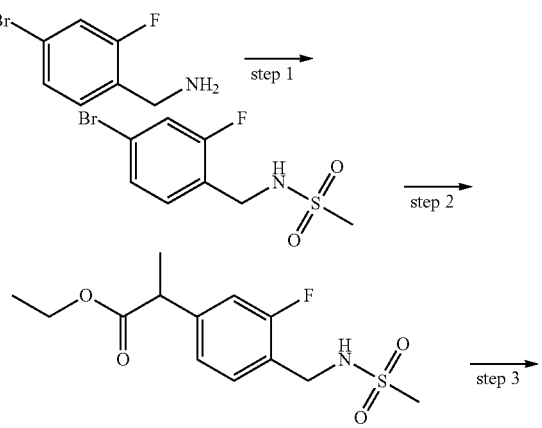

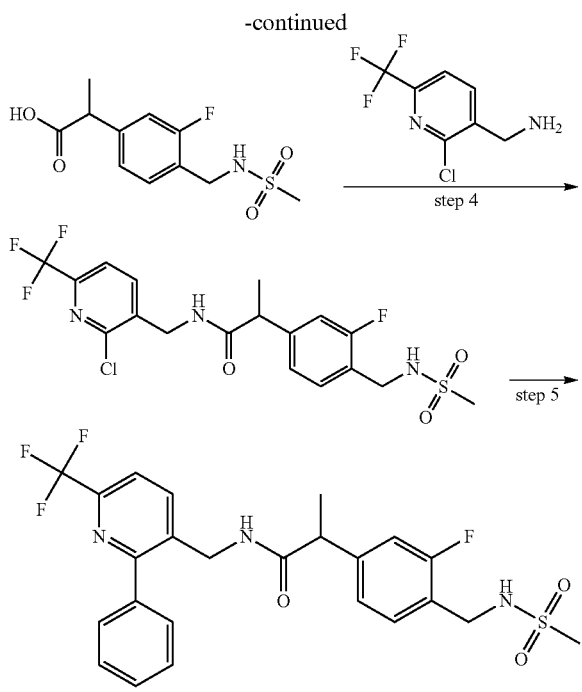

Step 1:

To a stirred solution of (4-bromo-2-fluorophenyl)methanamine (25 g, 122.5 mmol) in pyridine (100 mL) at 0° C. in a protective gas atmosphere was added methanesulfonyl chloride (14.22 mL, 183.8 mmol) slowly in portions. After addition, the suspension was stirred at 0° C. for 1 h. The reaction mixture was diluted with ice cold water (20 mL) and pH was adjusted to ~1 using 16% aqueous HCl solution. The resulting precipitation was filtered off, washed with ethyl acetate (3×20 mL) and dried overnight. The crude N-(4-bromo-2-fluorobenzyl)methanesulfonamide (29.24 g, 85%) was used as such without further purification.

Step 2:

N-(4-bromo-2-fluorobenzyl)methanesulfonamide (29 g, 102.8 mmol) and ethyl-2-chloropropionate (18.26 g, 133.6 mmol) were dissolved in dimethylformamide (155 mL) in a protective gas atmosphere at room temperature. Subsequently, manganese (11.29 g, 205.6 mmol), (2,2'-bipyridine) nickel(II) dibromide (2.69 g, 7.2 mmol) and trifluoroacetic acid (1.48 mL) were added and the mixture was stirred at 65° C. for 36 h. The reaction mixture was cooled to room temperature, hydrolysed using 1 N HCl (50 mL) and extracted with diethyl ether (4×100 mL). The combined organic layer were washed with water (40 mL) and brine solution (40 mL) and dried over magnesium sulfate. The solvent was evaporated under reduced pressure and the obtained residue was purified by column chromatography (eluent: diethyl ether/n-hexane 9:1) to afford ethyl 2-(3-fluoro-4-(methylsulfonamidomethyl)phenyl)propanoate (12.27 g, 39%).

Step 3:

The ethyl 2-(3-fluoro-4-(methylsulfonamidomethyl)phenyl)propanoate (12.5 g, 40.4 mmol) was dissolved in tetrahydrofuran-water mixture (120 mL, 2:1), lithium hydroxide (2.8 g, 121.1 mmol) was added and refluxing carried out for 12 h. After evaporation of the organic solvent under reduced pressure, the reaction mixture was extracted with diethyl ether (2×100 mL). The aqueous layer was acidified using 1 N HCl solution to pH=2 and extracted with dichloromethane (3×250 mL). The combined organic layer was dried over magnesium sulfate and concentrated under reduced pressure to afford 2-(3-fluoro-4-(methylsulfonamido-methyl)phenyl)propanoic acid (9.56 g, 86%).

Step 4:

To a stirred solution of (2-chloro-6-(trifluoromethyl)pyridin-3-yl)methanamine (2.9 g, 13.8 mmol) and 2-(3-fluoro-4-(methylsulfonamidomethyl)phenyl)propanoic acid (3.8 g, 13.8 mmol) in tetrahydrofuran (100 mL) were added 1-hydroxybenzotriazol (1.89 mL, 13.8 mmol), O-(1H-benzotriazol-1-yl)-N,N,N',N'-tetramethyluronium tetrafluoroborate (4.4 g, 13.8 mmol) and N-ethyldiisopropylamine (7 mL, 41.4 mmol) to gave an suspension. After addition of N,N-dimethylformamide (1 mL) the reaction mixture was stirred for 36 h at room temperature. The reaction mixture was concentrated under reduced pressure and the solid obtained was purified by column chromatography (silica gel: 100-200 mesh, eluent: cyclohexane/ethyl acetate 1:2) to afford N-((2-chloro-6-(trifluoromethyl)pyridin-3-yl)methyl)-2-(3-fluoro-4-(methylsulfonamidomethyl)phenyl)propanamide (3.96 g, 61%).

Step 5:

The N-((2-chloro-6-(trifluoromethyl)pyridin-3-yl)methyl)-2-(3-fluoro-4-(methylsulfonamidomethyl)phenyl)propanamide (100 mg, 0.214 mmol) was added to a mixture of 1.2 mL toluene-ethanol (8:2). After addition of (phenylboranediyl)dimethanol (39 mg, 0.324 mmol), 0.2 mL 2 M aqueous sodium carbonate solution and tetrakis(triphenylphosphine)palladium (0) (25 mg) the mixture was heated at 100° C. for 1 h in a microwave. The reaction mixture was free from oxygen by evacuating and flushing with nitrogen. After cooling to room temperature the reaction mixture was diluted with 15 mL water, extracted with ethyl acetate (2×15 mL), dried over magnesium sulfate and concentrated under reduced pressure. The solid obtained was purified by column chromatography (silica gel: 100-200 mesh, eluent: cyclohexane/ethyl acetate 2:3) to afford 2-(3-fluoro-4-(methylsulfonamidomethyl)phenyl)-N-((2-phenyl-6-(trifluoromethyl)pyridin-3-yl)methyl)propanamide (example 5) (92 mg, 84%).

Exemplary compounds 3, 6-14, 19, 28, 29-75 and 87 were prepared in a similar manner or may be prepared analogously according to example 5.

Synthesis of Example 16

N-((2-(3-chloro-4-fluorophenyl)-6-(trifluoromethyl)pyridin-3-yl)methyl)-2-(3-fluoro-4-(methylsulfonamidomethyl)phenyl)propanamide

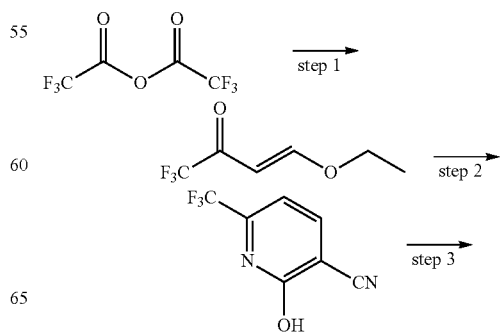

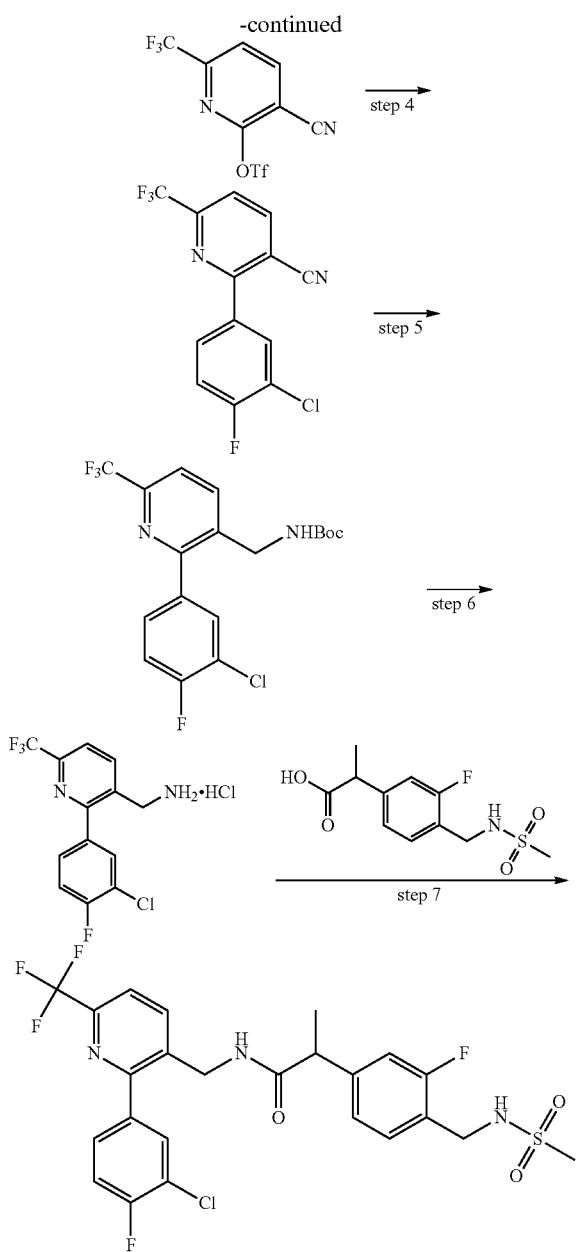

Step 1:

To a stirred solution of 4-dimethylaminopyridine (0.1 g, 1.0 mmol) and trifluoro acetic anhydride (23.2 g, 1.1 mol) in dichloromethane (75 mL), ethyl vinyl ether (7.5 g, 1 mol) was added dropwise at −10° C. The reaction mixture was stirred at 0° C. for 16 h and then allowed to warm at 25-30° C. TLC showed complete consumption of starting material. The organic layer was then washed with water (2×60 mL), saturated sodium bicarbonate solution (2×25 mL) and finally with brine (1×30 mL). The washed organic layer was dried over anhydrous magnesium sulfate and concentrated under reduced pressure to get a dark brown oily residue. This residue was finally distilled out to afford a colorless liquid compound (14.5 g, 82%).

Step 2:

To a solution of 1,4-dioxane (70 mL) and 2-cyanoacetamide (7.25 g, 0.086 mol), sodium hydride (4.12 g, 60%, 0.13 mol) was added portionwise at 10-15° C. It was allowed to stir for 30 min at ambient temperature after complete addition. A solution of (E)-4-ethoxy-1,1,1-trifluorobut-3-en-2-one (14.5 g, 0.086 mol) in 1,4-dioxane (70 mL) was added dropwise to this mixture. After complete addition the resulting solution was refluxed gently for 22 h. A solid was separated in the mixture. The mixture was cooled to ambient temperature and filtered through a sintered funnel. The residue was washed with 2 L of 1,4-dioxane. The washed solid was dissolved in water and acidified with 4N HCl (200 mL). The mixture was extracted with ethyl acetate (3×75 mL). The overall ethyl acetate layer was washed with brine (75 mL) and finally dried over magnesium sulfate. After removal of organic solvent under reduced pressure yellow solid was afforded (11 g, 68%).

Step 3:

A stirred solution of 2-hydroxy-6-(trifluoromethyl)nicotinonitrile (10 g, 53.19 mmol) in dichloromethane (50 mL) was cooled to 0-5° C. To this solution, triethylamine (11 mL, 79.78 mmol) was added and allowed to stir for 30 min at 0-5° C. Triflic anhydride (19 mL, 106.38 mmol) was added dropwise at 0-5° C. to the mixture and the mixture was stirred for 16 h at room temperature. TLC showed complete consumption of starting material. The reaction mixture was diluted with dichloromethane and the organic part was washed with water (2×250 mL). The washed organic layer was dried over anhydrous magnesium sulfate and concentrated under reduced pressure to afford the crude product and the crude product was purified by column chromatography (silica gel: 100-200; eluent: 10% ethyl acetate in n-hexane) to afford the pure 3-cyano-6-(trifluoromethyl)pyridin-2-yl trifluoromethanesulfonate (12.5 g, 73%).

Step 4:

In a 500 mL round bottomed flask, 3-cyano-6-(trifluoromethyl)pyridin-2-yl trifluoromethanesulfonate (12 g, 37.48 mmol) was dissolved in toluene (70 mL) and to it 4-fluoro-3-chloro boronic acid (7.48 g, 44.97 mmol), aqueous sodium carbonate solution (2M, 75 mL) and Pd(PPh$_3$)$_4$ (2.16 g, 1.87 mmol) was added and finally the system was flushed with nitrogen. Reaction mixture was heated to 100° C. and stirred at that temperature for 4 h. TLC showed complete consumption of starting material. The reaction mixture was cooled and was diluted with water (300 mL) and extracted with 20% ethyl acetate in n-hexane (2×200 mL). The combined organic layer was washed with water (200 mL) and brine (200 mL). It was dried over anhydrous magnesium sulfate and concentrated under reduced pressure. This crude compound was purified by column chromatography (silica gel: 100-200 mesh, eluent: 5% ethyl acetate in n-hexane) to afford 2-(3-chloro-4-fluorophenyl)-6-(trifluoromethyl)nicotinonitrile (9.2 g, 82%).

Step 5:

2-(3-Chloro-4-fluorophenyl)-6-(trifluoromethyl)nicotinonitrile (7.1 g, 23.66 mmol) was dissolved in dry tetrahydrofuran (70 mL), cooled and borane-dimethyl sulphide (3.41 mL, 35.44 mmol) was added to it under nitrogen atmosphere at 0-5° C. The reaction mixture was then refluxed for 20 h. Excess borane dimethyl sulphide was quenched with methanol (6 mL) under cold condition and then di-tert-butyl dicarbonate (10.86 mL, 47.32 mmol) was added to it and stirred for one hour at ambient temperature. TLC showed complete conversion of starting material. The organic volatiles were concentrated to obtain the crude compound, which was purified by column chromatography (silica gel: 100-200 mesh, eluent: 5% ethyl acetate in n-hexane) to afford a white solid (5.27 g, 55%).

Step 6:

To a stirred solution of tert-butyl (2-(3-chloro-4-fluorophenyl)-6-(trifluoromethyl)pyridin-3-yl)methylcarbamate (5.27 g, 13.04 mmol) in 1,4-dioxane (5 mL) was added with 1,4-dioxane.HCl (10 mL) under cooling and the reaction mixture was allowed to stir for 12 h. The reaction mixture was concentrated under reduced pressure and was co-distilled with methanol thrice and the solid obtained was filtered through sintered funnel and was washed with 10% ethyl acetate in n-hexane to afford pure (2-(3-chloro-4-fluorophenyl)-6-(trifluoromethyl)pyridin-3-yl)methanamine hydrochloride (4.14 g, 93%).

$^1$H NMR (DMSO-$d_6$, 400 MHz): δ 8.70 (s, 3H), 8.49 (d, 1H), 8.11 (d, 1H), 7.83 (d, 1H), 7.60 (t, 2H), 4.16 (s, 2H).

Step 7:

To a stirred solution of (2-(3-chloro-4-fluorophenyl)-6-(trifluoromethyl)pyridin-3-yl)methanamine hydrochloride (1.104 g, 3.632 mmol) and 2-(3-fluoro-4-(methylsulfonamidomethyl)phenyl)propanoic acid (1 g, 3.632 mmol) in tetrahydrofuran (28 mL) was added 1-hydroxybenzotriazolhydrate (0.49 mL, 3.632 mmol), O-(1H-benzotriazol-1-yl)-N,N,N',N'-tetramethyluronium tetrafluoroborate (1.166 g, 3.632 mmol) and N-ethyldiisopropylamine (1.852 mL, 10.896 mmol) and the reaction mixture was allowed to stir for 48 h. The reaction mixture was concentrated under reduced pressure and the solid obtained was purified by column chromatography (eluent:ethyl acetate/cyclohexane 2:1) to afford a white solid (example 16) (605 mg, 30%).

Synthesis of Examples 17 and 18

(S)—N-((2-(3-chloro-4-fluorophenyl)-6-(trifluoromethyl)pyridin-3-yl)methyl)-2-(3-fluoro-4-(methylsulfonamidomethyl)-phenyl)propanamide and (R)—N-((2-(3-chloro-4-fluorophenyl)-6-(trifluoromethyl)pyridin-3-yl)methyl)-2-(3-fluoro-4-(methylsulfonamidomethyl)phenyl)propanamide

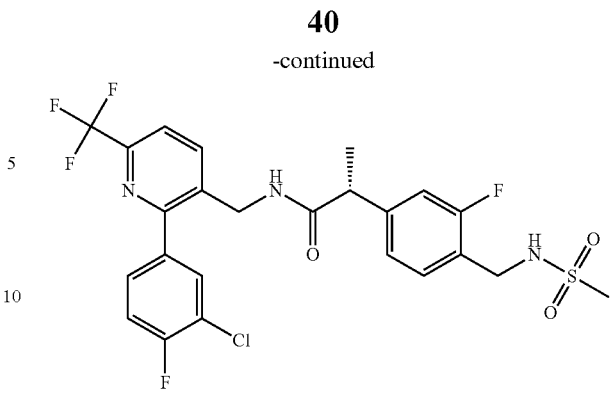

example 18

Enantioseparation:

N-((2-(3-Chloro-4-fluorophenyl)-6-(trifluoromethyl)pyridin-3-yl)methyl)-2-(3-fluoro-4-(methylsulfonamidomethyl)phenyl)propanamide (example 16) was separated by chiral high performance liquid chromatography (HPLC). HPLC enantioseparation was performed at a Chiralpak AD-H, 5 μM, 250×20 mm, detection by a JASCO UV-1575 wavelength UV monitor. The mobile phase were n-hexane/ethanol (7:3, v/v) with a flow rate 19 mL/min at 25° C. 300 mg of example 16 were separated by 20 separations each of 15 mg racemic mother compound. The eluent fractions corresponding to each chromatographic peaks were collected and evaporated in order to obtain enantiomerically pure fractions (S)—N-((2-(3-chloro-4-fluorophenyl)-6-(trifluoromethyl)pyridin-3-yl)methyl)-2-(3-fluoro-4-(methylsulfonamidomethyl)phenyl)propanamide (example 17) (143 mg) and (R)—N-((2-(3-chloro-4-fluorophenyl)-6-(trifluoromethyl)pyridin-3-yl)methyl)-2-(3-fluoro-4-(methylsulfonamidomethyl)phenyl)propanamide (example 18) (96 mg).

Synthesis of Example 20

N-((6-cyclopropyl-2-m-tolylpyridin-3-yl)methyl)-2-(3-fluoro-4-(methylsulfonamidomethyl)phenyl)propanamide

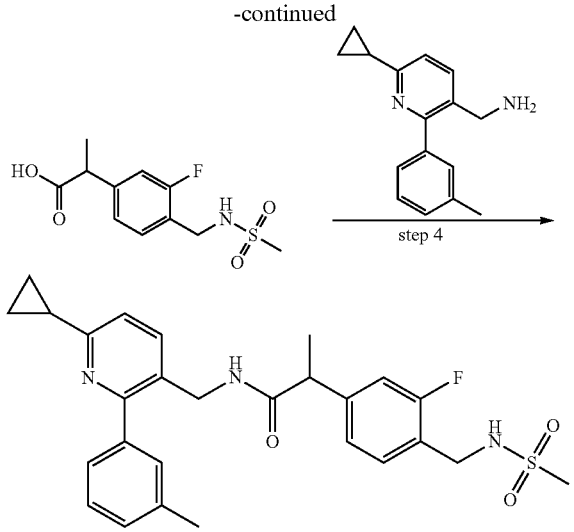

Step 1:

To a stirred solution of 4-bromo-2-fluorophenyl-methanamine (5.834 g, 28.592 mmol) in pyridine was added methanesulfonyl chloride (4.2 mL, 54.325 mmol) at 0° C. The reaction mixture was stirred for 1 h, then diluted with dichloromethane. The mixture was washed with water. The organic layer was dried over magnesium sulfate and filtered. The filtrate removed in vacuo. The crude was purified by column chromatography. N-(4-bromo-2-fluorobenzyl)methanesulfonamide (7.597 g) was obtained as 93% yield.

Step 2:

To a stirred solution of N-(4-bromo-2-fluorobenzyl)methanesulfonamide (2.94 g, 10.421 mmol) in dimethylformamide were added ethyl 2-chloropropionate (1.725 mL), manganese (1.145 g) and (2,2'-bipyridine)nickel(II)-dibromide (273 mg, mmol). 1-2 drops trifluoroacetic acid were added. The reaction mixture was stirred for 36 h at 60° C. After cooling down to room temperature, the mixture was hydrolysed by 1N HCl and extracted with diethyl ether. The organic layer was dried over magnesium sulfate and filtered. The filtrate removed in vacuo. The crude was purified by column chromatography. Ethyl 2-(3-fluoro-4-(methylsulfonamidomethyl)phenyl)propanoate (218 mg) was obtained.

Step 3:

To a stirred solution of ethyl 2-(3-fluoro-4-(methylsulfonamidomethyl)phenyl)propanoate (458 mg, 1.51 mmol) in co-solvent with tetrahydrofuran and water (1:1) were added lithium hydroxide (190 mg, 4.529 mmol). The reaction mixture was refluxed for 15 h, then cooled to room temperature, acidified to pH 3~4 with acetic acid. The residue dissolved in ethylacetate and washed with water and brine. The organic layer was dried over magnesium sulfate and filtered. The filtrate removed in vacuo. The crude was purified by column chromatography. 2-(3-Fluoro-4-(methylsulfonamidomethyl)phenyl)propanoic acid (218 mg) was obtained as 52% yield.

Step 4:

To a stirred solution of 2-(3-fluoro-4-(methylsulfonamidomethyl)phenyl)propanoic acid (41 mg, 0.148 mmol) and (6-cyclopropyl-2-m-tolylpyridin-3-yl)methanamine (35 mg, 0.148 mmol) in dioxane were added N-(3-dimethylaminopropyl)-N'-ethylcarbodiimide (43 mg, 0.222 mmol), 1-hydroxybenzotriazole (30 mg, 0.222 mmol) and triethylamine (0.05 mL, 0.37 mmol). The reaction mixture was stirred for 15 h at room temperature. The residue dissolved in ethylacetate and washed with water and brine. The organic layer was dried over magnesium sulfate and filtered. The filtrate removed in vacuo. The crude was purified by column chromatography. N-((6-cyclopropyl-2-m-tolylpyridin-3-yl)methyl)-2-(3-fluoro-4-(methylsulfonamidomethyl)phenyl)propanamide (example 20) (38 mg) was obtained as 52% yield.

$^1$H NMR (300 MHz, CDCl$_3$) 7.45 (d, J=8.07 Hz, 1H), 7.30-7.25 (m, 2H), 7.20-7.11 (m, 3H), 6.98-6.94 (m, 3H), 5.41 (t, 1H), 4.70 (t, 1H), 4.37 (dd, J=5.7 Hz, 2H), 4.34 (d, J=6.42 Hz, 2H), 3.41 (q, J=7.35 Hz, 1H), 2.87 (s, 3H), 2.37 (s, 3H), 2.08 (m, 1H), 1.42 (d, J=7.14 Hz, 3H), 0.88-0.83 (m, 6H).

Synthesis of Example 21

N-((5-tert-butyl-3'-methylbiphenyl-2-yl)methyl)-2-(3-fluoro-4-(methylsulfonamidomethyl)phenyl)propanamide

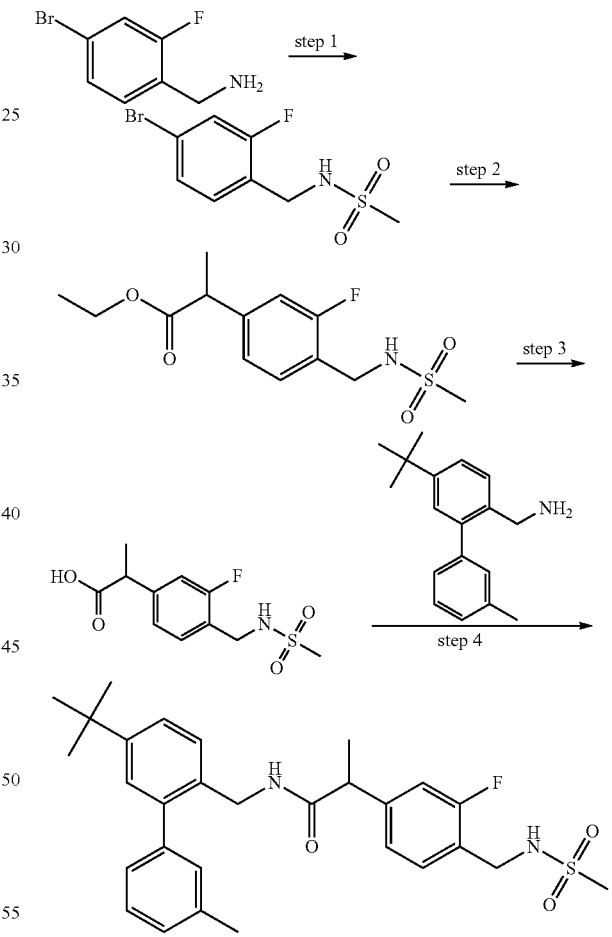

Step 1:

To a stirred solution of (4-bromo-2-fluorophenyl)methanamine (5.834 g, 28.592 mmol) in pyridine were added methanesulfonyl chloride (4.2 mL, 54.325 mmol) at 0° C. The reaction mixture was stirred for 1 h, then diluted with dichloromethane. The mixture was washed with water. The organic layer was dried over magnesium sulfate and filtered. The filtrate was removed in vacuo. The crude was purified by column chromatography to give N-(4-bromo-2-fluorobenzyl)methanesulfonamide (7.597 g, 93%).

Step 2:

To a stirred solution of N-(4-bromo-2-fluorobenzyl)methanesulfonamide (2.94 g, 10.421 mmol) in dimethylformamide were added ethyl 2-chloropropionate (1.725 mL), manganese (1.145 g) and (2,2'-bipyridine)nickel(II)-dibromide (273 mg, mmol). Trifluoroacetic acid (2 drops) was added. The reaction mixture was stirred for 36 h at 60° C. After cooling down to room temperature, the mixture was hydrolysed by 1N HCl and extracted with diethyl ether. The organic layer was dried over magnesium sulfate and filtered. The filtrate was removed in vacuo. The crude was purified by column chromatography to obtain ethyl 2-(3-fluoro-4-(methylsulfonamidomethyl)phenyl)propanoate (218 mg).

Step 3:

To a stirred solution of ethyl 2-(3-fluoro-4-(methylsulfonamidomethyl)phenyl)-propanoate (458 mg, 1.51 mmol) in co-solvent with tetrahydrofuran and water (1:1) were added lithium hydroxide (190 mg, 4.529 mmol). The reaction mixture was refluxed for 15 h, then cooled to room temperature, acidified to pH 3-4 with acetic acid. The residue dissolved in ethyl acetate and washed with water and brine. The organic layer was dried over magnesium sulfate and filtered. The filtrate was removed in vacuo. The crude was purified by column chromatography to give 2-(3-fluoro-4-(methylsulfonamidomethyl)phenyl)propanoic acid (218 mg, 52%).

Step 4:

To a stirred solution of 2-(3-fluoro-4-(methylsulfonamidomethyl)phenyl)propanoic acid (66 mg, 0.18 mmol) and (5-tert-butyl-3'-methylbiphenyl-2-yl)methanamine (113 mg, 0.119 mmol) in acetonitrile were added N-(3-dimethylaminopropyl)-N'-ethylcarbodiimide (52 mg, 0.270 mmol), 1-hydroxybenzotriazole (36 mg, 0.27 mmol) and triethylamine (0.063 mL, 0.45 mmol). The reaction mixture was stirred for 15 h at room temperature. The residue dissolved in ethyl acetate and washed with water and brine. The organic layer was dried over magnesium sulfate and filtered. The filtrate was removed in vacuo. The crude was purified by column chromatography. N-((5-tert-Butyl-3'-methylbiphenyl-2-yl)methyl)-2-(3-fluoro-4-(methylsulfonamidomethyl)phenyl)propanamide (example 21) (74 mg) was obtained as 81% yield.

$^1$H NMR (300 MHz, CD$_3$OD) 7.35 (m, 2H, Ar), 7.12 (m, 8H, Ar), 4.28 (s, 2H, CH2), 4.20 (s, 2H, CH$_2$), 3.61 (q, 1H), 2.85 (s, 3H, mesyl), 2.33 (s, 3H, methyl), 1.37 (d, 3H, J=7.14 Hz, methyl), 1.30 (s, 9H, t-Bu).

Synthesis of Example 22

2-(3-fluoro-4-(methylsulfonamidomethyl)phenyl)-N-((3'-methyl-5-(trifluoromethyl)biphenyl-2-yl)methyl)propanamide

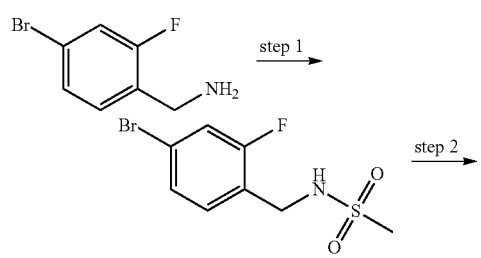

Step 1-3:

according to example 21.

Step 4:

To a stirred solution of 2-(3-fluoro-4-(methylsulfonamidomethyl)phenyl)propanoic acid (51 mg, 0.185 mmol) and (3'-methyl-5-(trifluoromethyl)biphenyl-2-yl)methanamine (60 mg, 0.222 mmol) in acetonitrile were added N-(3-dimethylaminopropyl)-N'-ethylcarbodiimide (53 mg, 0.2775 mmol), 1-hydroxybenzotriazole (38 mg, 0.270 mmol) and triethylamine (0.06 mL, 0.4625 mmol). The reaction mixture was stirred for 15 h at room temperature. The residue dissolved in ethyl acetate and washed with water and brine. The organic layer was dried over magnesium sulfate and filtered. The filtrate removed in vacuo. The crude was purified by column chromatography. 2-(3-Fluoro-4-(methylsulfonamidomethyl)phenyl)-N-((3'-methyl-5-(trifluoromethyl)biphenyl-2-yl)methyl)propanamide (example 22) (81 mg) was obtained as 84% yield.

$^1$H NMR (300 MHz, CD$_3$OD) 7.55 (d, 1H, J=7.86 Hz, Ar), 7.38 (m, 3H, Ar), 7.29 (t, 1H, Ar), 7.2 (d, 1H, J=7.14 Hz, Ar), 7.1 (m, 4H, Ar), 4.29 (d, 4H), 3.64 (q, 1H, CH), 2.85 (s, 3H, mesyl), 2.36 (s, 3H, methyl), 1.39 (d, 3H, J=6.96 Hz).

Synthesis of Example 23

N-((6-tert-butyl-2-m-tolylpyridin-3-yl)methyl)-2-(3-fluoro-4-(methylsulfonamidomethyl)phenyl)propanamide

45

-continued

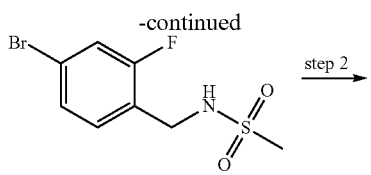

step 2

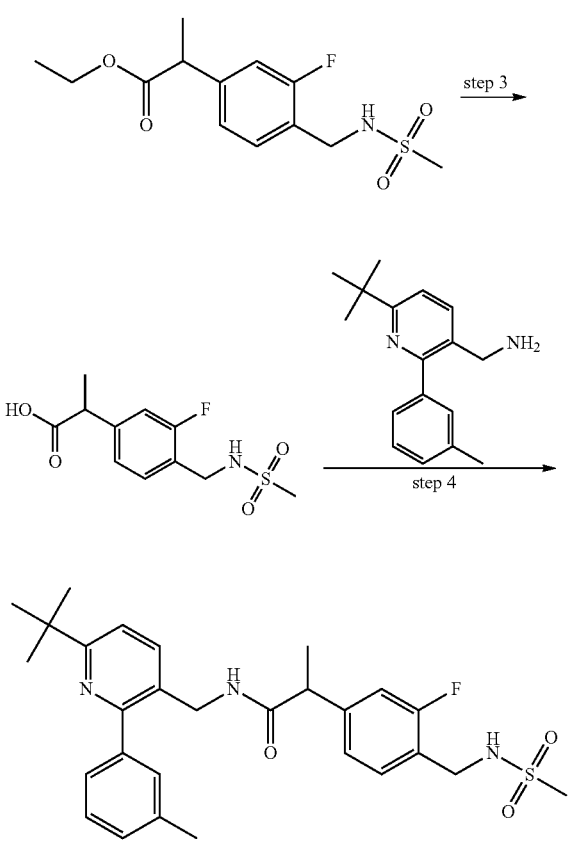

Step 1-3:

according to example 21.

Step 4:

To a stirred solution of 2-(3-fluoro-4-(methylsulfonamidomethyl)phenyl)propanoic acid (82 mg, 0.297 mmol) and (6-tert-butyl-2-m-tolylpyridin-3-yl)methanamine (76 mg, 0.297 mmol) in acetonitrile were added N-(3-dimethylaminopropyl)-N'-ethylcarbodiimide (85 mg, 0.445 mmol), 1-hydroxybenzotriazole (60 mg, 0.445 mmol) and triethylamine (0.1 mL, 0.742 mmol). The reaction mixture was stirred for 15 h at room temperature. The residue dissolved in ethyl acetate and washed with water and brine. The organic layer was dried over magnesium sulfate and filtered. The filtrate removed in vacuo. The crude was purified by column chromatography. N-((6-tert-Butyl-2-m-tolylpyridin-3-yl)methyl)-2-(3-fluoro-4-(methylsulfonamidomethyl)phenyl)propanamide (example 23) (122 mg) was obtained as 80% yield.

$^1$H NMR (300 MHz, CDCl$_3$) 7.5 (d, 1H, J=8.04 Hz, Ar), 7.26 (m, 6H, Ar), 6.97 (m, 2H, Ar), 5.43 (t, 1H, NH), 4.62 (t, 1H, NH), 4.44 (t, 2H, CH$_2$), 4.34 (d, 2H, CH$_2$), 3.42 (q, 1H, CH), 2.87 (s, 3H, mesyl), 2.38 (s, 3H, methyl), 1.43 (d, 3H, CH$_3$), 1.36 (s, 9H, t-Bu).

46

Synthesis of Example 24

2-(3-fluoro-4-(methylsulfonamidomethyl)phenyl)-N-((2-m-tolyl-6-(trifluoromethyl)pyridin-3-yl)methyl)propanamide

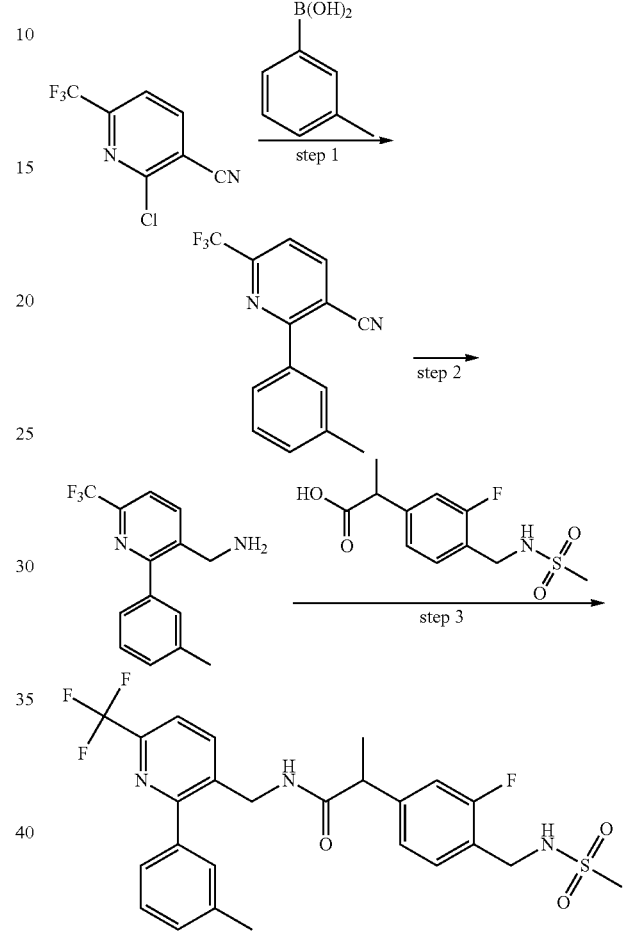

Step 1:

2-Chloro-6-(trifluoromethyl)nicotinonitrile (3 g, 14.56 mmol) was dissolved in toluene (70 mL) and ethanol (14 mL). m-tolylboronic acid (2.969 g, 21.814 mmol), aqueous sodium carbonate solution (2 M, 14 mL) and Pd(PPh$_3$)$_4$ (1.684 g, 1.456 mmol) were added. The mixture was flushed with nitrogen and stirred under microwave conditions (7 bar) at 100° C. for 2 h. The concentrated reaction mixture was cooled, diluted with ethyl acetate (200 mL), passed through celite (cyclohexane/ethyl acetate 9:1, 2×1 L) and concentrated in vacuo to afford 2-m-tolyl-6-(trifluoromethyl)nicotinonitrile (1.87 g, 49%).

Step 2:

2-m-tolyl-6-(trifluoromethyl)nicotinonitrile (1.87 g, 7.159 mmol) was dissolved in 2 M methanolic ammonia solution (286 mL, 0.025 mmol/mL) and hydrogenated in an H-cube apparatus (10 bar, 80° C., 1 mL/min, 0.25 mol/L). After removal of the solvent under vacuum, (2-m-tolyl-6-(trifluoromethyl)pyridin-3-yl)methanamine (1.787 g, 94%) was obtained as a white solid. The reaction step was repeated to afford in summary 3.61 g of (2-m-tolyl-6-(trifluoromethyl)pyridin-3-yl)methanamine.

Step 3:

To a stirred solution of (2-m-tolyl-6-(trifluoromethyl)pyridin-3-yl)methanamine (3.5 g, 13.143 mmol) and 2-(3-fluoro-4-(methylsulfonamidomethyl)phenyl)propanoic acid (5.415 g, 19.715 mmol) in tetrahydrofuran (102 mL) was added 1-hydroxybenzotriazolhydrate (1.834 mL, 13.143 mmol), O-(1H-benzotriazol-1-yl)-N,N,N',N'-tetramethyluronium tetrafluoroborate (4.213 g, 13.143 mmol) and N-ethyldiisopropylamine (6.676 mL, 39.429 mmol). The reaction mixture was stirred for 48 h. The reaction mixture was concentrated under reduced pressure and the solid obtained was purified by column chromatography (silica gel: 100-200 mesh, eluent: ethyl acetate/cyclohexane 2:1) to afford a white solid (2.65 mg, 32%).

Exemplary compound 15 was prepared in a similar manner as example 24.

Synthesis of Examples 25 and 26

(S)-2-(3-fluoro-4-(methylsulfonamidomethyl)phenyl)-N-((2-m-tolyl-6-(trifluoromethyl)pyridin-3-yl)methyl)propanamide and (R)-2-(3-fluoro-4-(methylsulfonamidomethyl)phenyl)-N-((2-m-tolyl-6-(trifluoromethyl)pyridin-3-yl)methyl)propanamide

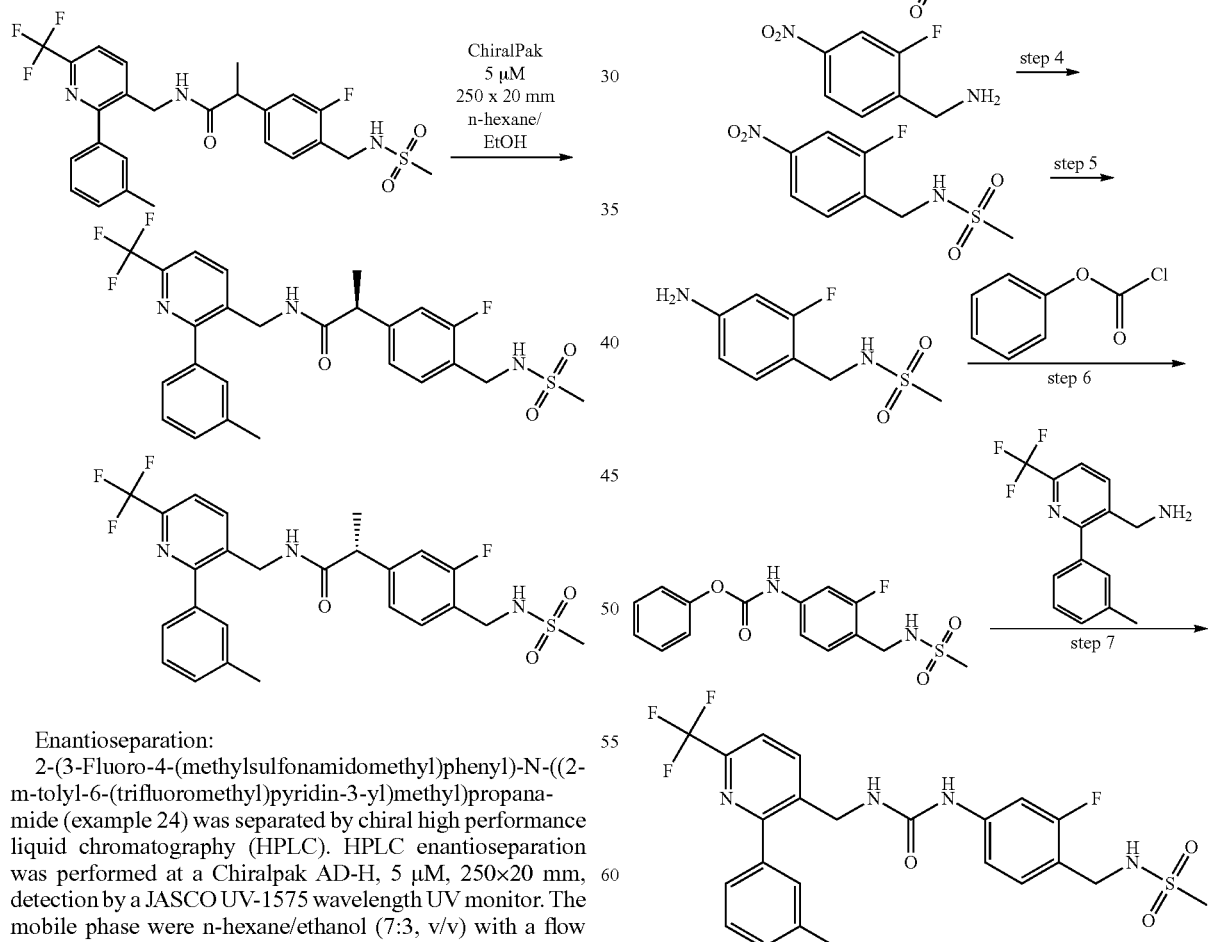

Enantioseparation:

2-(3-Fluoro-4-(methylsulfonamidomethyl)phenyl)-N-((2-m-tolyl-6-(trifluoromethyl)pyridin-3-yl)methyl)propanamide (example 24) was separated by chiral high performance liquid chromatography (HPLC). HPLC enantioseparation was performed at a Chiralpak AD-H, 5 µM, 250×20 mm, detection by a JASCO UV-1575 wavelength UV monitor. The mobile phase were n-hexane/ethanol (7:3, v/v) with a flow rate 19 mL/min at 25° C. 2.65 g of example 24 were separated by 70 separations each of 40 mg racemic mother compound. The eluent fractions corresponding to each chromatographic peaks were collected and evaporated in order to obtain enantiomerically pure fractions (S)-2-(3-fluoro-4-(methylsulfonamidomethyl)phenyl)-N-((2-m-tolyl-6-(trifluoromethyl)pyridin-3-yl)methyl)propanamide (example 25) (972 mg) and ((R)-2-(3-fluoro-4-(methylsulfonamidomethyl)phenyl)-N-((2-m-tolyl-6-(trifluoromethyl)pyridin-3-yl)methyl)propanamide (example 26) (1.07 g).

Synthesis of Example 27

N-(2-fluoro-4-(3-((2-m-tolyl-6-(trifluoromethyl)pyridin-3-yl)methyl)ureido)benzyl)methanesulfonamide

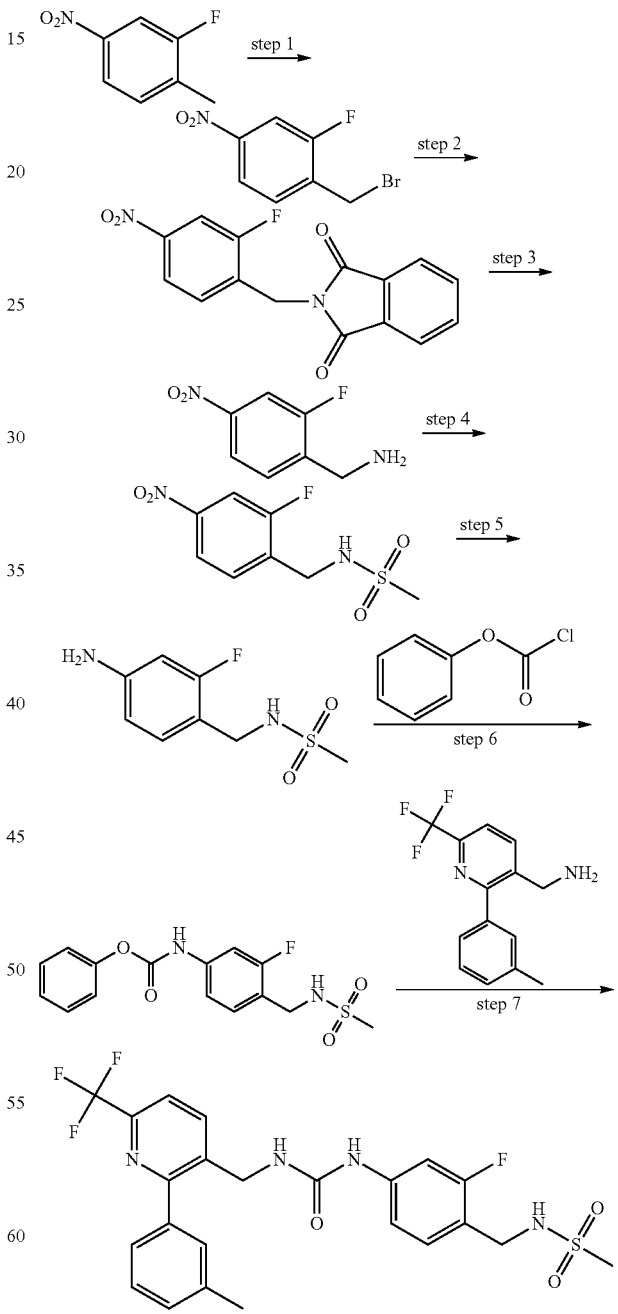

Step 1:

To a stirred solution of 2-fluoro-1-methyl-4-nitrobenzene (1 g, 6.446 mmol) in carbon tetrachloride was added benzoyl peroxide (497 mg, 1.2847 mmol) and N-bromosuccinimide (1.377 g, 7.736 mmol). The reaction mixture was refluxed for 18 h, then cooled to room temperature. The mixture was dissolved in ethyl acetate, then washed with water and brine. The organic layer was dried over magnesium sulfate and filtered. The filtrate was removed in vacuo to obtain 1-(bromomethyl)-2-fluoro-4-nitrobenzene (1.335 g) as a crude.

Step 2:

To a stirred solution of crude 1-(bromomethyl)-2-fluoro-4-nitrobenzene (1.335 g, 5.705 mmol) in dimethylformamide was added potassium phthalimide (2.324 g, 12.55 mmol). The reaction mixture was stirred for 18 h The mixture was dissolved in ethyl acetate, washed with water and brine. The organic layer was dried over magnesium sulfate and filtered. The filtrate was removed in vacuo. The crude was purified by column chromatography to give 2-(2-fluoro-4-nitrobenzyl)isoindoline-1,3-dione (1.229 g, 88%).

Step 3:

To a stirred solution of 2-(2-fluoro-4-nitrobenzyl)isoindoline-1,3-dione (500 mg, 1.665 mmol) in tetrahydrofuran were added hydrazine monohydrate (333 mg, 6.661 mmol) and p-toluenesulfonic acid monohydrate (29 mg, 0.167 mmol). The reaction mixture was refluxed for 6 h, then cooled to room temperature, diluted with ethyl acetate. The mixture was washed with water and brine. The organic layer was dried over magnesium sulfate and filtered. The filtrate was removed in vacuo. The crude was purified by column chromatography to give (2-fluoro-4-nitrophenyl)methanamine (194 mg, 68%).

Step 4:

To a stirred solution of (2-fluoro-4-nitrophenyl)methanamine (194 mg, 1.140 mmol) in pyridine, cooled to 0° C., were added methanesulfonyl chloride (248 mg, 2.166 mmol). The resulting reaction mixture was stirred for 1 h at room temperature. The mixture was dissolved in dichloromethane and washed with 1N HCl. The organic layer was dried over magnesium sulfate and filtered. The filtrate removed in vacuo. The crude was purified by column chromatography. N-(2-Fluoro-4-nitrobenzyl)methanesulfonamide (250 mg) was obtained as 88% yield.

Step 5:

To a stirred solution of N-(2-fluoro-4-nitrobenzyl)methanesulfonamide (250 mg, 1.007 mmol) in tetrahydrofuran and ethanol as co-solvent were added 10% Pd/C (25 mg). The mixture was charged with $H_2$ (gas) balloon. The resulting mixture was stirred for 15 h, then filtered by using celite. The filtrate was removed in vacuo. The crude was purified by column chromatography. N-(4-Amino-2-fluorobenzyl)methanesulfonamide (190 mg) was obtained as 86% yield.

Step 6:

To a stirred solution of N-(4-amino-2-fluorobenzyl)methanesulfonamide (190 mg, 0.871 mmol) in tetrahydrofuran and acetonitrile as co-solvent were added phenylchloroformate (0.115 ml, 0.914 mmol) and pyridine (0.084 ml, 1.045 mmol). The reaction mixture was stirred for 1 h at room temperature. The mixture dissolved in ethyl acetate and washed with water and brine. The organic layer was dried over magnesium sulfate and filtered. The filtrate was removed in vacuo. The crude was purified by column chromatography. Phenyl 3-fluoro-4-(methylsulfonamidomethyl)phenylcarbamate (250 mg) was obtained as 85% yield.

Step 7:

To a stirred solution of phenyl 3-fluoro-4-(methylsulfonamidomethyl)-phenylcarbamate (67 mg, 0.198 mmol) and (2-m-tolyl-6-(trifluoromethyl)pyridin-3-yl)methanamine (53 mg, 0.198 mmol) in acetonitrile were added 4-dimethylaminopyridine (24 mg, 0.198 mmol). The reaction mixture was stirred for 15 h at 50° C. The mixture was dissolved in ethyl acetate and washed with water and brine. The organic layer was dried over magnesium sulfate and filtered. The filtrate removed in vacuo. The crude was purified by column chromatography. N-(2-Fluoro-4-(3-((2-m-tolyl-6-(trifluoromethyl)pyridin-3-yl)methyl)ureido)benzyl)methanesulfonamide (example 27) (72 mg) was obtained as 72% yield.

$^1$H NMR (300 MHz, $CD_3OD$) 8.08 (d, 1H, J=7.5 Hz, Ar), 7.77 (d, 1H, J=8.04 Hz, Ar), 7.34 (m, 6H, Ar) 7.00 (dd, 1H, J=8.25 Hz, Ar), 4.45 (s, 2H, $CH_2$), 4.22 (s, 2H, $CH_2$), 2.84 (s, 3H, $CH_3$), 2.43 (s, 3H, $CH_3$).

Synthesis of Example 77

2-(3-chloro-4-(methylsulfonamidomethyl)phenyl)-N-((2-m-tolyl-6-(trifluoromethyl)pyridin-3-yl)methyl)propanamide

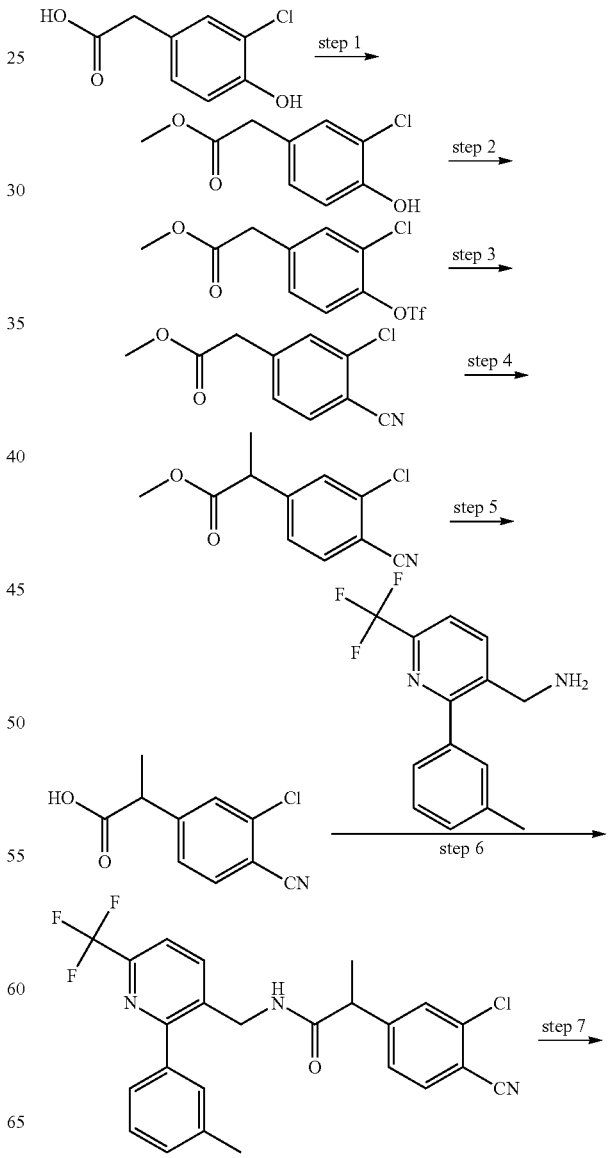

-continued

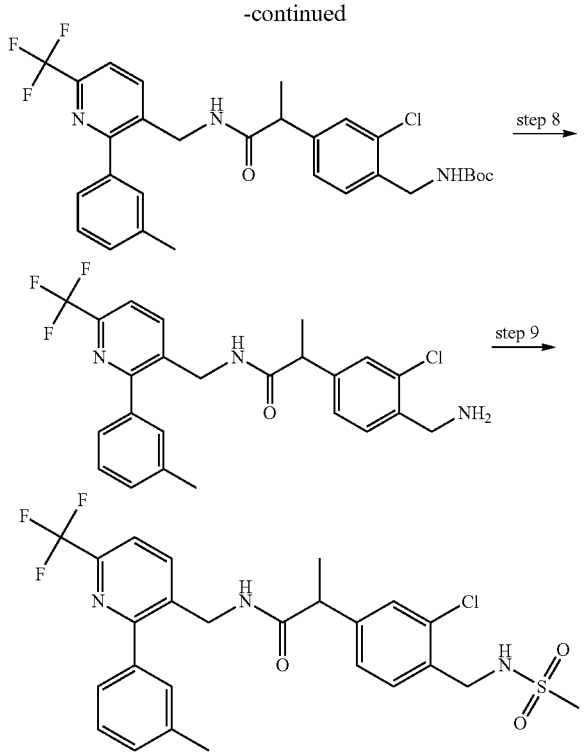

Step 1:

To a stirred solution of 2-(3-chloro-4-hydroxyphenyl)acetic acid (3 g, 16.078 mmol) in methanol (35 mL) were added sulfuric acid (0.3 mL). The reaction mixture was refluxed for 15 h and cooled to room temperature. The solvent was evaporated. The residue dissolved in ethyl acetate and extracted with NaHCO$_3$. The organic layer was dried over magnesium sulfate and filtered. The filtrate removed in vacuo. The crude was purified by column chromatography. Methyl 2-(3-chloro-4-hydroxyphenyl)acetate (3.557 g) was obtained as 99% yield.

Step 2:

To a stirred solution of methyl 2-(3-chloro-4-hydroxyphenyl)acetate (3.557 g, 17.73 mmol) and trimethylamine (2.5 mL, 17.73 mmol) in dichloromethane. Triflic anhydride (3 mL, 17.73 mmol) is added dropwise at 0° C. The reaction mixture was stirred for 2 h. The residue extracted in dichloromethane and washed with water and brine. The organic layer was dried over magnesium sulfate and filtered. The filtrate removed in vacuo. The crude was purified by column chromatography to give methyl 2-(3-chloro-4-(trifluoromethylsulfonyl-oxy)phenyl)acetate (5.15 g, 87%).

Step 3:

To a stirred solution of methyl 2-(3-chloro-4-(trifluoromethylsulfonyloxy)-phenyl)acetate (4.419 g, 13.283 mmol) in dimethylformamide were added zinc cyanide (1.6 g, 13.681 mmol) and tetrakis(triphenylphosphine) palladium (1.5 g, 1.3283 mmol). The reaction mixture was stirred for 34 h at 80° C., then cooled to room temperature and diluted with ethyl acetate. The mixture was filtered using celite pad. The filtrate dissolved in ethyl acetate and extracted with NaHCO$_3$. The organic layer was dried over magnesium sulfate and filtered. The filtrate removed in vacuo. The crude was purified by column chromatography to give methyl 2-(3-chloro-4-cyanophenyl)acetate (1.044 g, 37%).

Step 4:

To a stirred solution of methyl 2-(3-chloro-4-cyanophenyl)acetate (931 mg, 4.441 mmol) in dimethylformamide were added 60% sodium hydride (178 mg, 4.441 mmol) and iodomethane (0.3 mL, 4.441 mmol) at 0° C. The reaction mixture was stirred for 1 h at 0° C., then diluted with water. The residue dissolved in ethyl acetate and washed with water and brine. The organic layer was dried over magnesium sulfate and filtered. The filtrate removed in vacuo. The crude was purified by column chromatography to give methyl 2-(3-chloro-4-cyanophenyl)propanoate (642 mg, 65%).

Step 5:

To a stirred solution of methyl 2-(3-chloro-4-cyanophenyl)propanoate (642 mg, 2.87 mmol) in co-solvent with tetrahydrofuran and water (1:1) were added sodium hydroxide (287 mg, 7.175 mmol). The reaction mixture was stirred for 15 h at room temperature, then acidified to pH 3-4 with acetic acid. The residue dissolved in ethyl acetate and washed with water and brine. The organic layer was dried over magnesium sulfate and filtered. The filtrate removed in vacuo. The crude was purified by column chromatography. 2-(3-Chloro-4-cyanophenyl)propanoic acid (665 mg) was obtained as 99% yield.

Step 6:

To a stirred solution of 2-(3-chloro-4-cyanophenyl)propanoic acid (95 mg, 0.454 mmol) and (2-m-tolyl-6-(trifluoromethyl)pyridin-3-yl)methanamine (121 mg, 0.454 mmol) in acetonitrile were added N-(3-dimethylaminopropyl)-N'-ethylcarbodiimide (131 mg, 0.681 mmol), 1-hydroxybenzotriazole (92 mg, 0.681 mmol) and triethylamine (0.16 mL, 1.135 mmol). The reaction mixture was stirred for 15 h at room temperature. The residue dissolved in ethyl acetate and washed with water and brine. The organic layer was dried over magnesium sulfate and filtered. The filtrate removed in vacuo. The crude was purified by column chromatography. 2-(3-chloro-4-cyanophenyl)-N-((2-m-tolyl-6-(trifluoromethyl)pyridin-3-yl)methyl)propanamide (182 mg) was obtained as 88% yield.

Step 7:

To a stirred solution of 2-(3-chloro-4-cyanophenyl)-N-((2-m-tolyl-6-(trifluoromethyl)pyridin-3-yl)methyl)propanamide (182 mg, 0.397 mmol) in methanol, cooled to 0° C., were added di-tert-butyl dicarbonate (173 mg, 0.794 mmol) and NiCl$_2$.6H$_2$O (9 mg, 0.0397 mmol). Sodium borhydride (105 mg, 2.779 mmol) was then added in small portions. The resulting reaction mixture was allowed to warm to room temperature and left to stir for 1 h. Diethylenetriamine (0.04 mL, 0.397 mmol) was added to the mixture. The mixture was stirred for 1 h. The solvent was evaporated. The residue dissolved in ethyl acetate and extracted with NaHCO$_3$. The organic layer was dried over magnesium and filtered. The filtrate removed in vacuo. The crude was purified by column chromatography. tert-Butyl 2-chloro-4-(1-oxo-1-((2-m-tolyl-6-(trifluoromethyl)pyridin-3-yl)methylamino)propan-2-yl)benzylcarbamate (132 mg) was obtained as 59% yield.

Step 8:

To a stirred solution of tert-butyl 2-chloro-4-(1-oxo-1-((2-m-tolyl-6-(trifluoromethyl)pyridin-3-yl)methylamino)propan-2-yl)benzylcarbamate (132 mg, 0.234 mmol) in dichloromethane (4 mL), cooled to 0° C., were added trifluoroacetic acid (2 ml). The resulting reaction mixture was stirred for 1 h at 0° C. and 1 hour at room temperature, then basified to pH 8-9 with aq. NaHCO$_3$. The mixture was filtered using celite pad. The filtrate dissolved in dichloromethane and extracted with NaHCO$_3$. The organic layer was dried over magnesium sulfate and filtered. The filtrate removed in vacuo. The crude was purified by column chromatography. 2-(4-(aminomethyl)-3-chlorophenyl)-N-((2-m-tolyl-6-(trifluoromethyl)pyridin-3-yl)methyl)propanamide (90 mg) was obtained as 83% yield.

Step 9:

To a stirred solution of 2-(4-(aminomethyl)-3-chlorophenyl)-N-((2-m-tolyl-6-(trifluoromethyl)pyridin-3-yl)methyl)propanamide (90 mg, 0.195 mmol) in pyridine, cooled to 0° C., were added methanesulfonyl chloride (90 mg). The resulting reaction mixture was stirred for 15 h at room temperature. The mixture dissolved in dichloromethane and washed with 1N HCl. The organic layer was dried over magnesium sulfate and filtered. The filtrate removed in vacuo. The crude was purified by column chromatography. 2-(3-Chloro-4-(methylsulfonamidomethyl)phenyl)-N-((2-m-tolyl-6-(trifluoromethyl)pyridin-3-yl)methyl)propanamide (example 77) (87 mg) was obtained as 83% yield. $^1$H NMR (300 MHz, CDCl$_3$) 7.77 (d, 1H, J=8.04 Hz, Ar), 7.58 (d, 1H J=8.07 Hz, Ar), 7.39 (d, 1H, J=7.86 Hz, Ar), 7.28 (m, 4H, Ar), 7.13 (m, 2H, Ar), 5.59 (t, 1H, NH), 4.82 (t, 1H, NH), 4.47 (d, 2H, J=6.03 Hz, CH$_2$), 4.37 (d, 2H, J=6.39, CH$_2$), 3.44 (q, 1H, CH), 2.88 (s, 3H, mesyl), 2.38 (s, 3H, methyl), 1.44 (d, 3H, J=7.14 Hz, CH$_3$)

Synthesis of Example 78

2-(3-methoxy-4-(methylsulfonamidomethyl)phenyl)-N-((2-m-tolyl-6-(trifluoromethyl)pyridin-3-yl)methyl)propanamide

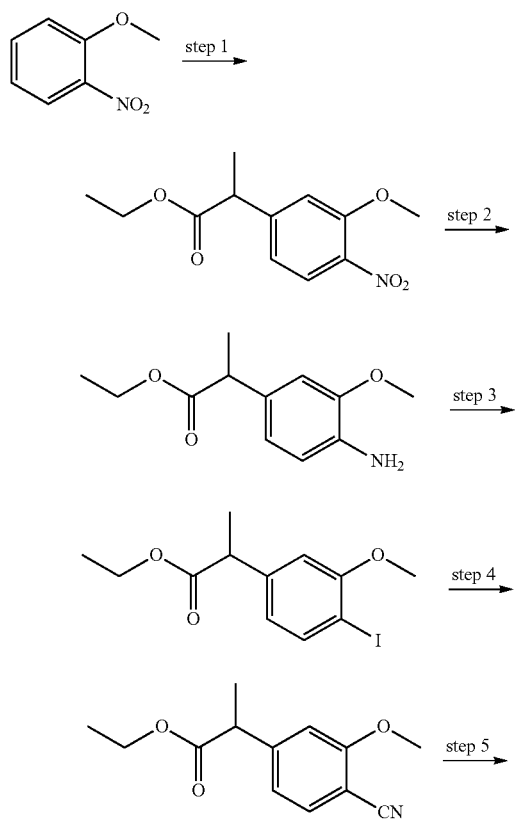

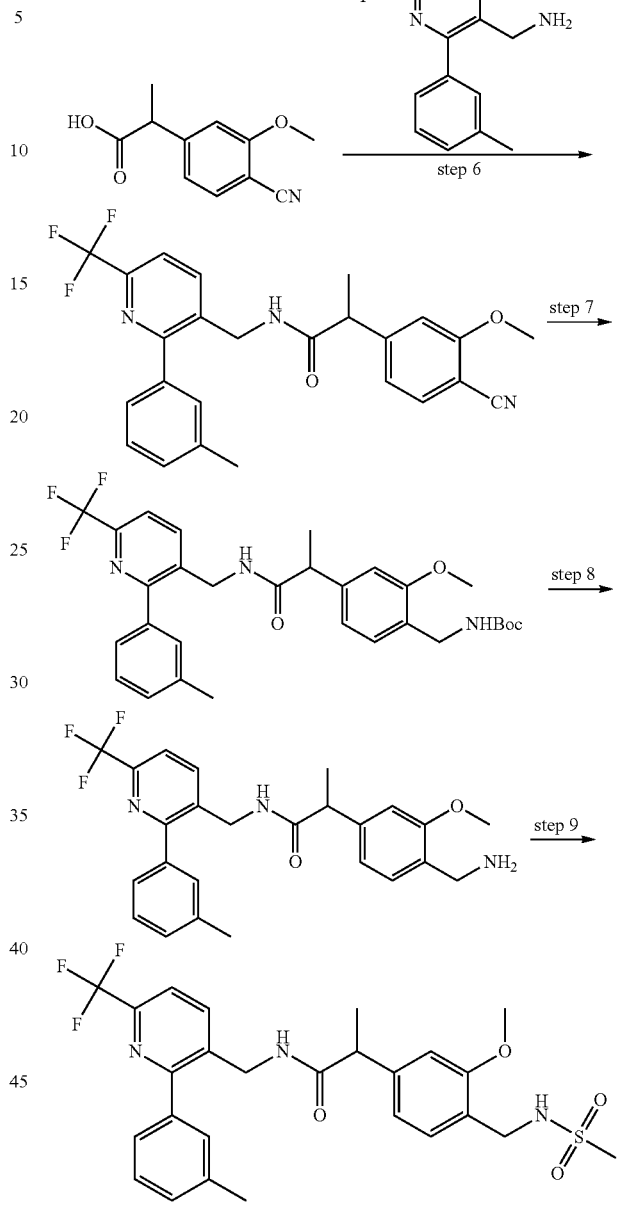

Step 1:

To a stirred solution of 1-methoxy-2-nitrobenzene (3 g, 19.59 mmol) in dimethylformamide were added potassium tert-butoxide (8.792 g, 78.36 mmol) and ethyl 2-chloropropionate (2.5 ml, 19.59 mmol) while maintaining temperature below −30° C. The reaction mixture was stirred for 5 min at −30° C., then ethyl 2-chloropropionate (0.25 mL, 1.959 mmol) was added to mixture. The reaction mixture was stirred for 10 min at room temperature. The residue was dissolved in ethyl acetate and washed with water and brine. The organic layer was dried over magnesium sulfate and filtered. The filtrate removed in vacuo. The crude was purified by column chromatography. Ethyl 2-(3-methoxy-4-nitrophenyl)propanoate (683 mg) was obtained as 14% yield.

Step 2:

To a stirred solution of ethyl 2-(3-methoxy-4-nitrophenyl)propanoate (683 mg, 2.697 mmol) in tetrahydrofuran and ethanol as co-solvent were added 10% Pd/C (70 mg). The mixture was charged with $H_2$ (gas) balloon. The resulting mixture was stirred for 15 h, then filtered using celite. The filtrate removed in vacuo. The crude was purified by column chromatography. Ethyl 2-(4-amino-3-methoxyphenyl)propanoate (447 mg) was obtained as 74% yield.

Step 3:

To a stirred solution of ethyl 2-(4-amino-3-methoxyphenyl)propanoate (447 mg, 2.002 mmol) in acetonitrile and water were added p-toluenesulfonic acid monohydrate (1.142 g, 6.006 mmol), sodium nitrite (276 mg, 4.004 mmol) and potassium iodide (831 mg, 5.005 mmol). The reaction mixture was stirred for 4 h at room temperature. The mixture dissolved in ethyl acetate and washed with water and brine. The organic layer was dried over magnesium sulfate and filtered. The filtrate removed in vacuo. The crude was purified by column chromatography. Ethyl 2-(4-iodo-3-methoxyphenyl)propanoate (468 mg) was obtained as 70% yield.

Step 4:

To a stirred solution of ethyl 2-(4-iodo-3-methoxyphenyl) propanoate (626 mg, 1.873 mmol) in dimethylformamide were added zinc cyanide (227 mg, 1.929 mmol) and tetrakis (triphenylphosphine) palladium (216 mg, 0.1873 mmol). The reaction mixture was stirred for 36 h at 120° C., then cooled to room temperature, diluted with ethyl acetate. The mixture was filtered using celite pad. The filtrate dissolved in ethyl acetate and extracted with $NaHCO_3$. The organic layer was dried over magnesium sulfate and filtered. The filtrate removed in vacuo. The crude was purified by column chromatography. Ethyl 2-(4-cyano-3-methoxyphenyl)propanoate (222 mg) was obtained as 51% yield.

Step 5:

To a stirred solution of ethyl 2-(4-cyano-3-methoxyphenyl)propanoate (222 mg, 0.952 mmol) in co-solvent with tetrahydrofuran and water (1:1) were added sodium hydroxide (95 mg, 2.38 mmol). The reaction mixture was stirred for 15 h at room temperature, then acidified to pH 3-4 with acetic acid. The residue dissolved in ethyl acetate and washed with water and brine. The organic layer was dried over magnesium sulfate and filtered. The filtrate removed in vacuo. The crude was purified by column chromatography. 2-(4-Cyano-3-methoxyphenyl)propanoic acid (188 mg) was obtained as 96% yield.

Step 6:

To a stirred solution of 2-(4-cyano-3-methoxyphenyl)propanoic acid (112 mg, 0.545 mmol) and (2-m-tolyl-6-(trifluoromethyl)pyridin-3-yl)methanamine (145 mg, 0.546 mmol) in acetonitrile were added N-(3-dimethylaminopropyl)-N'-ethylcarbodiimide (157 mg, 0.819 mmol), N-hydroxybenzotriazole (111 mg, 0.819 mmol) and triethylamine (0.19 mL, 1.36 mmol). The reaction mixture was stirred for 15 h at room temperature. The residue dissolved in ethyl acetate and washed with water and brine. The organic layer was dried over magnesium sulfate and filtered. The filtrate removed in vacuo. The crude was purified by column chromatography. 2-(4-Cyano-3-methoxyphenyl)-N-((2-m-tolyl-6-(trifluoromethyl)pyridin-3-yl)methyl)propanamide (222 mg) was obtained as 90% yield.

Step 7:

To a stirred solution of 2-(4-cyano-3-methoxyphenyl)-N-((2-m-tolyl-6-(trifluoromethyl)pyridin-3-yl)methyl)propanamide (222 mg, 0.49 mmol) in methanol, cooled to 0° C., were added di-tert-butyl dicarbonate (220 mg, 0.98 mmol) and $NiCl_2.6H_2O$ (12 mg, 0.05 mmol). Sodium borohydride (130 mg, 3.43 mmol) was then added in small portions. The resulting reaction mixture was allowed to warm to room temperature and left to stir for 1 h. Diethylenetriamine (0.05 mL, 0.49 mmol) was added to the mixture. The mixture was stirred for 1 h. The solvent was evaporated. The residue dissolved in ethyl acetate and extracted with $NaHCO_3$. The organic layer was dried over magnesium sulfate and filtered. The filtrate removed in vacuo. The crude was purified by column chromatography. tert-Butyl 2-methoxy-4-(1-oxo-1-((2-m-tolyl-6-(trifluoromethyl)pyridin-3-yl)methylamino) propan-2-yl)benzylcarbamate (161 mg) was obtained as 59% yield.

Step 8:

To a stirred solution of tert-butyl 2-methoxy-4-(1-oxo-1-((2-m-tolyl-6-(trifluoromethyl)pyridin-3-yl)methylamino) propan-2-yl)benzylcarbamate (161 mg, 0.29 mmol) in dichloromethane (4 mL), cooled to 0° C., were added trifluoroacetic acid (2 mL). The resulting reaction mixture was stirred for 2 h at 0° C. and 2 h at room temperature, then basified to pH 8-9 with aq. $NaHCO_3$. The mixture was filtered using celite pad. The filtrate dissolved in dichloromethane and extracted with $NaHCO_3$. The organic layer was dried over magnesium sulfate and filtered. The filtrate removed in vacuo. The crude was purified by column chromatography. 2-(4-(Aminomethyl)-3-methoxyphenyl)-N-((2-m-tolyl-6-(trifluoromethyl)pyridin-3-yl)methyl)propanamide (151 mg) was obtained as 99% yield.

Step 9:

To a stirred solution of 2-(4-(aminomethyl)-3-methoxyphenyl)-N-((2-m-tolyl-6-(trifluoromethyl)pyridin-3-yl) methyl)propanamide (151 mg, 0.33 mmol) in pyridine, cooled to 0° C., were added methanesulfonyl chloride (151 mg). The resulting reaction mixture was stirred for 15 h at room temperature. The mixture dissolved in dichloromethane and washed with 1N HCl. The organic layer was dried over magnesium sulfate and filtered. The filtrate removed in vacuo. The crude was purified by column chromatography. 2-(3-Methoxy-4-(methylsulfonamidomethyl)phenyl)-N-((2-m-tolyl-6-(trifluoromethyl)pyridin-3-yl)methyl)propanamide (example 78) (38 mg) was obtained as 22% yield.

$^1$H NMR (300 MHz, $CDCl_3$) 7.76 (d, 1H, J=8.04 Hz, Ar), 7.57 (d, 1H, J=8.04 Hz, Ar), 7.24 (m, 5H, Ar), 6.76 (d, 2H, Ar), 5.57 (t, 1H, NH), 4.85 (t, 1H, NH), 4.45 (d, 2H, $CH_2$), 4.26 (d, 2H, $CH_2$), 3.81 (s, 3H, methoxy), 3.49 (q, 1H, CH), 2.81 (s, 3H, mesyl), 2.37 (s, 3H, methyl), 1.47 (d, 3H, $CH_3$).

Synthesis of Example 81

N-(2-methyl-4-(3-((2-m-tolyl-6-(trifluoromethyl) pyridin-3-yl)methyl)ureido)benzyl)methanesulfonamide

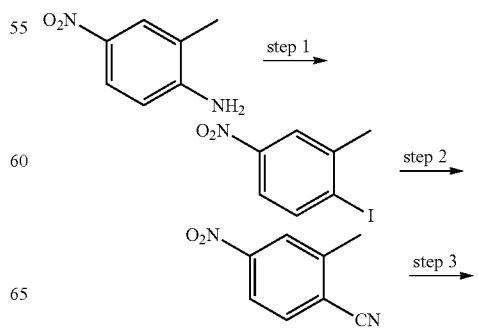

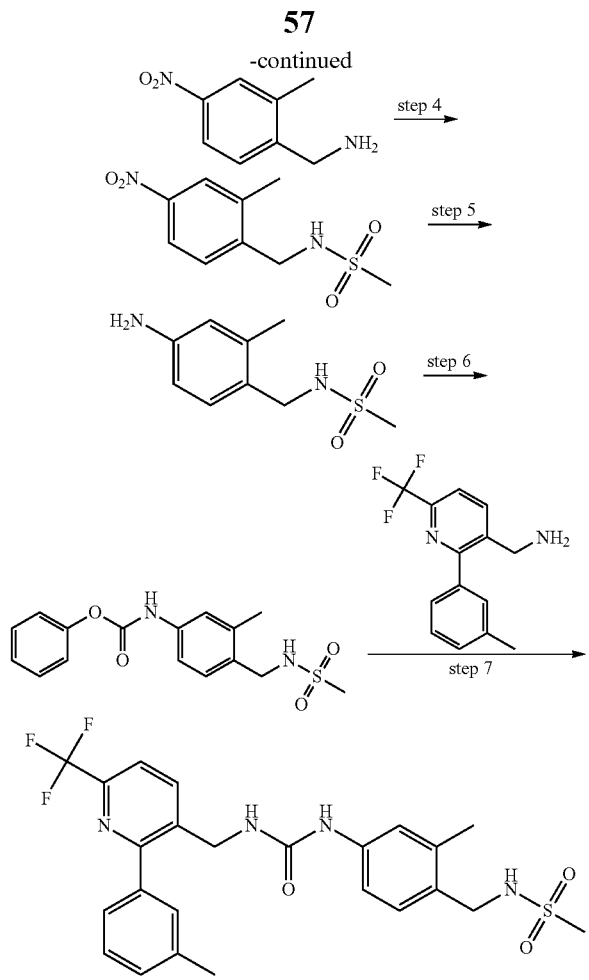

Step 1:

To a stirred solution of 2-methyl-4-nitroaniline (500 mg, 3.286 mmol) in acetonitrile and water were added p-toluenesulfonic acid monohydrate (1.875 g, 9.858 mmol), sodium nitrite (453 mg, 6.572 mmol) and potassium iodide (1.363 g, 8.215 mmol). The reaction mixture was stirred for 4 h at room temperature. The mixture dissolved in ethyl acetate and washed with water and brine. The organic layer was dried over magnesium sulfate and filtered. The filtrate removed in vacuo. The crude was purified by column chromatography to give 1-iodo-2-methyl-4-nitrobenzene (812 mg, 94%).

Step 2:

To a stirred solution of 1-iodo-2-methyl-4-nitrobenzene (812 mg, 3.087 mmol) in dimethylformamide were added zinc cyanide (544 mg, 4.63 mmol) and tetrakis(triphenylphosphine) palladium (713 mg, 0.6174 mmol). The reaction mixture was stirred for 24 h at 120° C., then cooled to room temperature and diluted with ethyl acetate. The mixture was filtered using celite pad. The filtrate dissolved in ethyl acetate and extracted with NaHCO$_3$. The organic layer was dried over magnesium sulfate and filtered. The filtrate removed in vacuo. The crude was purified by column chromatography to give 2-methyl-4-nitrobenzonitrile (407 mg, 81%).

Step 3:

To a stirred solution of 2-methyl-4-nitrobenzonitrile (407 mg, 2.510 mmol) in tetrahydrofuran was added 2M BH$_3$.SMe$_2$ in tetrahydrofuran (2.1 mL). The reaction mixture was stirred for 15 h at 70° C. The mixture was cooled to room temperature, then quenched by water. The mixture dissolved in ethyl acetate and washed with water and brine. The organic layer was dried over magnesium sulfate and filtered. The filtrate removed in vacuo. The crude was purified by column chromatography to give (2-methyl-4-nitrophenyl)methanamine (178 mg, 43%).

Step 4:

To a stirred solution of (2-methyl-4-nitrophenyl)methanamine (178 mg, 1.071 mmol) in pyridine, cooled to 0° C., were added methane sulfonylchloride (0.16 mL, 2.0349 mmol). The resulting reaction mixture was stirred for 2 h. The mixture dissolved in dichloromethane and washed with 1N HCl. The organic layer was dried over magnesium sulfate and filtered. The filtrate removed in vacuo. The crude was purified by column chromatography to obtain N-(2-methyl-4-nitrobenzyl)methanesulfonamide (100 mg, 38%).

Step 5:

To a stirred solution of N-(2-methyl-4-nitrobenzyl)methanesulfonamide (100 mg, 0.409 mmol) in tetrahydrofuran and ethanol as co-solvent were added 10% Pd/C (40 mg). The mixture was charged with H$_2$ (gas) balloon. The resulting mixture was stirred for 24 h, then filtered using celite. The filtrate removed in vacuo. The crude was purified by column chromatography. N-(4-Amino-2-methylbenzyl)methanesulfonamide (61 mg) was obtained as 70% yield.

Step 6:

To a stirred solution of N-(4-amino-2-methylbenzyl)methanesulfonamide (61 mg, 0.285 mmol) in tetrahydrofuran and acetonitrile as co-solvent were added phenylchloroformate (0.04 mL, 0.299 mmol) and pyridine (0.03 mL, 0.342 mmol). The reaction mixture was stirred for 3 h at room temperature. The mixture dissolved in ethyl acetate and washed with water and brine. The organic layer was dried over magnesium sulfate and filtered. The filtrate removed in vacuo. The crude was purified by column chromatography to give phenyl 3-methyl-4-(methylsulfonamidomethyl)phenylcarbamate (93 mg, 98%).

Step 7:

To a stirred solution of phenyl 3-methyl-4-(methylsulfonamidomethyl)-phenylcarbamate (46 mg, 0.137 mmol) and (2-m-tolyl-6-(trifluoromethyl)pyridin-3-yl)methanamine (36 mg, 0.137 mmol) in acetonitrile were added 4-dimethylaminopyridine (17 mg, 0.137 mmol). The reaction mixture was stirred for 15 h at 50° C. The mixture dissolved in ethyl acetate and washed with water and brine. The organic layer was dried over magnesium sulfate and filtered. The filtrate removed in vacuo. The crude was purified by column chromatography. N-(2-Methyl-4-(3-((2-m-tolyl-6-(trifluoromethyl)pyridin-3-yl)methyl)ureido)benzyl)methanesulfonamide (example 81) (61 mg) was obtained as 88% yield.

$^1$H NMR (300 MHz, DMSO) 8.66 (s, 1H), 8.07 (d, 1H, J=8.43 Hz, Ar), 7.91 (d, 1H, J=8.07 Hz, Ar), 7.27 (m, 8H, Ar), 6.75 (t, 1H, NH), 4.37 (d, 2H, CH$_2$), 4.03 (d, 2H, CH$_2$), 2.83 (s, 3H, mesyl), 2.40 (s, 3H, methyl), 2.23 (s, 3H, methyl).

Synthesis of Example 82

N-(4-(3-((2-m-tolyl-6-(trifluoromethyl)pyridin-3-yl)methyl)ureido)benzyl)ethanesulfonamide

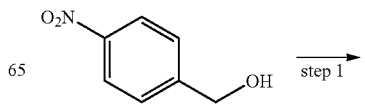

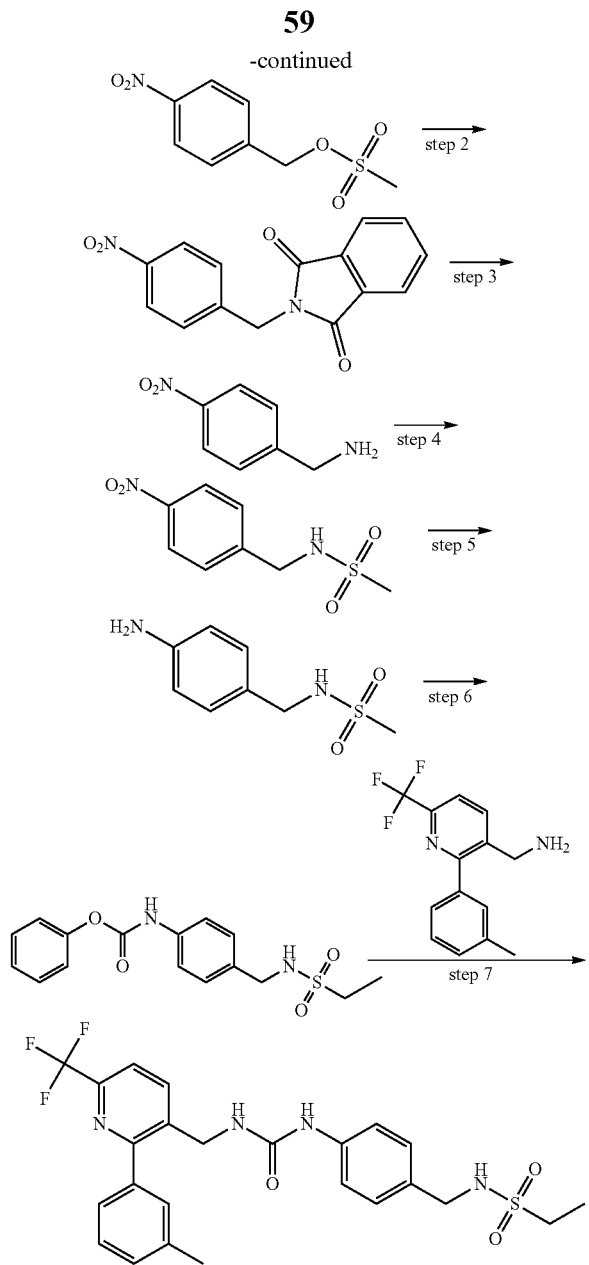

Step 1:

To a solution of (4-nitrophenyl)methanol (2 g, 13.06 mmol) in toluene (10 mL) was slowly added methane sulfonylchloride (1.21 mL, 15.67 mmol) at room temperature. The reaction mixture was heated to 80° C. for 4 h. TLC showed complete consumption of starting material. The reaction mixture was cooled to room temperature. The mixture was extracted with ethyl acetate and washed with water and brine. The extract was dried over magnesium sulfate and concentrated under reduced pressure. The crude was purified by column chromatography to 4-nitrobenzyl methanesulfonate (2.2 g, 72%).

Step 2:

A solution of 4-nitrobenzyl methanesulfonate (2.2 g, 9.51 mmol) in dimethylformamide (10 mL) was added potassium phthalimide (1.9 g, 10.50 mmol) and stirred at room temperature for overnight. TLC showed complete consumption of starting material. The mixture was extracted with ethyl acetate and washed with water and brine. The extract was dried over magnesium sulfate and concentrated under reduced pressure. The crude was purified by crystallization to 2-(4-nitrobenzyl)isoindoline-1,3-dione (1.6 g, 60%).

Step 3:

2-(4-Nitrobenzyl)isoindoline-1,3-dione (1.6 g, 5.67 mmol) was dissolved in tetrahydrofuran (8 mL). To the solution hydrazine monohydrate (1.7 mL, 22.675 mmol) and p-toluenesulfonic acid monohydrate (108 mg, 0.57 mmol) was added. It was refluxed for 6 h. TLC showed complete consumption of starting material. The mixture was extracted with ethyl acetate and washed with water and brine. The extract was dried over magnesium sulfate and concentrated under reduced pressure. The crude was purified by column chromatography to give (4-nitrophenyl)methanamine (715 mg, 83%).

Step 4:

(4-Nitrophenyl)methanamine (715 mg, 4.7 mmol) was dissolved in pyridine (4 mL). The reaction mixture was added ethane sulfonyl chloride (0.58 mL, 6.11 mmol) and stirred for 1 h at room temperature. TLC showed complete consumption of starting material. The mixture was diluted with 1N HCl and extracted with ethyl acetate. The extract was dried over magnesium sulfate and concentrated under reduced pressure. The crude was purified by column chromatography to give N-(4-nitrobenzyl)ethanesulfonamide (776 mg, 68%).

Step 5:

N-(4-Nitrobenzyl)ethanesulfonamide (776 mg, 3.18 mmol) was dissolved in methanol and tetrahydrofuran (1:1, 35 mL). 10% Pd/C (264 mg, 3 equiv) was added to it. The resulting mixture was stirred at room temperature for overnight under $H_2$. TLC showed complete consumption of starting material. The mixture was filtered through celite bed and the filtrate was concentrated under reduced pressure. The crude was purified by column chromatography to give N-(4-aminobenzyl)ethanesulfonamide (504 mg, 74%).

Step 6:

N-(4-Aminobenzyl)ethanesulfonamide (504 mg, 2.35 mmol) was dissolved in acetonitrile (3 mL) and tetrahydrofuran (4 mL). The reaction mixture was added pyridine (0.23 mL, 2.78 mmol) and phenyl chloroformate (0.31 mL, 2.43 mmol) and stirred at room temperature for 3 h under nitrogen atmosphere. TLC showed complete consumption of starting material. The reaction mixture was diluted with water and extracted with ethyl acetate. The organic part was washed with water and brine. The organic layer was dried over magnesium sulfate and concentrated under reduced pressure. The crude was purified by column chromatography to give phenyl 4-(ethylsulfonamidomethyl)phenylcarbamate (697 mg, 87%).

Step 7:

To a solution of phenyl 4-(ethylsulfonamidomethyl)phenylcarbamate (74 mg, 0.22 mmol) in acetonitrile (3 mL) was added 4-dimethylaminopyridine (27 mg, 0.22 mmol) and (2-m-tolyl-6-(trifluoromethyl)pyridin-3-yl)methanamine (59 mg, 0.22 mmol) at room temperature. The reaction mixture was heated to 50° C. for 15 h. TLC showed complete consumption of starting material. The reaction mixture was diluted with water and extracted with ethylacetate. The organic part was washed with water and brine. The organic layer was dried over magnesium sulfate and concentrated under reduced pressure. The crude was purified by column chromatography to give N-(4-(3-((2-m-tolyl-6-(trifluoromethyl)pyridin-3-yl)methyl)ureido)benzyl)ethanesulfonamide (example 82) (50 mg, 45%).

$^1$H NMR (300 MHz, $CD_3OD$) δ 8.10 (d, 1H, J=8.07 Hz, Ar—H), 7.78 (d, 1H, J=8.22 Hz, Ar—H), 7.24-7.43 (m, 8H, Ar—H), 4.45 (s, 2H, Ar—$CH_2$), 4.15 (s, 2H, $CH_2$), 2.87-2.94 (q, 2H, J=7.32 Hz, $CH_2$), 2.43 (s, 3H, Ar—$CH_3$), 2.23 (t, 3H, J=7.32 Hz, $CH_3$).

Synthesis of Example 83

2-(4-(ethylsulfonamidomethyl)-3-fluorophenyl)-N-((2-m-tolyl-6-(trifluoromethyl)pyridin-3-yl)methyl)propanamide

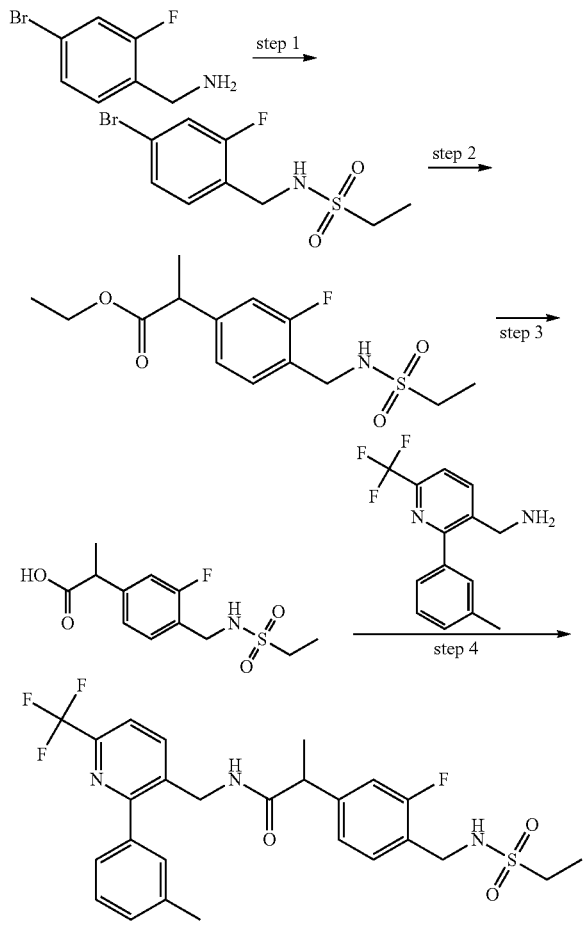

Step 1:
(4-Bromo-2-fluorophenyl)methanamine (924 mg, 4.53 mmol) was dissolved in pyridine and ethane sulfonyl chloride (0.82 mL, 8.60 mmol) was added to the solution at 0° C. The mixture was stirred for 1 h at 0° C. Then, the mixture was quenched with 1N HCl and extracted with ethyl acetate. Drying over magnesium sulfate and evaporation of the ethyl acetate and purified by column chromatography gave N-(4-bromo-2-fluorobenzyl)-ethanesulfonamide in pure form (1.06 g, 79%).

Step 2:
To a solution of N-(4-bromo-2-fluorobenzyl)ethanesulfonamide (305 mg, 1.03 mmol) in dimethylformamide, Manganese (113 mg, 2.06 mmol), (2,2'-Bipyridine)nickel(II)-dibromide (27 mg, 0.07 mmol), ethyl 2-chloropropanoate (0.17 mL, 1.34 mmol) was added. It was followed by addition of trifluoroacetic acid (0.002 mL, 0.028 mmol). The mixture was stirred for 24 h at 65° C. The reaction mixture was quenched by concentrated HCl (7 drops). Then it was extracted with diethyl ether, dried over magnesium sulfate, the solvent was evaporated in vacuo. It was purified by column chromatography to obtain ethyl 2-(4-(ethylsulfonamidomethyl)-3-fluorophenyl)propanoate in pure form (65 mg, 20%).

Step 3:
To a solution of ethyl 2-(4-(ethylsulfonamidomethyl)-3-fluorophenyl)propanoate (60 mg, 0.189 mmol) in tetrahydrofuran and water co-solvent, sodium hydroxide (19 mg) was added at room temperature. The mixture was stirred for overnight and extracted with ethyl acetate, dried over magnesium sulfate, the solvent was evaporated in vacuo. It was purified by column chromatography to give 2-(4-(ethylsulfonamidomethyl)-3-fluorophenyl)propanoic acid (55 mg).

Step 4:
2-(4-(Ethylsulfonamidomethyl)-3-fluorophenyl)propanoic acid (60 mg, 0.207 mmol) and (2-m-tolyl-6-(trifluoromethyl)pyridin-3-yl)methanamine (61 mg, 0.228 mmol) was dissolved and mixed in 1,4-dioxane, followed by addition of N-hydroxybenzotriazole (42 mg, 0.311 mmol) and N-(3-dimethylaminopropyl)-N'-ethylcarbodiimide (60 mg, 0.311 mmol) and triethylamine (0.07 mL, 0.518 mmol). The reaction mixture was stirred for overnight and then quenched by water and extracted with ethyl acetate. Drying over magnesium sulfate, evaporation of the ethyl acetate and purification by column chromatography gave 2-(4-(ethylsulfonamidomethyl)-3-fluorophenyl)-N-((2-m-tolyl-6-(trifluoromethyl)pyridin-3-yl)methyl)propanamide (example 83) in pure form (52 mg, 47%).

$^1$H-NMR (400 MHz, CDCl$_3$) δ 7.75 (d, 1H, J=6.40 Hz, Ar—H), 7.57 (d, 1H, J=6.36 Hz, Ar—H), 7.31 (m, 2H, Ar—H), 7.21 (m, 2H, Ar—H), 7.15 (d, 1H, J=5.92 Hz, Ar—H), 6.95 (m, 2H, Ar—H), 5.50 (m, 1H, amide-NH), 4.46 (m, 3H, amide-NH, Ar—CH$_2$), 4.30 (d, 2H, J=5.04 Hz, Ar—CH$_2$), 3.45 (q, 1H, J=5.68 Hz, amide-α-H), 2.97 (q, 2H, J=5.92 Hz, ethanesulfonly-2H), 2.37 (s, 1H, Ar—CH$_3$), 1.43 (d, 3H, J=5.68 Hz, amide-3H), 1.30 (t, 3H, J=5.88 Hz ethanesulfonly-3H).

Synthesis of Example 84

1-{[2-m-tolyll-6-(trifluoromethyl)pyridin-3-yl]methyl}-3-{4-[(sulfamoylamino)methyl]phenyl}urea

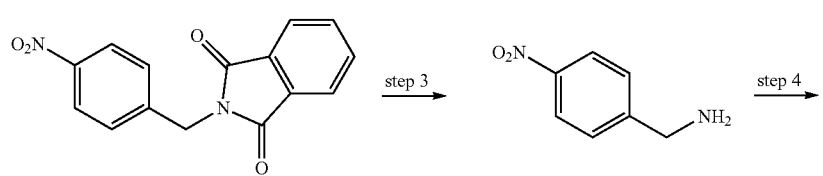

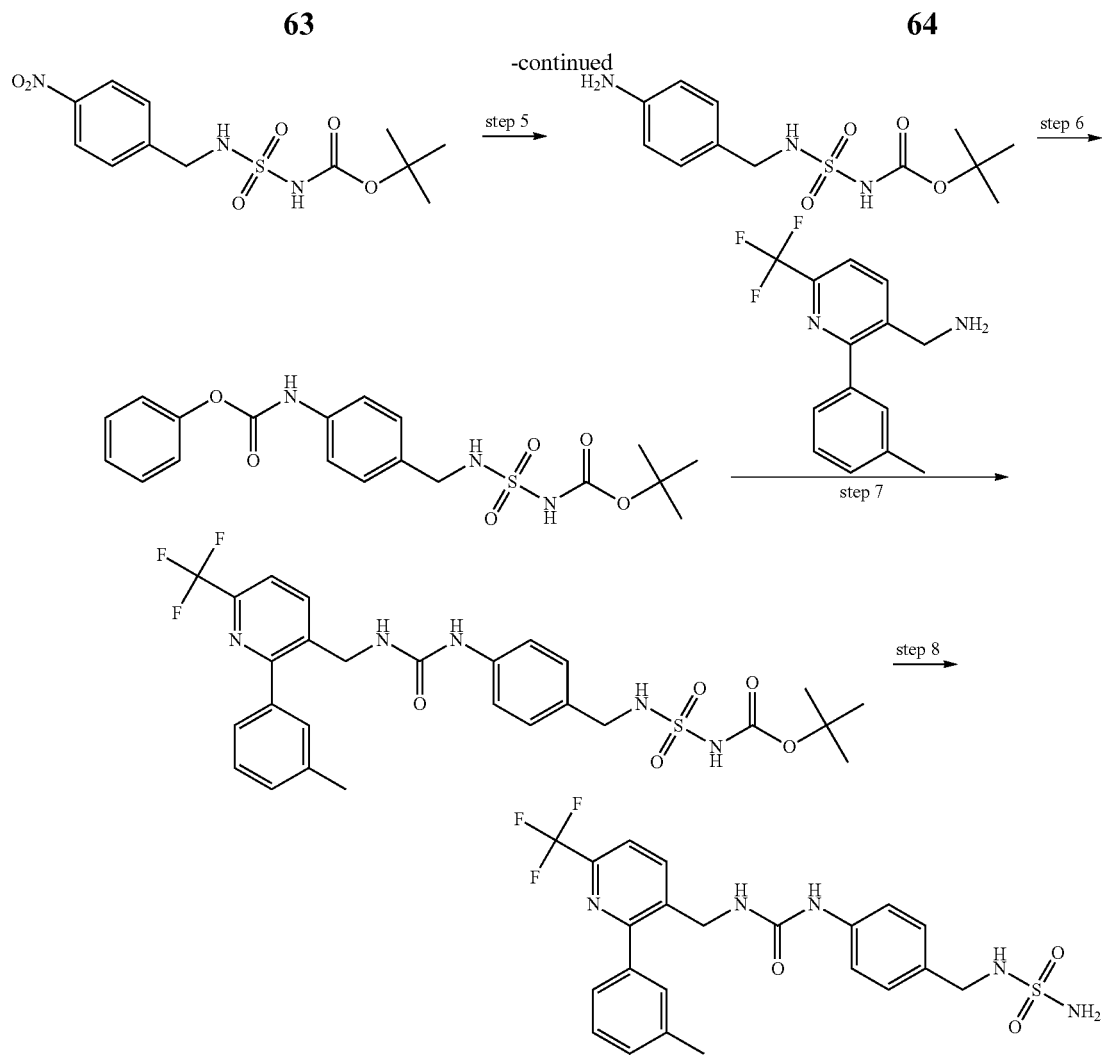

Step 1:
N-Bromosuccinimide (1.51 g, 8.509 mmol) was added to a solution of 1-methyl-4-nitrobenzene (1.2 g, 7.735 mmol) in carbon tetrachloride. 70% benzoyl peroxide (cat. 120 mg) was added to the mixture at room temperature. The mixture was refluxed. After 24 h the mixture was extracted with ethyl acetate, dried over magnesium sulfate. Evaporation of the ethyl acetate and purification by column chromatography yielded 1-(bromomethyl)-4-nitrobenzene.

Step 2:
To a solution of 1-(bromomethyl)-4-nitrobenzene (1.1 g, 4.69 mmol) in dimethylformamide potassium phthalimide (1.9 g, 10.314 mmol) was added. The mixture was reacted for overnight, extracted with ethyl acetate and washed with brine (3×20 mL). Drying over magnesium sulfate, evaporation of the ethyl acetate and purification by column chromatography gave 2-(4-nitrobenzyl)isoindoline-1,3-dione (1.6 g, 99%).

Step 3:
To a solution of 2-(4-nitrobenzyl)isoindoline-1,3-dione (1.6 g, 5.33 mmol) in tetrahydrofuran was added hydrazine monohydrate (4 eq). The mixture was refluxed for 6 h. After cooling down to room temperature the mixture was treated with potassium bicarbonate to pH 12~13, extracted with ethyl acetate and washed with brine. Drying over magnesium sulfate, evaporation of the ethyl acetate and purification by column chromatography gave (4-nitrophenyl)methanamine (592 mg, 65%).

Step 4:
Chlorosulfonyl isocyanate (0.063 mL) and t-butanol (0.07 mL) were mixed in dichloromethane. After 10 min a solution of (4-nitrophenyl)methanamine (100 mg, 0.657 mmol) in dichloromethane was added at 50° C. After stirring for 30 min the mixture was cooled to room temperature and triethylamine (0.11 mL) was added. The mixture was stirred for 3 h, extracted with ethyl acetate and washed with brine. Drying over magnesium sulfate, evaporation of the ethyl acetate and purification by column chromatography gave tert-butyl N-(4-nitrobenzyl)sulfamoylcarbamate (112 mg, 51%).

Step 5:
10% Pd/C (7 mg) was added to a solution tert-butyl N-(4-nitrobenzyl)sulfamoyl-carbamate (65 mg) in ethanol and tetrahydrofuran and charged with H₂. After stirring the reaction mixture for 6 h, the mixture was filtered using celite and evaporated in vacuo to obtain tert-butyl N-(4-aminobenzyl)sulfamoylcarbamate (58 mg, 98%).

Step 6:
tert-Butyl N-(4-aminobenzyl)sulfamoylcarbamate (86 mg, 0.285 mmol) was dissolved in a tetrahydrofuran/acetonitrile (1:1 mixture). Pyridine (0.03 mL, 0.342 mmol) was added, followed by addition of phenylchloroformate (0.04 mL, 0.3 mmol) at 0° C. The mixture was stirred at 0° C. for 30 min and further 30 min at room temperature. The reaction mixture was extracted with ethyl acetate and washed with brine. Drying over magnesium sulfate, evaporation of the ethyl acetate and purification by column chromatography gave the N-[4-[[(tert-butoxycarbonyl-sulfamoyl)amino]methyl]-phenyl]-carbamic acid phenyl ester (59 mg, 49%).

Step 7:

N-[4-[[(tert-Butoxycarbonyl-sulfamoyl)amino]-methyl]-phenyl]-carbamic acid phenyl ester (100 mg, 0.237 mmol) was dissolved in acetonitrile and (2-m-tolyl-6-(trifluoromethyl)pyridin-3-yl)methanamine (63 mg, 0.237 mmol) and 4-dimethylaminopyridine (29 mg) were added to the solution. The reaction mixture was stirred for overnight at 50° C. The reaction mixture was extracted with ethyl acetate, washed with brine, dried over magnesium sulfate. After evaporation of the ethyl acetate and purification by column chromatography tert-butyl N-(4-(3-((2-m-tolyl-6-(trifluoromethyl)pyridin-3-yl)methyl)ureido)benzyl)sulfamoylcarbamate (50 mg, 60%) was obtained.

Step 8:

To a solution of tert-butyl N-(4-(3-((2-m-tolyl-6-(trifluoromethyl)pyridin-3-yl)methyl)ureido)benzyl)sulfamoylcarbamate (60 mg, 0.101 mmol) in dichloromethane (6 mL) trifluoracetic acid (2 mL) is added at 0° C. The mixture was stirred for 30 min at 0° C. and for 2 h more at room temperature. After neutralization by sodium bicarbonate to pH 7-8 the mixture was extracted with ethyl acetate and washed with brine. Drying over magnesium sulfate, evaporation of the ethyl acetate and purification by column chromatography gave 1-{[2-m-tolyll-6-(trifluoromethyl)pyridin-3-yl]methyl}-3-{4-[(sulfamoylamino)methyl]phenyl}urea (example 84) (35 mg, 70%) in pure form.

$^1$H-NMR (300 MHz, CD$_3$OD) δ 8.09 (d, 1H, Ar—H, J=7.68 Hz), 7.78 (d, 1H, Ar—H, J=8.04 Hz), 7.35 (m, 8H, Ar—H), 4.44 (s, 2H, CH$_2$NH), 4.12 (s, 2H, CH$_2$NH), 2.43 (s, 3H, Ar—CH$_3$).

Synthesis of Example 85

2-(3-fluoro-4-((sulfamoylamino)methyl)phenyl)-N-((2-m-tolyl-6-(trifluoromethyl)pyridin-3-yl)methyl)propanamide

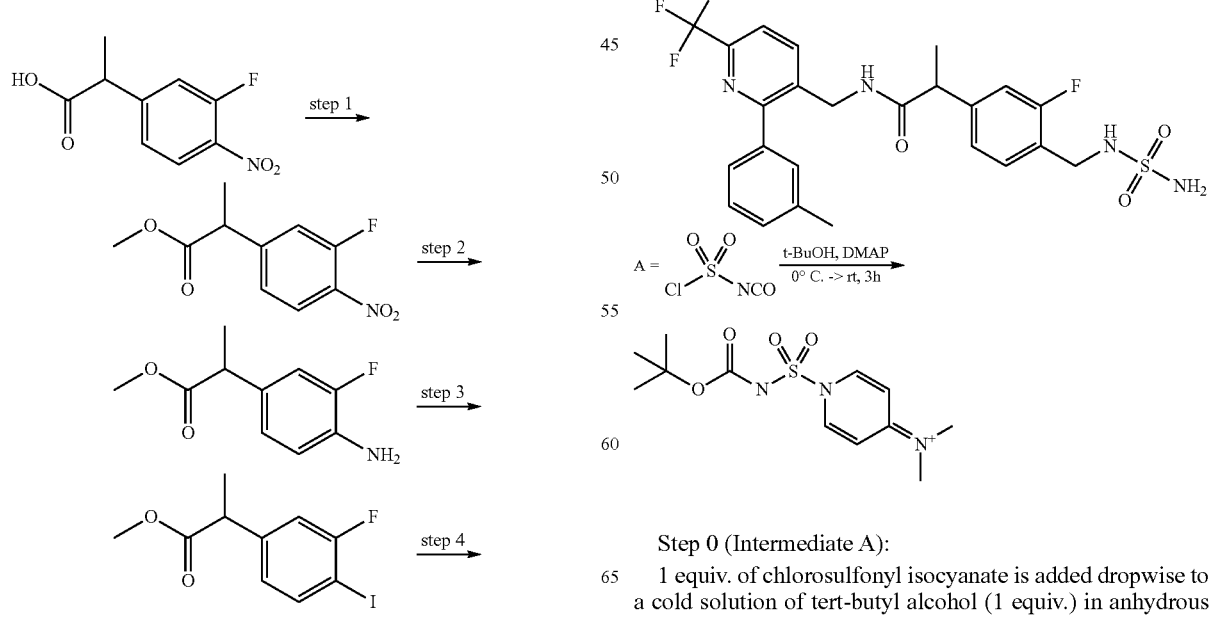

Step 0 (Intermediate A):

1 equiv. of chlorosulfonyl isocyanate is added dropwise to a cold solution of tert-butyl alcohol (1 equiv.) in anhydrous dichloromethane. Then dimethylaminopyridine (2 equiv.) is added. The mixture is stirred for 3 h at room temperature. The organic layer is extracted with dichloromethane and washed with water. After column chromatography, N-(1-(N-(tert-butoxycarbonyl)sulfamoyl)pyridin-4(1H)-ylidene)-N-methyl-methanaminium (A) as colorless powder is obtained.

Step 1:

A solution of 2-(3-fluoro-4-nitrophenyl)propanoic acid in methanol was added thionyl chloride (2.5 equiv.) at 0° C. and removed ice-bath. Reaction mixture was stirred at room temperature. After 2 h, dry over magnesium sulfate and evaporate solvent and purified by column chromatography (ethylacetate-hexane) to obtain methyl 2-(3-fluoro-4-nitrophenyl) propanoate.

Step 2:

10% Palladium on carbon is added to a solution methyl 2-(3-fluoro-4-nitrophenyl)propanoate in methanol and the mixture is charged with $H_2$ (g). After stirring the reaction mixture for 6 h, the mixture is filtered using celite packed filter and purified by column chromatography to obtain methyl 2-(4-amino-3-fluorophenyl)propanoate.

Step 3:

A solution of p-TsOH $H_2O$ (3 equiv.) in acetonitrile is added to a solution of methyl 2-(4-amino-3-fluorophenyl) propanoate (1 equiv) in acetonitrile. The resulting suspension of amine salt is cooled to 10-15° C. and to this is added, gradually, a solution of $NaNO_2$ (2 equiv.) and KI (2.5 equiv.) in water. The reaction mixture is stirred for 10 min then allowed to come to 20° C. and stirred until the starting material is consumed. After 4 h, water, $NaHCO_3$ (until pH=9-10) is added and extracted with ethyl acetate. The organic layer is washed with water, dried over magnesium sulfate and concentrated in vacuo. The residue was purified on a silica gel column using ethylacetate-hexane as solvent system to give methyl 2-(3-fluoro-4-iodophenyl)propanoate.

Step 4:

Methyl 2-(3-fluoro-4-iodophenyl)propanoate, tetrakis(triphenylphosphine) palladium(0) and zinc cyanide are placed in dimethylformamide and charged with $N_2$. The reaction mixture was stirred at 120° C. for 15 h and cooled to room temperature. The reaction mixture is filtered by celite packed filter, washed with ethyl acetate. After concentrate solvent, residue is purified on a silica gel column using ethylacetate-hexane as solvent system to give methyl 2-(4-cyano-3-fluorophenyl)propanoate.

Step 5:

A solution of methyl 2-(4-cyano-3-fluorophenyl)propanoate in tetrahydrofuran and water (1:1) is added NaOH (2.5 equiv.) and stirred at room temperature. After 15 h, the reaction mixture is acidified by acetic acid until pH=2-3. The acid is extracted with dichloromethane and water. The organic layer is washed with water, dried over magnesium sulfate and concentrated in vacuo. The product is purified column chromatography (dichloromethane:methanol=10:1) and gained 2-(4-cyano-3-fluorophenyl)propanoic acid.

Step 6:

N-(3-dimethylaminopropyl)-N'-ethylcarbodiimide (1.5 equiv), 1-hydroxybenzotriazole (1.5 equiv), and (2-m-tolyl-6-(trifluoromethyl)pyridin-3-yl)methanamine (1 equiv) are added to a solution of 2-(4-cyano-3-fluorophenyl)propanoic acid (5 equiv) drop-wise triethylamine (2.5 equiv). The reaction mixture is stirred overnight at room temperature. The reaction is quenched with water and extracted with ethyl acetate. The extracted organic layer is dried over magnesium sulfate. After evaporate solvent, purified by column chromatographic purification (ethylacetate:hexane) afforded 2-(4-cyano-3-fluorophenyl)-N-((2-m-tolyl-6-(trifluoromethyl)pyridin-3-yl)methyl)propanamide.

Step 7:

Nickel(II) chloride hexahydride (1 equiv.) and 2-(4-cyano-3-fluorophenyl)-N-((2-m-tolyl-6-(trifluoromethyl)pyridin-3-yl)methyl)propanamide are stirred in anhydrous ethanol during 15 minute for activation. Sodium borohydrid (7 equiv.) is added on it and mixture stirred for 2 h. Adding celite to the reaction and filter it using celite packed filter, washing with ethanol. The reaction mixture is purified after concentration to obtain 2-(4-(aminomethyl)-3-fluorophenyl)-N-((2-m-tolyl-6-(trifluoromethyl)pyridin-3-yl)methyl)propanamide.

Step 9:

2-(4-(Aminomethyl)-3-fluorophenyl)-N-((2-m-tolyl-6-(trifluoromethyl)pyridin-3-yl)methyl)propanamide and intermediate (A) are dissolved in dichloromethane, dropwise triethylamine (0.1 equiv.). The reaction is stirred for 15 h at room temperature and quenched with water. The organic layer is extracted by dichloromethane and concentrated. After purification, tert-butyl N-(2-fluoro-4-(1-oxo-1-((2-m-tolyl-6-(trifluoromethyl)pyridin-3-yl)methylamino)propan-2-yl)benzyl)sulfamoylcarbamate is obtained.

Step 10:

Trifluoroacetic acid (12 mL) is added to tert-butyl N-(2-fluoro-4-(1-oxo-1-((2-m-tolyl-6-(trifluoromethyl)pyridin-3-yl)methylamino)propan-2-yl)benzyl)sulfamoylcarbamate solutions in dichloromethane and the reaction is stirred for 4 h at room temperature. Water is dropped to the mixture and organic compound is extracted with dichloromethane. The mixture is purified after concentration and 2-(3-fluoro-4-((sulfamoylamino)methyl)phenyl)-N-((2-m-tolyl-6-(trifluoromethyl)pyridin-3-yl)methyl)propanamide (example 85) is obtained.

1H NMR (300 MHz, CDCl$_3$) δ 7.78 (d, 1H, J=9.00 Hz, Ar—H), 7.59 (d, 1H, J=9.00 Hz, Ar—H), 7.36-7.29 (m, 2H, Ar—H), 7.26-7.16 (m, 3H, Ar—H), 5.55 (bs, 1H, α-NH), 4.67 (bs, 1H, Ar-α-NH), 4.47 (d, 2H, J=6.00 Hz, Ar-α-CH$_2$), 4.32 (d, 2H, J=6.00 Hz, α-CH$_2$), 3.47 (m, 1H), 2.38 (s, 3H, Ar—CH$_3$), 1.44 (d, 3H, J=6.00 Hz, α-CH$_3$)

Synthesis of Example 86

1-{3-fluoro-4-[(sulfamoylamino)methyl]phenyl}-3-{[2-m-tolyl-6-(trifluoromethyl)pyridin-3-yl]methyl}urea

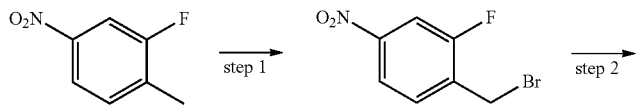

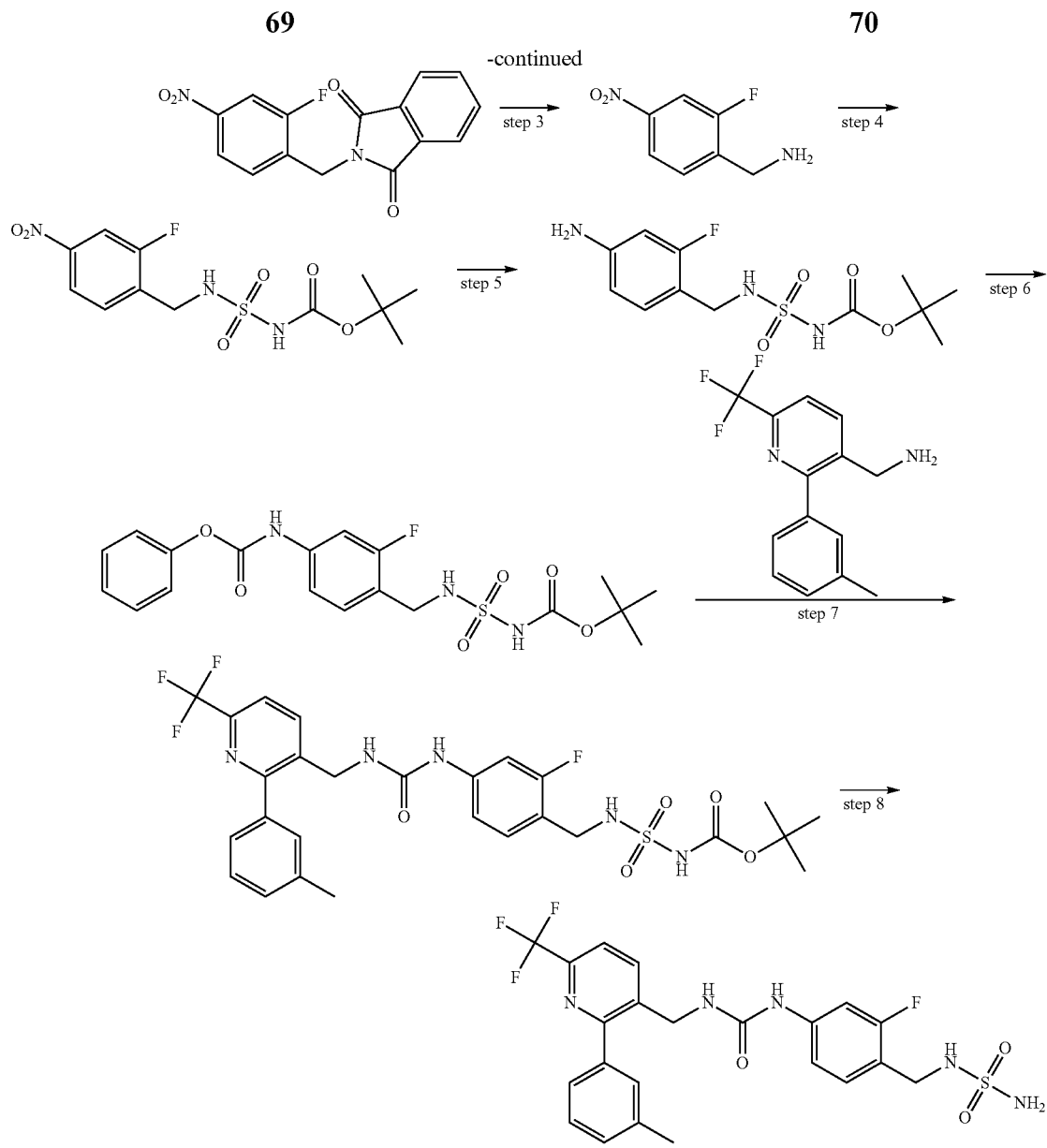

Step 1:

N-Bromosuccinimide (1.27 g, 7.09 mmol) was added to a solution of 2-fluoro-1-methyl-4-nitrobenzene (1 g, 6.446 mmol) in carbon tetrachloride. 70% benzoyl peroxide (cat. 150 mg) was added to the mixture at room temperature. The mixture was refluxed for 24 h, extracted with ethyl acetate, dryed over magnesium sulfate. After evaporation of the ethyl acetate the crude compound was purified by column chromatography to 1-(bromomethyl)-2-fluoro-4-nitrobenzene (1.05 g, 69%).

Step 2:

To a solution of 1-(bromomethyl)-2-fluoro-4-nitrobenzene (1.05 g, 4.48 mmol) in dimethylformamide potassium phthalimide (1.8 g, 9.852 mmol) was added. The mixture was reacted for overnight. Then it was extracted with ethyl acetate and washed with brine (3×20 mL). After drying over magnesium sulfate, evaporation of the ethyl acetate and purification by column chromatography 2-(2-fluoro-4-nitrobenzyl)isoindoline-1,3-dione (1.35 g, 99%) was obtained.

Step 3:

To a solution of 2-(2-fluoro-4-nitrobenzyl)isoindoline-1,3-dione (1.35 g, 4.48 mmol) in tetrahydrofurane 65% hydrazine monohydrate (1.3 mL, 4 eq) was added. The mixture was refluxed for 6 h. After the starting material was consumed, the mixture was cooled down to room temperature and treated with potassium bicarbonate to pH 12~13. Then it was extracted with ethyl acetate and washed with brine. Drying over magnesium sulfate, evaporation of the ethyl acetate and purification by column chromatography gave (2-fluoro-4-nitrophenyl)methanamine (316 mg, 41%).

Step 4:

Chlorosulfonyl isocyanate (0.1 mL) and t-butanol (0.12 mL) was mixed in dichloromethane. After 10 minutes, a solution of (2-fluoro-4-nitrophenyl)methanamine (200 mg, 1.176 mmol) in dichloromethane was added at 50° C. After stirring for 30 min the mixture was cooled to room temperature and triethylamine (0.11 mL) was added. After 3 h stirring at room temperature, the mixture was extracted with ethyl acetate and washed with brine. Drying over magnesium sulfate, evaporation of the ethyl acetate and purification by column chromatography gave tert-butyl N-(2-fluoro-4-nitrobenzyl)sulfamoylcarbamate (139 mg, 34%).

Step 5:
10% Pd/C (42 mg) was added to a solution of tert-butyl N-(2-fluoro-4-nitrobenzyl)sulfamoylcarbamate (135 mg) in ethanol and tetrahydrofuran. The mixture was charged with H₂ and stirred for 6 h. The reaction mixture was filtered using celite and evaporated in vacuo to obtain tert-butyl N-(4-amino-2-fluorobenzyl)sulfamoylcarbamate (127 mg, 99%).

Step 6:
tert-Butyl N-(4-amino-2-fluorobenzyl)sulfamoylcarbamate (127 mg, 0.398 mmol) was dissolved in tetrahydrofuran/acetonitrile. Pyridine (0.04 mL, 0.478 mmol) was added, followed by addition of phenylchloroformate (0.05 mL, 0.418 mmol) at 0° C. The mixture was stirred at 0° C. for 30 min and heated up to room temperature and stirred for 30 min. The reaction mixture was extracted with ethyl acetate and washed with brine. Drying over magnesium sulfate, evaporation of the ethyl acetate and purification by column chromatography gave 2-(N-(2-fluoro-4-(phenoxycarbonylamino)benzyl)sulfamoyl-carbamoyloxy)-2-methylpropan-1-ylium (160 mg, 91%).

Step 7:
2-(N-(2-Fluoro-4-(phenoxycarbonylamino)benzyl)sulfamoylcarbamoyloxy)-2-methylpropan-1-ylium (100 mg, 0.225 mmol) was dissolved in acetonitrile. (2-m-Tolyl-6-(trifluoromethyl)pyridin-3-yl)methanamine (60 mg, 0.225 mmol) and 4-dimethylaminopyridine (27 mg) were added to the solution. The reaction mixture was stirred for overnight at 50° C. The mixture was extracted with ethyl acetate and washed with brine. Drying over magnesium sulfate, evaporation of the ethyl acetate and purification by column chromatography gave tert-butyl N-(2-fluoro-4-(3-((2-m-tolyl-6-(trifluoromethyl)pyridin-3-yl)methyl)ureido)benzyl)sulfamoylcarbamate (70 mg, 51%).

Step 8:
To a solution of tert-butyl N-(2-fluoro-4-(3-((2-m-tolyl-6-(trifluoromethyl)pyridin-3-yl)methyl)ureido)benzyl)sulfamoylcarbamate (100 mg, 0.164 mmol) in dichloromethane (6 mL) trifluoroacetic acid (2 mL) was added at 0° C. The mixture was stirred for 30 min at 0° C. and for further 2 h at room temperature. The mixture was neutralized by sodium bicarbonate to pH 7-8 and extracted with ethyl acetate and washed with brine. Drying over magnesium sulfate, evaporation of the ethyl acetate and purification by column chromatography gave 1-{3-fluoro-4-[(sulfamoylamino)methyl]phenyl}-3-{[2-m-tolyl-6-(trifluoromethyl)pyridin-3-yl]methyl}urea (example 86) (72 mg, 86%).

¹H-NMR (300 MHz, acetone-d6): δ 8.34 (s, 1H, NH), 8.19 (d, 2H, J=8.07 Hz), 7.81 (d, 1H, Ar, J=8.07 Hz), 7.56 (dd, 1H, Ar, J¹=12.99 Hz, J²=2.01 Hz), 7.40 (m, 5H, Ar—H), 7.04 (dd, 1H, Ar, J₁=8.25 Hz, J²=1.83 Hz), 6.44 (m, 1H, NH), 5.95 (m, 2H, NH), 4.55 (d, 2H, J=5.31 Hz), 4.22 (d, 2H, J=5.67 Hz), 2.43 (s, 3H, Ar—CH₃).

Synthesis of Example 88

2-(4-((sulfamoylamino)methyl)phenyl)-N-((2-m-tolyl-6-(trifluoromethyl)pyridin-3-yl)methyl)propanamide

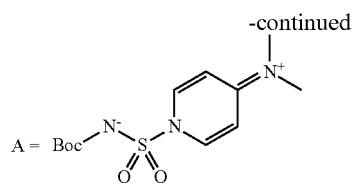

Step 0 (Intermediate A):
see example 85.

Step 1:
To a stirred solution of 2-(4-bromophenyl)acetic acid (2 g, 9.3 mmol) in ethanol (10 mL) were added sulfuric acid (0.3 mL). The reaction mixture was refluxed for overnight and cooled to room temperature. The solvent was evaporated. The residue was dissolved with ethylacetate and neutralized with NaHCO$_3$. The organic layer was washed with water two times, then dried over magnesium sulfate and filtered. The filtrate removed in vacuo. The crude was purified by column chromatography. ethyl 2-(4-bromophenyl)acetate (2.1 g) was obtained as 91% yield.

Step 2:
To a stirred solution of ethyl 2-(4-bromophenyl)acetate (2.1 g, 8.445 mmol) in anhydrous dimethylformamide were added zinc cyanide (1.5 g, 12.668 mmol) and tetrakis(triphenylphosphine) palladium (1.0 g, 0.845 mmol). The reaction mixture was refluxed for overnight then cooled to room temperature. The mixture was filtered using celite pad and the filtrate was evaporated. The residue was diluted with ethylacetate and washed with water and brine. The organic layer was dried over magnesium sulfate and filtered. The filterate was concentrated under reduced pressure to get the crude. The crude was purified by column chromatography. Ethyl 2-(4-cyanophenyl)acetate (0.8 g) was obtained as 49% yield.

Step 3:
To a stirred solution of ethyl 2-(4-cyanophenyl)acetate (0.8 g, 4.101 mmol) in anhydrous dimethylformamide were added 60% sodium hydride (180 mg, 4.511 mol) and Iodo methane were added after 10 min with an ice bath. The reaction mixture was stirred for 1 h hours, quenched with water and extracted with ethylacetate which is washed with water and brine. The organic layer was dried over magnesium sulfate and filtered. The filterate was concentrated under reduced pressure. The residue was purified by column chromatography. Ethyl 2-(4-cyanophenyl)propanoate (453 mg) was obtained as 48%

Step 4:
To a stirred solution of ethyl 2-(4-cyanophenyl)propanoate (453 mg, 1.968 mmol) in co-solvent with tetrahydrofuran and water (1:1) were added sodium hydroxide (197 mg, 4.919 mmol). The reaction mixture was stirred for overnight at room temperature, then acidified to pH 3-4 with acetic acid. The residue was diluted with ethylacetate and washed with water and brine. The organic layer was dried over magnesium sulfate and filtered. The filtrate removed in vacuo. The crude 2-(4-cyanophenyl)propanoic acid (422 mg) was obtained as 99% yield.

Step 5:
To a stirred solution of 2-(4-cyanophenyl)propanoic acid (148 mg, 0.85 mmol) in acetonitrile were added N-(3-dimethylaminopropyl)-N'-ethylcarbodiimide (243 mg, 1.27 mmol), 1-hydroxybenzotriazole (171 mg, 1.27 mmol), (2-m-tolyl-6-(trifluoromethyl)pyridin-3-yl)methanamine (247 mg, 0.93 mmol) and triethylamine (0.29 mL, 2.11 mmol). The reaction mixture was stirred for overnight at room temperature. The mixture was diluted with ethylacetate and washed with water and brine. The organic layer was dried over magnesium sulfate and filtered. The filtrate removed in vacuo. The crude was purified by column chromatography. 2-(4-Cyanophenyl)-N-((2-m-tolyl-6-(trifluoromethyl)pyridin-3-yl)methyl)propanamide (311 mg) was obtained as 87% yield.

Step 6:
To a stirred solution of 2-(4-cyanophenyl)-N-((2-m-tolyl-6-(trifluoromethyl)pyridin-3-yl)methyl)propanamide (305 mg, 0.72 mmol) in ethanol was cooled to 0° C. and added NiCl$_2$.6H$_2$O (17 mg, 0.072 mmol) and stirred more then 15 min. Sodium borohydride (191 mg, 5.04 mmol) was then added in small portions. The reaction was exothermic and effervescent. The resulting reaction mixture was allowed to warm to room temperature and left to stir for 2 hour. The mixture was filtered using celite pad. The filtrate was concentrated was evaporated. The residue was dissolved in ethylacetate and washed with water and brine, but when it does not separate easily, small amount of 1N HCl and saturated NaHCO$_3$ was used. The organic layer was dried over magnesium sulfate and filtered. The filtrate removed in vacuo. The crude was purified by column chromatography. 2-(4-(Aminomethyl)phenyl)-N-((2-m-tolyl-6-(trifluoromethyl)pyridin-3-yl)methyl)propanamide (167 mg) was obtained as 64% yield.

Step 7:
To a stirred solution of 2-(4-(aminomethyl)phenyl)-N-((2-m-tolyl-6-(trifluoromethyl)pyridin-3-yl)methyl)propanamide (167 mg, 0.39 mmol) in dichloromethane the intermediate (A) (117 mg, 0.39 mmol) and triethylamine (0.20 mL, 0.56 mmol) was added was stirred for overnight. The reaction mixture was stirred for overnight at room temperature. The mixture was diluted with dichloromethane and washed with water, brine, dried over magnesium sulfate and filtered. The filtrate was evaporated and the residue was purified by column chromatography. Tert-butyl N-(4-(1-oxo-1-((2-m-tolyl-6-(trifluoromethyl)pyridin-3-yl)methylamino)propan-2-yl)benzyl)sulfamoylcarbamate (118 mg) was obtained as 50% yield.

Step 8:
To a stirred solution of tert-butyl N-(4-(1-oxo-1-((2-m-tolyl-6-(trifluoromethyl)pyridin-3-yl)methylamino)propan-2-yl)benzyl)sulfamoylcarbamate (118 mg, 0.19 mmol) in dichloromethane (5 mL) cooled by ice bath and trifluoroacetic acid (4.0 mL) was added. The reaction mixture was stirred for overnight. The mixture was diluted with dichloromethane and then washed with NaHCO$_3$, brine, dried over magnesium sulfate and filtered. The filtrate was evaporated and purified by column chromatography. 2-(4-((Sulfamoylamino)methyl)phenyl)-N-((2-m-tolyl-6-(trifluoromethyl)pyridin-3-yl)methyl)propanamide (example 88) (79 mg) was obtained as 79% yield.

$^1$H NMR (300 MHz, CDCl$_3$) δ 7.76 (d, 1H, J=7.86 Hz), 7.58 (s, 1H, J=7.86 Hz), 7.27-7.32 (m, 3H), 7.10-7.24 (m, 5H), 5.59 (bs, 1H), 4.69 (bs, 1H), 4.58 (s, 2H), 4.44 (d, 2H, J=6.03 Hz), 4.26 (d, 2H, J=6.21 Hz), 3.50 (m, 1H), 2.38 (s, 3H), 1.46 (d, 3H, J=7.14 Hz).

Synthesis of Example 88
2-(4-((sulfamoylamino)methyl)phenyl)-N-((2-m-tolyl-6-(trifluoromethyl)pyridin-3-yl)methyl)propanamide (larger scale synthesis for chiral separation)
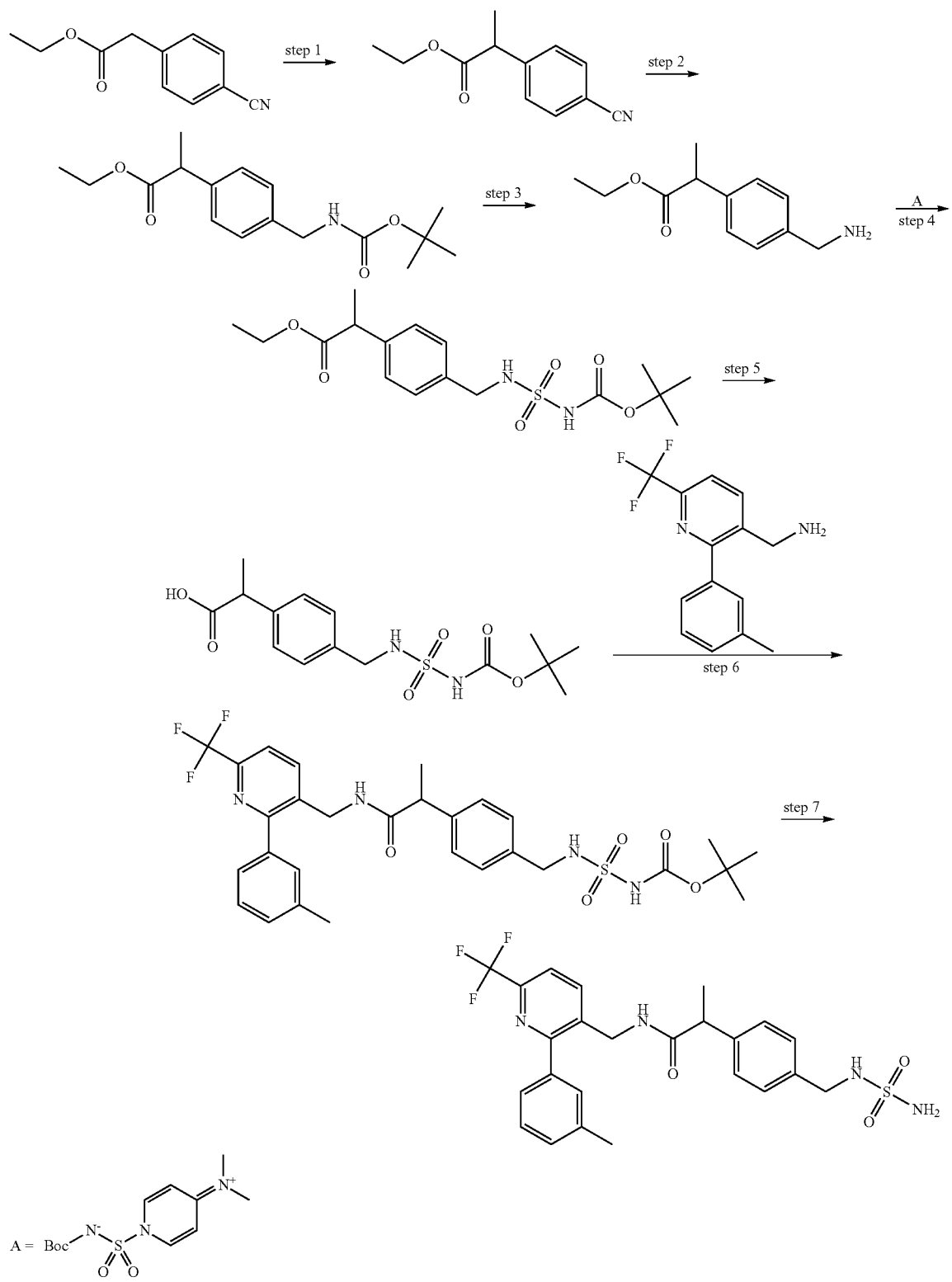

Step 0 (Intermediate A):

Chlorosulfonylisocyanate (10 g, 70.65 mmol) was added to a solution of t-butanol (6.74 mL, 70.65 mmol) in dichloromethane (50 mL) at 0° C. and stirred for 15 min. Dimethylaminopyridine (8.63 g, 70.63 mmol) was added and the reaction mixture was stirred at room temperature for 1 h. The mixture was partitioned between water (200 mL) and dichloromethane (100 mL). The organic layer was separated and the aqueous layer extracted with dichloromethane (100 mL). Combined organic layer was washed with water (4×200 mL) and brine (500 mL), dried over sodium sulfate and concentrated. Crude compound was recrystallized with acetonitrile (130 mL) to afford N-(1-(tert-butoxycarbonyl)sulfamoyl)pyridine-4(1H)-ylidene)-N-methylmethanaminium (A) (9.5 g, 45%) as a white solid.

Step 1:

Ethyl 2-(4-cyanophenyl)acetate (4.0 g, 21.14 mmol) in tetrahydrofuran (20 mL) was added to a suspension of 60% sodium hydride (850 mg, 21.14 mmol) in tetrahydrofuran (20 mL) at 0° C. and stirred for 30 min. Methyl iodide (1.36 mL, 21.14 mmol) was added at 0° C.; reaction mixture was then stirred at room temperature for 4 h. Reaction mixture quenched with saturated $NH_4Cl$ solution (20 mL), diluted with water (200 mL) and extracted with ethyl acetate (2×75 mL). The combined organic layers was washed with water (50 mL) and brine (50 mL), dried over sodium sulfate, and evaporated to get crude, which was purified by column chromatography (silica gel; 60-120 mesh); the product eluted with 10% ethyl acetate in pet ether to yield ethyl 2-(4-cyanophenyl)propanoate (3.2 g, 75%) as colorless liquid.

Step 2:

20% Pd/C (1.2 g) and di-tert-butyl dicarbonate (12.89 mL, 57.97 mmol) were added to a solution of ethyl 2-(4-cyanophenyl)propanoate (6.0 g, 28.98 mmol) in ethanol (60 mL) and hydrogenated at 60 psi at room temperature for 18 h. Reaction mixture was filtered through celite, washed with methanol (100 mL) and concentrated to give ethyl 2-(4-((tert-butoxycarbonylamino)methyl)phenyl)propanoate (6.0 g, 67%) as off white solid.

Step 3:

Trifluoroacetic acid (6 mL) was added to a solution of ethyl 2-(4-((tert-butoxycarbonylamino)methyl)phenyl)propanoate (6.0 g, 19.54 mmol) in dichloromethane (30 mL) at 0° C. and stirred for 4 h at room temperature. The volatiles were evaporated under reduced pressure, basified with saturated $NaHCO_3$ and extracted with ethyl acetate (3×50 mL). Combined organic layers washed with water (100 mL), brine solution (50 mL), dried over sodium sulfate and concentrated to give ethyl 2-(4-(aminomethyl)phenyl)propanoate (3.5 g, 86%) as colorless liquid.

Step 4:

N-(1-(tert-butoxycarbonyl)sulfamoyl)pyridine-4(1H)-ylidene)-N-methylmethanaminium (A) (5.81 g, 19.32 mmol) was added to a suspension of ethyl 2-(4-(aminomethyl)phenyl)propanoate (4.0 g, 19.32 mmol) in dichloromethane (40 mL) at room temperature and stirred for 16 h. The reaction mixture was diluted with water (100 mL) and extracted with ethyl acetate (2×75 mL). Combined organic layer was washed with water (50 mL), brine (50 mL), dried over sodium sulfate and concentrated to get crude compound, which was purified by column chromatography (silica gel; 100-200 mesh). The product eluted with 20% ethyl acetate in pet ether to yielded ethyl 2-(4-((N-(tert-butoxycarbonyl)sulfamoylamino)methyl)phenyl)propanoate (3.8 g, 51%) as pale yellow solid.

Step 5:

Lithium hydroxide monohydrate (826 mg, 19.68 mmol) in water (10 mL) was added to a solution of ethyl 2-(4-((N-(tert-butoxycarbonyl)sulfamoylamino)methyl)phenyl)propanoate (3.8 g, 9.84 mmol) in tetrahydrofuran (30 mL) at 0° C. and stirred at room temperature for 18 h. The volatiles were evaporated; the residue diluted with water (50 mL) and extracted with diethyl ether (2×20 mL). The aqueous layer was acidified (pH ~5) with acetic acid at 0° C., precipitated solid was filtered and dried under reduced pressure to afford 2-(4-((N-(tert-butoxycarbonyl)sulfamoylamino)methyl)phenyl)propanoic acid (2.3 g, 56%) as white solid.

Step 6:

2-(4-((N-(tert-butoxycarbonyl)sulfamoylamino)methyl)phenyl)propanoic acid (269 mg, 0.751 mmol) and (2-m-tolyl-6-(trifluoromethyl)pyridin-3-yl)methanamine (200 mg, 0.751 mmol) were dissolved and mixed in tetrahydrofuran (5.8 mL), followed by addition of N-hydroxybenzotriazole (103 mg, 0.751 mmol) and O-(1H-benzotriazol-1-yl)-N,N,N',N'-tetramethyluronium tetrafluorborat (238 mg, 0.751 mmol) and N-ethyldiisopropylamine (0.338 mL, 2.25 mmol). The reaction mixture was stirred for overnight at room temperature and then quenched by water and extracted with ethyl acetate. Drying over magnesium sulfate, evaporation of the ethyl acetate and purification by column chromatography gave tert-butyl N-(4-(1-oxo-1-((2-m-tolyl-6-(trifluoromethyl)pyridin-3-yl)methylamino)propan-2-yl)benzyl)sulfamoylcarbamatein pure form (258 mg, 57%).

Step 7:

To a solution of tert-butyl N-(4-(1-oxo-1-((2-m-tolyl-6-(trifluoromethyl)pyridin-3-yl)methylamino)propan-2-yl) benzyl)sulfamoylcarbamate (250 mg, 0.412 mmol) in dichloromethane (2 mL) trifluoroacetic acid (0.2 mL) was added at room temperature. The mixture was stirred 12 h at room temperature. The mixture was neutralized by sodium bicarbonate to pH 7-8 and extracted with ethyl acetate and washed with brine. Drying over magnesium sulfate, evaporation of the ethyl acetate and purification by column chromatography gave 2-(4-((sulfamoylamino)methyl)phenyl)-N-((2-m-tolyl-6-(trifluoromethyl)pyridin-3-yl)methyl)propanamide (example 88) (138 mg, 66%).

$^1$H NMR (300 MHz, $CDCl_3$) δ 7.76 (d, 1H, J=7.86 Hz), 7.58 (s, 1H, J=7.86 Hz), 7.27-7.32 (m, 3H), 7.10-7.24 (m, 5H), 5.59 (bs, 1H), 4.69 (bs, 1H), 4.58 (s, 2H), 4.44 (d, 2H, J=6.03 Hz), 4.26 (d, 2H, J=6.21 Hz), 3.50 (m, 1H), 2.38 (s, 3H), 1.46 (d, 3H, J=7.14 Hz).

Exemplary compounds 89-96 can be prepared in a similar manner according to the chiral separation described for examples 18, 19, 25 and 26.

Synthesis of Example 97

2-(3-methyl-4-(methylsulfonamidomethyl)phenyl)-N-((2-m-tolyl-6-(trifluoromethyl)pyridin-3-yl)methyl)propanamide

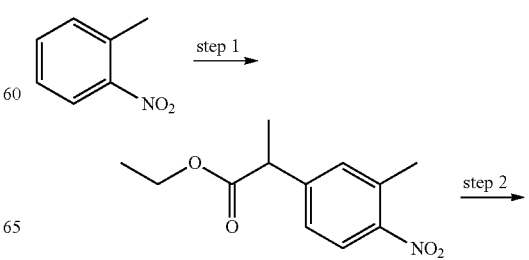

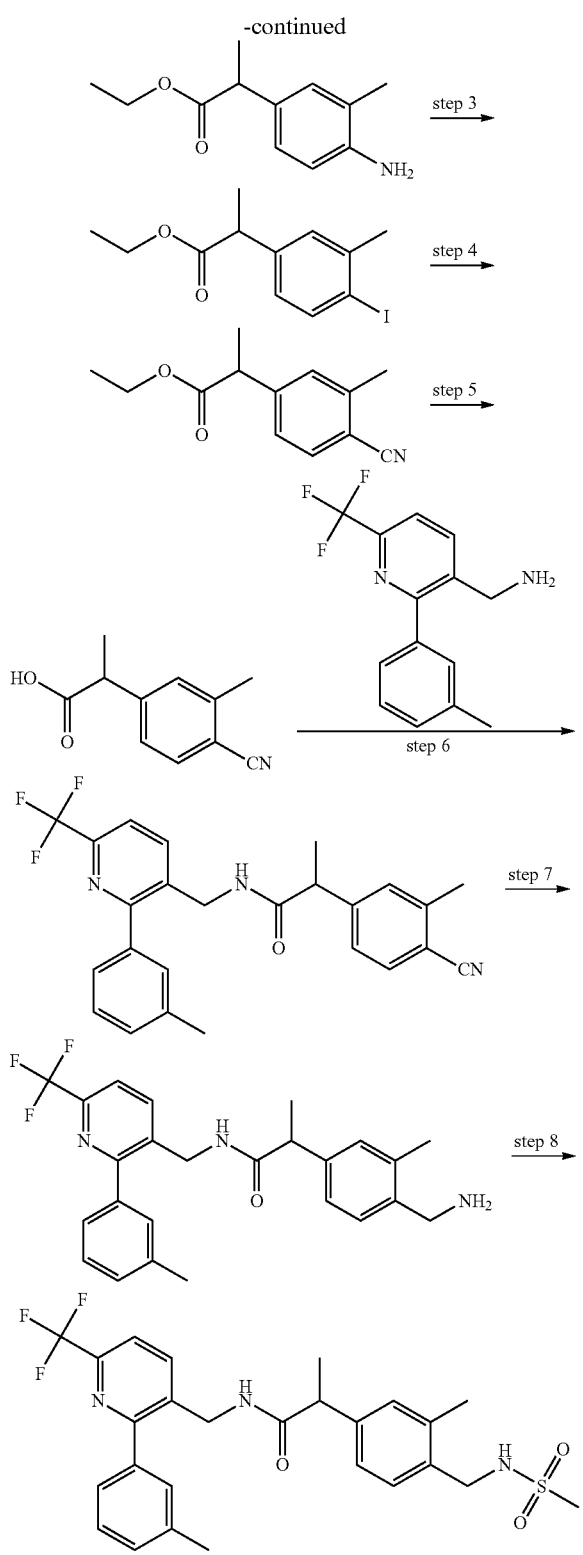

Step 1:

To a stirred solution of added potassium tertiary butoxide (2.05 g, 18.3 mmol) in dimethylformamide (10 mL) were slowly added the mixture of 1-methyl-2-nitrobenzene (1 g, 7.29 mmol) and ethyl-2-chloropropionate (0.98 mL, 7.70 mmol) at −30° C. The reaction mixture was stirred for 10 min and warmed to room temperature. The residue was dissolved with ethylacetate and neutralized with NaHCO$_3$. The organic layer was washed with water two times, then dried over magnesium sulfate and filtered. The filtrate removed in vacuo. The crude was purified by column chromatography. Ethyl 2-(3-methyl-4-nitrophenyl)propanoate (1.20 g) was obtained as 70% yield.

Step 2:

Ethyl 2-(3-methyl-4-nitrophenyl)propanoate (1.2 g, 5.05 mmol) was dissolved in methanol and tetrahydrofuran (1:1, 15 mL). 10% Pd/C (180 mg, 10%) was added to it. The resulting mixture was stirred at room temperature for 3 h under H$_2$. TLC showed complete consumption of starting material. The mixture was filtered through celite bed and the filterate was concentrated under reduced pressure. The crude was purified by column chromatography to give ethyl 2-(4-amino-3-methylphenyl)propanoate (944 mg, 90%).

Step 3:

To a stirred solution of ethyl 2-(4-amino-3-methylphenyl) propanoate (944 mg, 4.55 mmol) in acetonitrile, p-TsOH.H$_2$O (2.62 g, 13.66 mmol) was dropped slowly. The reaction mixture was activated for 10 min. Then NaNO$_2$ (629 mg, 9.11 mmol) in water was added dropwise. The mixture was stirred for 10 min. Then potassium iodide (1.89 g, 11.39 mmol) in water was added slowly dropwise. The reaction mixture was stirred at room temperature for 4 h. After the reaction is complete, 1M NaOH solution was added to neutralize the reaction then ethyl acetate and water was used for work up. The organic layer was washed with water two times, then dried over magnesium sulfate and filtered. The filtrate removed in vacuo. The crude was purified by column chromatography. Ethyl 2-(4-iodo-3-methylphenyl)propanoate (1.22 g) was obtained as 84% yield.

Step 4:

To a stirred solution of ethyl 2-(4-iodo-3-methylphenyl) propanoate (1.22 g, 5.34 mmol) in anhydrous dimethylformamide were added zinc cyanide (645 mg, 5.50 mmol) and tetrakis(triphenylphosphine) palladium (617 mg, 0.53 mmol). The reaction mixture was refluxed for overnight then cooled to room temperature. The mixture was filtered using celite pad and the filtrate was evaporated. The residue was diluted with ethylacetate and washed with water and brine. The organic layer was dried over magnesium sulfate and filtered. The filtrate was concentrated under reduced pressure to get the crude. The crude was purified by column chromatography. Ethyl 2-(4-cyano-3-methylphenyl)propanoate (1.05 g) was obtained as 90% yield.

Step 5:

To a stirred solution of ethyl 2-(4-cyano-3-methylphenyl) propanoate (1.05 g, 4.82 mmol) in co-solvent with tetrahydrofuran and water (1:1) were added sodium hydroxide (482 mg, 12.06 mmol). The reaction mixture was stirred for overnight at room temperature, then acidified to pH 3~4 with acetic acid. The residue was diluted with ethylacetate and washed with water and brine. The organic layer was dried over magnesium sulfate and filtered. The filtrate removed in vacuo. The crude 2-(4-cyano-3-methylphenyl)propanoic acid (1.1 g) was obtained as 99% yield.

Step 6:

To a stirred solution of 2-(4-cyano-3-methylphenyl)propanoic acid (100 mg, 0.53 mmol) in acetonitrile were added N-(3-dimethylaminopropyl)-N'-ethylcarbodiimide (152 mg, 0.80 mmol), 1-hydroxybenzotriazole (107 mg, 0.80 mmol), (2-m-tolyl-6-(trifluoromethyl)pyridin-3-yl)methanamine (155 mg, 0.58 mmol) and triethylamine (0.18 mL, 1.33 mmol). The reaction mixture was stirred for overnight at room temperature. The mixture was diluted with ethylacetate and washed with water and brine. The organic layer was dried over magnesium sulfate and filtered. The filtrate removed in vacuo. The crude was purified by column chromatography. 2-(4-Cyano-3-methylphenyl)-N-((2-m-tolyl-6-(trifluoromethyl)pyridin-3-yl)methyl)propanamide (152 mg) was obtained as 86% yield.

Step 7:

To a stirred solution of 2-(4-cyano-3-methylphenyl)-N-((2-m-tolyl-6-(trifluoromethyl)pyridin-3-yl)methyl)propanamide (147 mg, 0.34 mmol) in ethanol was cooled to 0° C. and added $NiCl_2.6H_2O$ (80 mg, 0.34 mmol) and stirred more than 15 mins. Sodium borohydride (81 mg, 2.35 mmol) was then added in small portions. The reaction was exothermic and effervescent. The resulting reaction mixture was allowed to warm to room temperature and left to stir for 2 h. The mixture was filtered using celite pad. The filtrate was concentrated was evaporated. The residue was dissolved in ethylacetate and washed with water and brine, but when it does not separate easily, small amount of 1N HCl and saturated $NaHCO_3$ was used. The organic layer was dried over magnesium sulfate and filtered. The filtrate removed in vacuo. The crude was purified by column chromatography. 2-(4-(Aminomethyl)-3-methylphenyl)-N-((2-m-tolyl-6-(trifluoromethyl)pyridin-3-yl)methyl)propanamide (83 mg) was obtained as 56% yield.

Step 8:

To a stirred solution of 2-(4-(aminomethyl)-3-methylphenyl)-N-((2-m-tolyl-6-(trifluoromethyl)pyridin-3-yl)methyl)propanamide (83 mg, 0.19 mmol) in pyridine was added methanesulfonyl chloride (0.02 mL, 0.24 mmol) The reaction mixture was stirred for overnight at room temperature. The mixture was diluted with ethylacetate and washed with 1N HCl and brine. The organic layer was dried over magnesium sulfate and filtered. The filtrate removed in vacuo. The crude was purified by column chromatography. 2-(3-Methyl-4-(methylsulfonamidomethyl)phenyl)-N-((2-m-tolyl-6-(trifluoromethyl)pyridin-3-yl)methyl)propanamide (example 97) (60 mg) was obtained as 61% yield.

$^1$H NMR (300 MHz, DMSO) 8.39 (bs, 1H, NH), 7.43 (d, 1H, J=7.5 Hz, Ar), 7.35 (bs, 1H, NH), 7.24 (d, 1H, J=7.8 Hz, Ar), 7.12 (m, 2H, Ar), 7.00 (d, 1H, J=7.5 Hz, Ar), 4.30 (bt, 2H, J=6.6 Hz, $CH_2$), 4.10 (s, 2H, CH), 3.63 (m, 1H, CH), 2.89 (s, 3H, Ms), 2.28 (s, 3H, $CH_3$), 1.79 (m, 4H, pyrrolidine), 1.32 (d, 3H, J=7.2 Hz, $CH_3$).

Exemplary compounds 98-101 can be prepared in a similar manner according to the procedure described for example 88.

Exemplary compounds 102-105 can be prepared in a similar manner according to the procedure described for example 85.

Mass spectrometric data are cited hereinafter by way of example for the following exemplary compounds (Table 1):

TABLE 1

| Exemplary compound | [M + H] |
| --- | --- |
| 1 | 506.1 |
| 2 | 493.1 |
| 4 | 506.2 |
| 5 | 510.0 |
| 6 | 528.1 |
| 7 | 528.1 |
| 8 | 527.9 |
| 9 | 546.1 |
| 10 | 546.1 |
| 11 | 546.1 |
| 12 | 546.1 |
| 13 | 542.1 |
| 14 | 558.1 |

TABLE 1-continued

| Exemplary compound | [M + H] |
| --- | --- |
| 15 | 544.1 |
| 16 | 561.8 |
| 17 | 562.1 |
| 18 | 562.1 |
| 19 | 524.2 |
| 20 | 496.1 |
| 21 | 511.1 |
| 22 | 523.0 |
| 23 | 512.4 |
| 24 | 524.1 |
| 25 | 524.1 |
| 26 | 524.1 |
| 27 | 510.9 |
| 29 | 524.1 |
| 30 | 538.2 |
| 31 | 538.2 |
| 32 | 538.2 |
| 33 | 538.2 |
| 34 | 542.2 |
| 35 | 542.2 |
| 36 | 542.2 |
| 37 | 542.2 |
| 39 | 549.2 |
| 42 | 554.2 |
| 43 | 554.2 |
| 44 | 554.2 |
| 45 | 554.2 |
| 46 | 568.2 |
| 47 | 568.2 |
| 48 | 554.2 |
| 49 | 554.2 |
| 50 | 552.2 |
| 51 | 566.2 |
| 52 | 560.1 |
| 55 | 553.2 |
| 57 | 535.1 |
| 58 | 535.1 |
| 59 | 526.1 |
| 60 | 540.2 |
| 61 | 539.9 |
| 62 | 540.2 |
| 64 | 554.2 |
| 67 | 511.1 |
| 68 | 541.2 |
| 69 | 541.2 |
| 71 | 525.2 |
| 72 | 525.2 |
| 73 | 545.1 |
| 77 | 540.6 |
| 78 | 536.1 |
| 80 | 522.0 |
| 81 | 507.1 |
| 82 | 506.1 |
| 83 | 537.2 |
| 84 | 493.9 |
| 85 | 525.1 |
| 86 | 512.2 |
| 88 | 507.0 |
| 97 | 498.0 |

Pharmacological Methods

I. Functional Testing Carried Out on the Vanilloid Receptor 1 (VR1/TRPV1 Receptor)

The agonistic or antagonistic effect of the substances to be tested on the rat-species vanilloid receptor 1 (VR1/TRPV1) can be determined using the following assay. In this assay, the influx of $Ca^{2+}$ through the receptor channel is quantified with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA).

Method:

Complete medium: 50 mL HAMS F12 nutrient mixture (Gibco Invitrogen GmbH, Karlsruhe, Germany) with 10% by volume of FCS (foetal calf serum, Gibco Invitrogen GmbH, Karlsruhe, Germany, heat-inactivated); 2 mM L-glutamine (Sigma, Munich, Germany); 1% by weight of AA solution (antibiotic/antimyotic solution, PAA, Pasching, Austria) and 25 ng/mL NGF medium (2.5 S, Gibco Invitrogen GmbH, Karlsruhe, Germany)

Cell culture plate: Poly-D-lysine-coated, black 96-well plates having a clear base (96-well black/clear plate, BD Biosciences, Heidelberg, Germany) are additionally coated with laminin (Gibco Invitrogen GmbH, Karlsruhe, Germany), the laminin being diluted with PBS (Ca—Mg-free PBS, Gibco Invitrogen GmbH, Karlsruhe, Germany) to a concentration of 100 μg/mL. Aliquots having a laminin concentration of 100 μg/mL are removed and stored at −20° C. The aliquots are diluted with PBS in a ratio of 1:10 to 10 μg/mL of laminin and respectively 50 μL of the solution are pipetted into a recess in the cell culture plate. The cell culture plates are incubated for at least two hours at 37° C., the excess solution is removed by suction and the recesses are each washed twice with PBS. The coated cell culture plates are stored with excess PBS which is not removed until just before the feeding of the cells.

Preparation of the Cells:

The vertebral column is removed from decapitated rats and placed immediately into cold HBSS buffer (Hank's buffered saline solution, Gibco Invitrogen GmbH, Karlsruhe, Germany), i.e. buffer located in an ice bath, mixed with 1% by volume (percent by volume) of an AA solution (antibiotic/antimyotic solution, PAA, Pasching, Austria). The vertebral column is cut longitudinally and removed together with fasciae from the vertebral canal. Subsequently, the dorsal root ganglia (DRG) are removed and again stored in cold HBSS buffer mixed with 1% by volume of an AA solution. The DRG, from which all blood remnants and spinal nerves have been removed, are transferred in each case to 500 μL of cold type 2 collagenase (PAA, Pasching, Austria) and incubated for 35 minutes at 37° C. After the addition of 2.5% by volume of trypsin (PAA, Pasching, Austria), incubation is continued for 10 minutes at 37° C. After complete incubation, the enzyme solution is carefully pipetted off and 500 μL of complete medium are added to each of the remaining DRG. The DRG are respectively suspended several times, drawn through cannulae No. 1, No. 12 and No. 16 using a syringe and transferred to a 50 mL Falcon tube which is filled up to 15 mL with complete medium. The contents of each Falcon tube are respectively filtered through a 70 μm Falcon filter element and centrifuged for 10 minutes at 1,200 rpm and room temperature. The resulting pellet is respectively taken up in 250 μL of complete medium and the cell count is determined.

The number of cells in the suspension is set to $3\times10^5$ per mL and 150 μL of this suspension are in each case introduced into a recess in the cell culture plates coated as described hereinbefore. In the incubator the plates are left for two to three days at 37° C., 5% by volume of $CO_2$ and 95% relative humidity. Subsequently, the cells are loaded with 2 μM of Fluo-4 and 0.01% by volume of Pluronic F127 (Molecular Probes Europe BV, Leiden, the Netherlands) in HBSS buffer (Hank's buffered saline solution, Gibco Invitrogen GmbH, Karlsruhe, Germany) for 30 min at 37° C., washed 3 times with HBSS buffer and after further incubation for 15 minutes at room temperature used for $Ca^{2+}$ measurement in a FLIPR assay. The $Ca^{2+}$-dependent fluorescence is in this case measured before and after the addition of substances ($\lambda$ex=488 nm, $\lambda$em=540 nm). Quantification is carried out by measuring the highest fluorescence intensity (FC, fluorescence counts) over time.

FLIPR Assay:

The FLIPR protocol consists of 2 substance additions. First the compounds to be tested (10 μM) are pipetted onto the cells and the $Ca^{2+}$ influx is compared with the control (capsaicin 10 μM). This provides the result in % activation based on the $Ca^{2+}$ signal after the addition of 10 μM of capsaicin (CP). After 5 minutes' incubation, 100 nM of capsaicin are applied and the $Ca^{2+}$ influx is also determined.

Desensitising agonists and antagonists lead to suppression of the $Ca^{2+}$ influx. The % inhibition is calculated compared to the maximum achievable inhibition with 10 μM of capsazepine.

Triple analyses (n=3) are carried out and repeated in at least 3 independent experiments (N=4).

Starting from the percentage displacement caused by different concentrations of the compounds to be tested of general formula I, $IC_{50}$ inhibitory concentrations which cause a 50-percent displacement of capsaicin were calculated. $K_i$ values for the test substances were obtained by conversion by means of the Cheng-Prusoff equation (Cheng, Prusoff; Biochem. Pharmacol. 22, 3099-3108, 1973).

Pharmacological Data

The affinity of the compounds according to the invention for the vanilloid receptor 1 (VR1/TRPV1 receptor) was determined as described herein before (pharmacological method I).

The compounds according to the invention display outstanding affinity to the VR1/TRPV1 receptor (Table 2).

In Table 2 the abbreviations below have the following meanings:

Cap=capsaicin

The value after the "@" symbol indicates the concentration at which the inhibition (as a percentage) was respectively determined.

TABLE 2

| Compound according to Example | (f) $K_i$ (human being) [nM], Cap |
|---|---|
| 1 | 44%@5 μM |
| 2 | 10 |
| 4 | 66 |
| 5 | 31 |
| 6 | 37%@5 μM |
| 7 | 61 |
| 8 | 66 |
| 9 | 47 |
| 10 | 17 |
| 11 | 41 |
| 12 | 42 |
| 13 | 26 |
| 14 | 68 |
| 15 | 10 |
| 16 | 5 |
| 17 | 4 |
| 18 | 42%@5 μM |
| 19 | 18%@1 μM |
| 20 | 45 |
| 21 | 37 |
| 22 | 23 |
| 23 | 24 |
| 24 | 6 |
| 25 | 15 |
| 26 | 33%@5 μM |
| 27 | 10 |
| 29 | 32 |
| 30 | 41 |
| 31 | 28 |
| 32 | 22 |
| 33 | 35%@5 μM |
| 34 | 27 |

TABLE 2-continued

| Compound according to Example | (f) $K_i$ (human being) [nM], Cap |
|---|---|
| 35 | 7 |
| 36 | 63 |
| 37 | 16 |
| 39 | 66 |
| 42 | 65 |
| 43 | 35 |
| 44 | 106 |
| 45 | 15%@1 µM |
| 46 | 12 |
| 47 | 37 |
| 48 | 15%@1 µM |
| 49 | 28 |
| 50 | 2 |
| 51 | 1 |
| 52 | 7 |
| 55 | 42 |
| 57 | 74 |
| 58 | 45 |
| 59 | 20%@5 µM |
| 60 | 43 |
| 61 | 53 |
| 62 | 59 |
| 64 | 28 |
| 67 | 15%@5 µM |
| 68 | 72 |
| 69 | 49%@5 µM |
| 71 | 19%@5 µM |
| 72 | 27%@5 µM |
| 73 | 24 |
| 77 | 3 |
| 78 | 73 |
| 80 | 68 |
| 81 | 7 |
| 82 | 23 |
| 83 | 74 |
| 84 | 9 |
| 85 | 3 |
| 86 | 6 |
| 88 | 7 |
| 97 | 4 |

The invention claimed is:

1. A substituted compound of formula (I),

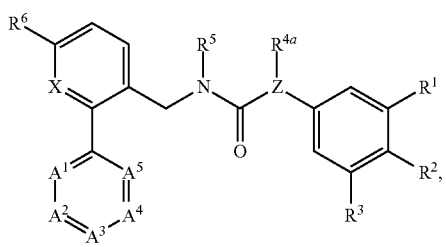

(I)

wherein
one of residues $R^1$ and $R^2$ denotes $CH_2$—$N(R^7)$—$S(=O)_2$—$R^8$,
wherein $R^7$ represents H, $CH_3$ or $C_2H_5$, and
wherein $R^8$ represents $NH_2$, $CH_3$ or $C_2H_5$,
and the respective remaining residue of $R^1$ and $R^2$ is selected from the group: consisting of H, F, Cl, Br, I, $CH_3$, $CH_2$—OH, $CH_2$—$CH_2$—OH, $CH_2$—O—$CH_3$, $CH_2$—$CH_2$—O—$CH_3$, $CF_3$, OH, O—$CH_3$, O—$CH_2$—OH, O—$CH_2$—$CH_2$—O—$CH_3$, O—$C_2H_5$, O—$CH_2$—$CH_2$—OH, O—$CH_2$—$CH_2$—O—$CH_3$ and $NH_2$;
$R^3$ is selected from the group consisting of H, F, Cl, Br, I, $CH_3$, $CF_3$, OH, O—$CH_3$, O—$CF_3$, and $NH_2$;

Z represents N or C—$R^{4b}$,
wherein $R^{4b}$ represents H or $CH_3$;
$R^{4a}$ represents H or $CH_3$;
$R^5$ represents H or $CH_3$;
X represents N or CH;
$R^6$ represents $CF_3$, an unsubstituted, saturated $C_{1-4}$ aliphatic residue or an unsubstituted, saturated $C_{3-6}$ cycloaliphatic residue;
$A^1$ represents N or $CR^9$;
$A^2$ represents N or $CR^{10}$;
$A^3$ represents N or $CR^{11}$;
$A^4$ represents N or $CR^{12}$;
$A^5$ represents N or $CR^{13}$;
with the proviso that 0, 1, 2 or 3 of variables $A^1, A^2, A^3, A^4$ and $A^5$ represent(s) a nitrogen atom, and
$R^9, R^{10}, R^{11}, R^{12}$, and $R^{13}$ each independently of one another represent H, F, Cl, Br, I, CN, $NO_2$, $CF_3$, $CF_2H$, $CFH_2$, OH, $OCF_3$, $NH_2$; a $C_{1-4}$ aliphatic residue, an O—$C_{1-4}$ aliphatic residue, a NH—$C_{1-4}$ aliphatic residue, and a N($C_{1-4}$ aliphatic residue)$_2$, wherein the $C_{1-4}$ aliphatic residue can in each case be unsubstituted or mono-, di- or trisubstituted with 1, 2 or 3 substituents selected independently of one another from the group consisting of OH, O—$CH_3$, O—$CH_2$—OH, O—$CH_2$—O—$CH_3$, O—$C_2H_5$, O—$C_2H_4$—OH, O—$C_2H_4$—O—$CH_3$, O—$CF_3$, $NH_2$, $NH(CH_3)$, and $N(CH_3)_2$;
in which an "aliphatic residue" can be branched or unbranched, saturated or unsaturated, if not indicated otherwise;
optionally in the form of a single stereoisomer or a mixture of stereoisomers, in the form of the free compound and/or a physiologically acceptable salt thereof.

2. The substituted compound according to claim 1, wherein one of residues $R^1$ and $R^2$ denotes $CH_2$—$N(R^7)$—$S(=O)_2$—$R^8$,
wherein $R^7$ represents H, $CH_3$, or $C_2H_5$, and
wherein $R^8$ represents $NH_2$, $CH_3$, or $C_2H_5$,
and the respective remaining residue of $R^1$ and $R^2$ is selected from the group consisting of H, F, Cl, Br, I, $CH_3$, $CH_2$—OH, $CH_2$—O—$CH_3$, $CF_3$, OH, and O—$CH_3$.

3. The substituted compound according to claim 1, wherein $R^2$ denotes $CH_2$—$N(R^7)$—$S(=O)_2$—$R^8$,
wherein $R^7$ represents H, $CH_3$, or $C_2H_5$, and
wherein $R^8$ represents $NH_2$, $CH_3$, or $C_2H_5$,
and $R^1$ is selected from the group consisting of H, F, Cl, Br, I, $CH_3$, $CH_2$—OH, $CH_2$—O—$CH_3$, $CF_3$, OH, and O—$CH_3$.

4. The substituted compound according to claim 1, wherein $R^3$ is selected from the group consisting of H, F, Cl, $CH_3$, $CF_3$, OH and 0-$CH_3$.

5. The substituted compound according to claim 1, wherein
Z represents N and
$R^{4a}$ represents H,
or
Z represents C—$R^{4b}$,
wherein $R^{4b}$ represents H or $CH_3$, and
$R^{4a}$ represents H.

6. The substituted compound according to claim 1, wherein X represents N.

7. The substituted compound according to claim 1, wherein $R^6$ represents $CF_3$, tert.-Butyl or cyclopropyl.

8. The substituted compound according to claim 1, wherein the substructure (T1) of formula (I)
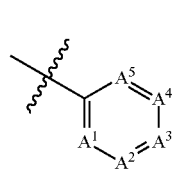
(T1)
is selected from the group consisting of (T1-a), (T1-b), (T1-c), (T1-d), (T1-e), (T1-f), (T1-g), (T1-h), (T1-i), (T1-j), (T1-k), (T1-m), (T1-n), (T1-o), (T1-p) and (T1-q),
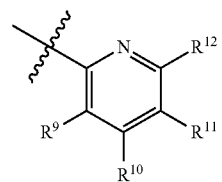
(T1-a)
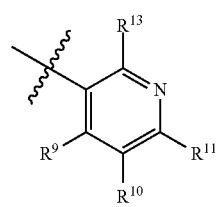
(T1-b)
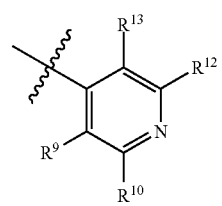
(T1-c)
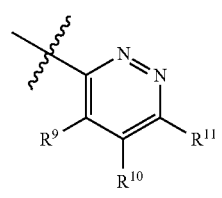
(T1-d)
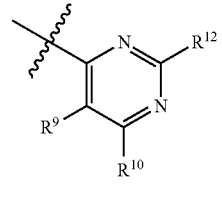
(T1-e)
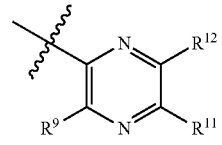
(T1-f)
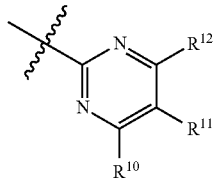
(T1-g)
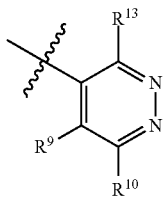
(T1-h)
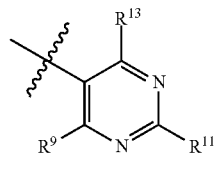
(T1-i)
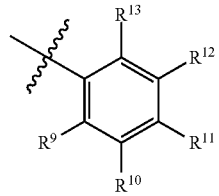
(T1-j)
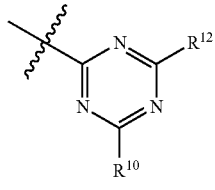
(T1-k)
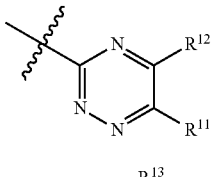
(T1-m)
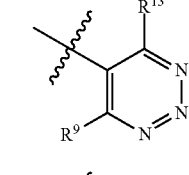
(T1-n)
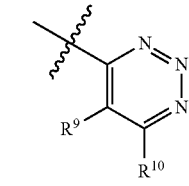
(T1-o)
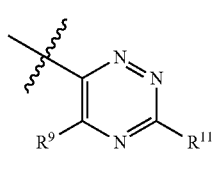
(T1-p)

-continued (T1-q)

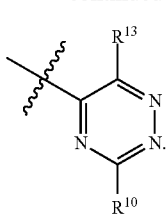

9. The substituted compound according to claim 1, wherein
$A^1$ represents $CR^9$;
$A^2$ represents $CR^{10}$;
$A^3$ represents $CR^{11}$;
$A^4$ represents $CR^{12}$; and
$A^5$ represents $CR^{13}$.

10. The substituted compound according to claim 1, wherein
$R^9$, $R^{10}$, $R^{11}$, $R^{12}$, and $R^{13}$ each independently of one another represent
H, F, Cl, Br, I, CN, $NO_2$, $CF_3$, $CF_2H$, $CFH_2$, OH, $OCF_3$, $NH_2$, or
a $C_{1-4}$ aliphatic residue, an $O—C_{1-4}$ aliphatic residue, a $NH—C_{1-4}$ aliphatic residue, or a $N(C_{1-4}$ aliphatic residue$)_2$, wherein the $C_{1-4}$ aliphatic residue can in each case be unsubstituted or mono-, di- or trisubstituted with 1, 2 or 3 substituents selected independently of one another from the group consisting of OH, $O—CH_3$, and $O—C_2H_5$.

11. The substituted compound according to claim 1, wherein
one of residues $R^1$ and $R^2$ denotes $CH_2—N(R^7)—S(=O)_2—R^8$,
wherein $R^7$ represents H, $CH_3$, or $C_2H_5$, and
wherein $R^8$ represents $NH_2$, $CH_3$, or $C_2H_5$,
and the respective remaining residue of $R^1$ and $R^2$ is selected from the group consisting of H, F, Cl, Br, I, $CH_3$, $CH_2—OH$, $CH_2—O—CH_3$, $CF_3$, OH, and $O—CH_3$;
$R^3$ is selected from the group consisting of H, F, Cl, $CH_3$, and $O—CH_3$;
Z represents N and
$R^{4a}$ represents H,
or
Z represents $C—R^{4b}$,
wherein $R^{4b}$ represents H or $CH_3$, and
$R^{4a}$ represents H;
$R^5$ represents H;
X represents N or CH;
$R^6$ represents $CF_3$, tert.-Butyl or cyclopropyl;
$A^1$ represents N or $CR^9$;
$A^2$ represents N or $CR^{10}$;
$A^3$ represents N or $CR^{11}$;
$A^4$ represents N or $CR^{12}$;
$A^5$ represents N or $CR^{13}$;
with the proviso that 0, 1 or 2 of variables $A^1$, $A^2$, $A^3$, $A^4$ and $A^5$ represent(s) a nitrogen atom, and
$R^9$, $R^{10}$, $R^{11}$, $R^{12}$, and $R^{13}$ each independently of one another represent
H, F, Cl, Br, I, CN, $NO_2$, $CF_3$, $CF_2H$, $CFH_2$, OH, $OCF_3$, $NH_2$, methyl, ethyl, n-propyl, 2-propyl, n-butyl, isobutyl, sec.-butyl, tert.-butyl, $CH_2—OH$, $C_2H_4—OH$, $CH_2—OCH_3$, $C_2H_4—OCH_3$, $OCH_3$, $O—C_2H_5$, $NH(CH_3)$ or $N(CH_3)_2$.

12. The substituted compound according to claim 1 selected from the group consisting of 1   2-(3-(methylsulfonamidomethyl)phenyl)-N-((2-m-tolyl-6-(trifluoromethyl)pyridin-3-yl)methyl)propanamide;
2   N-(4-(3-((2-m-tolyl-6-(trifluoromethyl)pyridin-3-yl)methyl)ureido)benzyl)methanesulfonamide;
3   2-(4-(methylsulfonamidomethyl)phenyl)-N-((2-m-tolyl-6-(trifluoromethyl)pyridin-3-yl)methyl)acetamide;
4   2-(4-(methylsulfonamidomethyl)phenyl)-N-((2-m-tolyl-6-(trifluoromethyl)pyridin-3-yl)methyl)propanamide;
5   2-(3-fluoro-4-(methylsulfonamidomethyl)phenyl)-N-((2-phenyl-6-(trifluoromethyl)pyridin-3-yl)methyl)propanamide;
6   2-(3-fluoro-4-(methylsulfonamidomethyl)phenyl)-N-((2-(2-fluorophenyl)-6-(trifluoromethyl)pyridin-3-yl)methyl)propanamide;
7   2-(3-fluoro-4-(methylsulfonamidomethyl)phenyl)-N-((2-(3-fluorophenyl)-6-(trifluoromethyl)pyridin-3-yl)methyl)propanamide;
8   2-(3-fluoro-4-(methylsulfonamidomethyl)phenyl)-N-((2-(4-fluorophenyl)-6-(trifluoromethyl)pyridin-3-yl)methyl)propanamide;
9   N-((2-(2,3-difluorophenyl)-6-(trifluoromethyl)pyridin-3-yl)methyl)-2-(3-fluoro-4-(methylsulfonamidomethyl)phenyl)propanamide;
10  N-((2-(3,4-difluorophenyl)-6-(trifluoromethyl)pyridin-3-yl)methyl)-2-(3-fluoro-4-(methylsulfonamidomethyl)phenyl)propanamide;
11  N-((2-(3,5-difluorophenyl)-6-(trifluoromethyl)pyridin-3-yl)methyl)-2-(3-fluoro-4-(methylsulfonamidomethyl)phenyl)propanamide;
12  N-((2-(2,5-difluorophenyl)-6-(trifluoromethyl)pyridin-3-yl)methyl)-2-(3-fluoro-4-(methylsulfonamidomethyl)phenyl)propanamide;
13  2-(3-fluoro-4-(methylsulfonamidomethyl)phenyl)-N-((2-(3-fluoro-4-methylphenyl)-6-(trifluoromethyl)pyridin-3-yl)methyl)propanamide;
14  2-(3-fluoro-4-(methylsulfonamidomethyl)phenyl)-N-((2-(3-fluoro-4-methoxyphenyl)-6-(trifluoromethyl)pyridin-3-yl)methyl)propanamide;
15  N-((2-(3-chlorophenyl)-6-(trifluoromethyl)pyridin-3-yl)methyl)-2-(3-fluoro-4-(methylsulfonamidomethyl)phenyl)propanamide;
16  N-((2-(3-chloro-4-fluorophenyl)-6-(trifluoromethyl)pyridin-3-yl)methyl)-2-(3-fluoro-4-(methylsulfonamidomethyl)phenyl)propanamide;
17  (S)—N-((2-(3-chloro-4-fluorophenyl)-6-(trifluoromethyl)pyridin-3-yl)methyl)-2-(3-fluoro-4-(methylsulfonamidomethyl)phenyl)propanamide;
18  (R)—N-((2-(3-chloro-4-fluorophenyl)-6-(trifluoromethyl)pyridin-3-yl)methyl)-2-(3-fluoro-4-(methylsulfonamidomethyl)phenyl)propanamide;
19  2-(3-fluoro-4-(methylsulfonamidomethyl)phenyl)-N-((2-o-tolyl-6-(trifluoromethyl)pyridin-3-yl)methyl)propanamide;
20  N-((6-cyclopropyl-2-m-tolylpyridin-3-yl)methyl)-2-(3-fluoro-4-(methylsulfonamidomethyl)phenyl)propanamide;
21  N-((5-tert-butyl-3'-methylbiphenyl-2-yl)methyl)-2-(3-fluoro-4-(methylsulfonamidomethyl)phenyl)propanamide;
22  2-(3-fluoro-4-(methylsulfonamidomethyl)phenyl)-N-((3'-methyl-5-(trifluoromethyl)biphenyl-2-yl)methyl)propanamide;

23 N-((6-tert-butyl-2-m-tolylpyridin-3-yl)methyl)-2-(3-fluoro-4-(methylsulfonamidomethyl)phenyl)propanamide;

24 2-(3-fluoro-4-(methylsulfonamidomethyl)phenyl)-N-((2-m-tolyl-6-(trifluoromethyl)pyridin-3-yl)methyl)propanamide;

25 (S)-2-(3-fluoro-4-(methylsulfonamidomethyl)phenyl)-N-((2-m-tolyl-6-(trifluoromethyl)pyridin-3-yl)methyl)propanamide;

26 (R)-2-(3-fluoro-4-(methylsulfonamidomethyl)phenyl)-N-((2-m-tolyl-6-(trifluoromethyl)pyridin-3-yl)methyl)propanamide;

27 N-(2-fluoro-4-(3-((2-m-tolyl-6-(trifluoromethyl)pyridin-3-yl)methyl)ureido)benzyl)methanesulfonamide;

28 2-(3-fluoro-4-(methylsulfonamidomethyl)phenyl)-N-((2-m-tolyl-6-(trifluoromethyl)pyridin-3-yl)methyl)acetamide;

29 2-(3-fluoro-4-(methylsulfonamidomethyl)phenyl)-N-((2-p-tolyl-6-(trifluoromethyl)pyridin-3-yl)methyl)propanamide;

30 N-((2-(2,3-dimethylphenyl)-6-(trifluoromethyl)pyridin-3-yl)methyl)-2-(3-fluoro-4-(methylsulfonamidomethyl)phenyl)propanamide;

31 N-((2-(3,4-dimethylphenyl)-6-(trifluoromethyl)pyridin-3-yl)methyl)-2-(3-fluoro-4-(methylsulfonamidomethyl)phenyl)propanamide;

32 N-((2-(3,5-dimethylphenyl)-6-(trifluoromethyl)pyridin-3-yl)methyl)-2-(3-fluoro-4-(methylsulfonamidomethyl)phenyl)propanamide;

33 N-((2-(2,5-dimethylphenyl)-6-(trifluoromethyl)pyridin-3-yl)methyl)-2-(3-fluoro-4-(methylsulfonamidomethyl)phenyl)propanamide;

34 N-((2-(2-fluoro-3-methylphenyl)-6-(trifluoromethyl)pyridin-3-yl)methyl)-2-(3-fluoro-4-(methylsulfonamidomethyl)phenyl)propanamide;

35 N-((2-(4-fluoro-3-methylphenyl)-6-(trifluoromethyl)pyridin-3-yl)methyl)-2-(3-fluoro-4-(methylsulfonamidomethyl)phenyl)propanamide;

36 2-(3-fluoro-4-(methylsulfonamidomethyl)phenyl)-N-((2-(3-fluoro-5-methylphenyl)-6-(trifluoromethyl)pyridin-3-yl)methyl)propanamide;

37 2-(3-fluoro-4-(methylsulfonamidomethyl)phenyl)-N-((2-(2-fluoro-5-methylphenyl)-6-(trifluoromethyl)pyridin-3-yl)methyl)propanamide;

38 N-((2-(2-cyano-3-methylphenyl)-6-(trifluoromethyl)pyridin-3-yl)methyl)-2-(3-fluoro-4-(methylsulfonamidomethyl)phenyl)propanamide;

39 N-((2-(4-cyano-3-methylphenyl)-6-(trifluoromethyl)pyridin-3-yl)methyl)-2-(3-fluoro-4-(methylsulfonamidomethyl)phenyl)propanamide;

40 N-((2-(3-cyano-5-methylphenyl)-6-(trifluoromethyl)pyridin-3-yl)methyl)-2-(3-fluoro-4-(methylsulfonamidomethyl)phenyl)propanamide;

41 N-((2-(2-cyano-5-methylphenyl)-6-(trifluoromethyl)pyridin-3-yl)methyl)-2-(3-fluoro-4-(methylsulfonamidomethyl)phenyl)propanamide;

42 2-(3-fluoro-4-(methylsulfonamidomethyl)phenyl)-N-((2-(2-methoxy-3-methylphenyl)-6-(trifluoromethyl)pyridin-3-yl)methyl)propanamide;

43 2-(3-fluoro-4-(methylsulfonamidomethyl)phenyl)-N-((2-(4-methoxy-3-methylphenyl)-6-(trifluoromethyl)pyridin-3-yl)methyl)propanamide;

44 2-(3-fluoro-4-(methylsulfonamidomethyl)phenyl)-N-((2-(3-methoxy-5-methylphenyl)-6-(trifluoromethyl)pyridin-3-yl)methyl)propanamide;

45 2-(3-fluoro-4-(methylsulfonamidomethyl)phenyl)-N-((2-(2-methoxy-5-methylphenyl)-6-(trifluoromethyl)pyridin-3-yl)methyl)propanamide;

46 N-((2-(4-ethoxy-3-methylphenyl)-6-(trifluoromethyl)pyridin-3-yl)methyl)-2-(3-fluoro-4-(methylsulfonamidomethyl)phenyl)propanamide;

47 N-((2-(3-ethoxy-5-methylphenyl)-6-(trifluoromethyl)pyridin-3-yl)methyl)-2-(3-fluoro-4-(methylsulfonamidomethyl)phenyl)propanamide;

48 N-((2-(2-ethoxy-5-methylphenyl)-6-(trifluoromethyl)pyridin-3-yl)methyl)-2-(3-fluoro-4-(methylsulfonamidomethyl)phenyl)propanamide;

49 2-(3-fluoro-4-(methylsulfonamidomethyl)phenyl)-N-((2-(3-(methoxymethyl)phenyl)-6-(trifluoromethyl)pyridin-3-yl)methyl)propanamide;

50 2-(3-fluoro-4-(methylsulfonamidomethyl)phenyl)-N-((2-(3-isopropylphenyl)-6-(trifluoromethyl)pyridin-3-yl)methyl)propanamide;

51 N-((2-(3-tert-butylphenyl)-6-(trifluoromethyl)pyridin-3-yl)methyl)-2-(3-fluoro-4-(methylsulfonamidomethyl)phenyl)propanamide;

52 N-((2-(3-(difluoromethyl)phenyl)-6-(trifluoromethyl)pyridin-3-yl)methyl)-2-(3-fluoro-4-(methylsulfonamidomethyl)phenyl)propanamide;

53 2-(3-fluoro-4-(methylsulfonamidomethyl)phenyl)-N-((6-(trifluoromethyl)-2-(3-(trifluoromethyl)phenyl)pyridin-3-yl)methyl)propanamide;

54 2-(3-fluoro-4-(methylsulfonamidomethyl)phenyl)-N-((2-(3-(trifluoromethoxy)phenyl)-6-(trifluoromethyl)pyridin-3-yl)methyl)propanamide;

55 N-((2-(3-(dimethylamino)phenyl)-6-(trifluoromethyl)pyridin-3-yl)methyl)-2-(3-fluoro-4-(methylsulfonamidomethyl)phenyl)propanamide;

56 N-((2-(2-cyanophenyl)-6-(trifluoromethyl)pyridin-3-yl)methyl)-2-(3-fluoro-4-(methylsulfonamidomethyl)phenyl)propanamide;

57 N-((2-(3-cyanophenyl)-6-(trifluoromethyl)pyridin-3-yl)methyl)-2-(3-fluoro-4-(methylsulfonamidomethyl)phenyl)propanamide;

58 N-((2-(4-cyanophenyl)-6-(trifluoromethyl)pyridin-3-yl)methyl)-2-(3-fluoro-4-(methylsulfonamidomethyl)phenyl)propanamide;

59 2-(3-fluoro-4-(methylsulfonamidomethyl)phenyl)-N-((2-(3-hydroxyphenyl)-6-(trifluoromethyl)pyridin-3-yl)methyl)propanamide;

60 2-(3-fluoro-4-(methylsulfonamidomethyl)phenyl)-N-((2-(2-methoxyphenyl)-6-(trifluoromethyl)pyridin-3-yl)methyl)propanamide;

61 2-(3-fluoro-4-(methylsulfonamidomethyl)phenyl)-N-((2-(3-methoxyphenyl)-6-(trifluoromethyl)pyridin-3-yl)methyl)propanamide;

62 2-(3-fluoro-4-(methylsulfonamidomethyl)phenyl)-N-((2-(4-methoxyphenyl)-6-(trifluoromethyl)pyridin-3-yl)methyl)propanamide;

63 N-((2-(2-ethoxyphenyl)-6-(trifluoromethyl)pyridin-3-yl)methyl)-2-(3-fluoro-4-(methylsulfonamidomethyl)phenyl)propanamide;

64 N-((2-(3-ethoxyphenyl)-6-(trifluoromethyl)pyridin-3-yl)methyl)-2-(3-fluoro-4-(methylsulfonamidomethyl)phenyl)propanamide;

65 N-((2-(4-ethoxyphenyl)-6-(trifluoromethyl)pyridin-3-yl)methyl)-2-(3-fluoro-4-(methylsulfonamidomethyl)phenyl)propanamide;

66 2-(3-fluoro-4-(methylsulfonamidomethyl)phenyl)-N-((6-(trifluoromethyl)-2,2'-bipyridin-3-yl)methyl)propanamide;

67 2-(3-fluoro-4-(methylsulfonamidomethyl)phenyl)-N-((6-(trifluoromethyl)-2,3'-bipyridin-3-yl)methyl)propanamide;
68 2-(3-fluoro-4-(methylsulfonamidomethyl)phenyl)-N-((6'-methoxy-6-(trifluoromethyl)-2,3'-bipyridin-3-yl)methyl)propanamide;
69 2-(3-fluoro-4-(methylsulfonamidomethyl)phenyl)-N-((5'-methoxy-6-(trifluoromethyl)-2,3'-bipyridin-3-yl)methyl)propanamide;
70 2-(3-fluoro-4-(methylsulfonamidomethyl)phenyl)-N-((4'-methoxy-6-(trifluoromethyl)-2,3'-bipyridin-3-yl)methyl)propanamide;
71 2-(3-fluoro-4-(methylsulfonamidomethyl)phenyl)-N-((2'-methyl-6-(trifluoromethyl)-2,3'-bipyridin-3-yl)methyl)propanamide;
72 2-(3-fluoro-4-(methylsulfonamidomethyl)phenyl)-N-((6'-methyl-6-(trifluoromethyl)-2,3'-bipyridin-3-yl)methyl)propanamide;
73 N-((5'-chloro-6-(trifluoromethyl)-2,3'-bipyridin-3-yl)methyl)-2-(3-fluoro-4-(methylsulfonamidomethyl)phenyl)propanamide;
74 N-((4'-chloro-6-(trifluoromethyl)-2,3'-bipyridin-3-yl)methyl)-2-(3-fluoro-4-(methylsulfonamidomethyl)phenyl)propanamide;
75 2-(3-fluoro-4-(methylsulfonamidomethyl)phenyl)-N-((2-(5-methylpyrazin-2-yl)-6-(trifluoromethyl)pyridin-3-yl)methyl)propanamide;
76 N-(2,6-difluoro-4-(3-((2-m-tolyl-6-(trifluoromethyl)pyridin-3-yl)methyl)ureido)benzyl)methanesulfonamide;
77 2-(3-chloro-4-(methylsulfonamidomethyl)phenyl)-N-((2-m-tolyl-6-(trifluoromethyl)pyridin-3-yl)methyl)propanamide;
78 2-(3-methoxy-4-(methylsulfonamidomethyl)phenyl)-N-((2-m-tolyl-6-(trifluoromethyl)pyridin-3-yl)methyl)propanamide;
79 N-(2-hydroxy-4-(3-((2-m-tolyl-6-(trifluoromethyl)pyridin-3-yl)methyl)ureido)benzyl)methanesulfonamide;
80 N-(2-methoxy-4-(3-((2-m-tolyl-6-(trifluoromethyl)pyridin-3-yl)methyl)ureido)benzyl)methanesulfonamide;
81 N-(2-methyl-4-(3-((2-m-tolyl-6-(trifluoromethyl)pyridin-3-yl)methyl)ureido)benzyl)methanesulfonamide;
82 N-(4-(3-((2-m-tolyl-6-(trifluoromethyl)pyridin-3-yl)methyl)ureido)benzyl)ethanesulfonamide;
83 2-(4-(ethylsulfonamidomethyl)-3-fluorophenyl)-N-((2-m-tolyl-6-(trifluoromethyl)pyridin-3-yl)methyl)propanamide;
84 1-{[2-m-tolyl1-6-(trifluoromethyl)pyridin-3-yl]methyl}-3-{4-[(sulfamoylamino)methyl]phenyl}urea;
85 2-(3-fluoro-4-((sulfamoylamino)methyl)phenyl)-N-((2-m-tolyl-6-(trifluoromethyl)pyridin-3-yl)methyl)propanamide;
86 1-{3-fluoro-4-[(sulfamoylamino)methyl]phenyl}-3-{[2-m-tolyl-6-(trifluoromethyl)pyridin-3-yl]methyl}urea;
87 2-(3-fluoro-4-((N-methylmethylsulfonamido)methyl)phenyl)-N-((2-m-tolyl-6-(trifluoromethyl)pyridin-3-yl)methyl)propanamide;
88 2-(4-((sulfamoylamino)methyl)phenyl)-N-((2-m-tolyl-6-(trifluoromethyl)pyridin-3-yl)methyl)propanamide;
89 (S)-2-(4-((sulfamoylamino)methyl)phenyl)-N-((2-m-tolyl-6-(trifluoromethyl)pyridin-3-yl)methyl)propanamide;
90 (R)-2-(4-((sulfamoylamino)methyl)phenyl)-N-((2-m-tolyl-6-(trifluoromethyl)pyridin-3-yl)methyl)propanamide;
91 (S)-2-(3-fluoro-4-((sulfamoylamino)methyl)phenyl)-N-((2-m-tolyl-6-(trifluoromethyl)pyridin-3-yl)methyl)propanamide;
92 (R)-2-(3-fluoro-4-((sulfamoylamino)methyl)phenyl)-N-((2-m-tolyl-6-(trifluoromethyl)pyridin-3-yl)methyl)propanamide;
93 (S)—N-((2-(3-chlorophenyl)-6-(trifluoromethyl)pyridin-3-yl)methyl)-2-(3-fluoro-4-(methylsulfonamidomethyl)phenyl)propanamide;
94 (R)—N-((2-(3-chlorophenyl)-6-(trifluoromethyl)pyridin-3-yl)methyl)-2-(3-fluoro-4-(methylsulfonamidomethyl)phenyl)propanamide;
95 (S)-2-(3-fluoro-4-(methylsulfonamidomethyl)phenyl)-N-((2-(3-fluoro-4-methylphenyl)-6-(trifluoromethyl)pyridin-3-yl)methyl)propanamide;
96 (R)-2-(3-fluoro-4-(methylsulfonamidomethyl)phenyl)-N-((2-(3-fluoro-4-methylphenyl)-6-(trifluoromethyl)pyridin-3-yl)methyl)propanamide;
97 2-(3-methyl-4-(methylsulfonamidomethyl)phenyl)-N-((2-m-tolyl-6-(trifluoromethyl)pyridin-3-yl)methyl)propanamide;
98 N-((2-(3-chlorophenyl)-6-(trifluoromethyl)pyridin-3-yl)methyl)-2-(4-((sulfamoylamino)methyl)phenyl)propanamide;
99 N-((2-(3-methoxyphenyl)-6-(trifluoromethyl)pyridin-3-yl)methyl)-2-(4-((sulfamoylamino)methyl)phenyl)propanamide;
100 N-((2-(3-fluorophenyl)-6-(trifluoromethyl)pyridin-3-yl)methyl)-2-(4-((sulfamoylamino)methyl)phenyl)propanamide;
101 N-((2-(3-fluoro-4-methylphenyl)-6-(trifluoromethyl)pyridin-3-yl)methyl)-2-(4-((sulfamoylamino)methyl)phenyl)propanamide;
102 N-((2-(3-chlorophenyl)-6-(trifluoromethyl)pyridin-3-yl)methyl)-2-(3-fluoro-4-((sulfamoylamino)methyl)phenyl)propanamide;
103 2-(3-fluoro-4-((sulfamoylamino)methyl)phenyl)-N-((2-(3-methoxyphenyl)-6-(trifluoromethyl)pyridin-3-yl)methyl)propanamide;
104 2-(3-fluoro-4-((sulfamoylamino)methyl)phenyl)-N-((2-(3-fluorophenyl)-6-(trifluoromethyl)pyridin-3-yl)methyl)propanamide; and
105 2-(3-fluoro-4-((sulfamoylamino)methyl)phenyl)-N-((2-(3-fluoro-4-methylphenyl)-6-(trifluoromethyl)pyridin-3-yl)methyl)propanamide;

optionally in the form of a single stereoisomer or a mixture of stereoisomers, in the form of the free compound and/or a physiologically acceptable salt thereof.

13. A pharmaceutical composition comprising at least one substituted compound according to claim 1 and a pharmaceutically acceptable auxiliary.

14. A method for treating and/or preventing pain comprising administering to a mammal an effective amount of at least one compound according to claim 1.

15. The method according to claim 14, wherein the pain is selected from the group consisting of acute pain, chronic pain, neuropathic pain, visceral pain and joint pain.

* * * * *